(12) United States Patent
Ruggeri et al.

(10) Patent No.: US 12,421,298 B2
(45) Date of Patent: Sep. 23, 2025

(54) COMPOSITIONS AND METHODS FOR EVALUATING ANTICOAGULANT THERAPEUTIC EFFICACY

(71) Applicant: The Scripps Research Institute, La Jolla, CA (US)

(72) Inventors: Zaverio Ruggeri, La Jolla, CA (US); Wolfram Ruf, San Diego, CA (US); Yuichi Kamikubo, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 1003 days.

(21) Appl. No.: 17/459,395

(22) Filed: Aug. 27, 2021

(65) Prior Publication Data

US 2021/0395341 A1 Dec. 23, 2021

Related U.S. Application Data

(63) Continuation of application No. 16/099,977, filed as application No. PCT/US2017/032514 on May 12, 2017, now Pat. No. 11,136,370.

(60) Provisional application No. 62/336,264, filed on May 13, 2016.

(51) Int. Cl.
*C07K 14/745* (2006.01)
*A61P 7/02* (2006.01)
*C12N 9/64* (2006.01)
*G01N 33/86* (2006.01)

(52) U.S. Cl.
CPC ............ *C07K 14/745* (2013.01); *A61P 7/02* (2018.01); *C12N 9/644* (2013.01); *C12Y 304/21022* (2013.01); *G01N 33/86* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 5,110,730 | A | * | 5/1992 | Edgington | ............ | C07H 21/00 |
|  |  |  |  |  |  | 435/69.6 |
| 7,235,377 | B2 |  | 6/2007 | Mann et al. |  |  |
| 2009/0298103 | A1 |  | 12/2009 | Mann et al. |  |  |
| 2009/0298108 | A1 |  | 12/2009 | Schultz et al. |  |  |
| 2013/0052672 | A1 |  | 2/2013 | Varadi et al. |  |  |

FOREIGN PATENT DOCUMENTS

| AU | 2006200265 A1 | 2/2006 |  |  |
| JP | 6883899 B1 | 6/2021 |  |  |
| WO | 0234109 A2 | 5/2002 |  |  |
| WO | WO-2010080623 A2 * | 7/2010 | ............ | C07K 16/36 |
| WO | 2015066700 A2 | 5/2015 |  |  |
| WO | 2015091115 A1 | 6/2015 |  |  |
| WO | 2015066700 A3 | 7/2015 |  |  |

OTHER PUBLICATIONS

Kirchofer et al., Thromb Haemost. Dec. 2000;84(6):1072-81. PMID: 11154116.*
Edwards et al., J Mol Biol. Nov. 14, 2003;334(1):103-18. doi: 10.1016/j.jmb.2003.09.054. PMID: 14596803.*
Llyod et al., Protein Eng Des Sel. Mar. 2009;22(3):159-68. doi: 10.1093/protein/gzn058. Epub Oct. 29, 2008. PMID: 18974080.*
Goel et al., J Immunol. Dec. 15, 2004; 173(12):7358-67 PMID: 15585860 DOI: 10.4049/jimmunol.173.12.7358.*
Kanyavuz et al., Nat Rev Immunol. Jun. 2019;19(6):355-368. doi: 10.1038/S41577-019-0126-7. PMID: 30718829.*
Moroi et al., Blood. Sep. 15, 1996;88(6):2081-92. PMID: 8822927.*
Colace et al., Arterioscler Thromb Vasc Biol. Jun. 2012;32(6):1466-76. doi: 10.1161/ATVBAHA.112.249789. Epub Apr. 19, 2012. PMID: 22516070.*
Mendolicchio et al., Blood (2013) 122 (21): 1144., https://doi.org/10.1182/blood.V122.21.1144.1144.*
Anti-Tissue factor [5G9] antibody catalog listing page from absoluteantibody.com/product/anti-tissue-factor-5g9/, downloaded Apr. 3, 2025, 4 pages.*
Office Action for Japanese Patent Application No. 2022-001578 dated Mar. 28, 2023 including translation; 13 pgs.
Dickinson et al., "Influence of Cofactor Binding and Active Site Occupancy on the Conformation of the Macromolecular Substrate Exosite of Factor Vlla," J. Mol. Biol., 1998; 277(4):959-971.
Hemker et al., "The Calibrated Automated Thrombogram (CAT): a universal routine test for hyper- and hypocoagulability," Pathophysiol Haemost Thromb., 2002; 32:249-253.
Kamikubo et al., "Selective factor VIII activation by the tissue factor-factor VIIa-factor Xa complex," Blood, Oct. 5, 2017; 130(14):1661-1670.
Lipets et al., "Circulating Contact-Pathway-Activating Microparticles Together with Factors IXa and XIa Induce Spontaneous Clotting in Plasma of Hematology and Cardiologic Patients," PLOS One; Jan. 2014; 9(1):e87692; 11 pgs.
Mackman, N., "The Role of Tissue Factor and Factor VIIa in Hemostasis," Anesth Analg., May 2009; 108(5):1447-1452.
Mcintosh et al., "A modified thrombin generation test for the measurement of factor VIII concentrates," Journal of Thrombosis and Haemostasis, 2003; 1:1005-1011.
Ninivaggi et al., "Thrombin generation assay using factor IXa as a trigger to quantify accurately factor VIII levels in haemophilia A," Journal of Thrombosis and Haemostasis, 2011; 9:1549-1555.

(Continued)

*Primary Examiner* — Michael Szperka
(74) *Attorney, Agent, or Firm* — Umberg Zipser LLP

(57) ABSTRACT

In various embodiments, disclosed herein are methods of assessing therapeutic efficacy of an anticoagulant. Preferably, the method comprising providing a blood sample; perfusing the blood sample over a surface coated with collagen or immobilized rTF; measuring platelet aggregation and fibrin deposition on the surface coated with collagen or immobilized rTF; and assessing therapeutic efficacy of the anticoagulant based on the volume of platelet aggregates and/or deposited fibrin.

7 Claims, 25 Drawing Sheets

Specification includes a Sequence Listing.

(56) References Cited

OTHER PUBLICATIONS

Office Action for Japanese Patent Application No. JP2018-559931 issued Jan. 14, 2020; 3 pgs.
Onasoga-Jarvis et al., "Thrombin generation and fibrin formation under flow on biomimetic tissue factor-rich surfaces," J. Thromb. Haemost., 2014; 12:373-382.
Partial Supplementary European search report for Patent Application No. 17796981.3 dated Nov. 11, 2019; 15 pgs.
Van Veen et al., "Calibrated automated thrombin generation and modified thromboelastometry in haemophilia A," Thrombosis Research, 2009; 123:895-901.
Veer et al., "Regulation of Tissue Factor Initiated Thrombin Generation by the Stoichiometric Inhibitors Tissue Factor Pathway Inhibitor, Antithrombin-III, and Heparin Cofactor-II," J. Biol. Chem., 1997; 272:4367-4377.
Vignoli et al., "Tissue Factor Expression on Platelet Surface during Preparation and Storage of Platelet Concentrates," Transfus Med Hemother., 2013; 40:126-132.
Coatest SP FVIII—82 4086 63, Printed Insert Sheet, Revision Issued Feb. 2016, Chromogenix Instrumentation Laboratory Company, Bedford, MA 01730-2443; Feb. 1, 2016; 3 pgs.
Office Action for European Patent Application No. 23192817 dated Mar. 18, 2024; 9 pgs.

\* cited by examiner

```
                        SEQUENCE LISTING

<160> NUMBER OF SEQ ID NOS: 1

<210> SEQ ID NO 1
<211> LENGTH: 466
<212> TYPE: PRT
<213> ORGANISM: Homo sapiens

<400> SEQUENCE: 1

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175
```

```
Gly Tyr Ser Leu Leu Ala Asp Gly Val Ser Cys Thr Pro Thr Val Glu
            180                 185                 190
Tyr Pro Cys Gly Lys Ile Pro Ile Leu Glu Lys Arg Asn Ala Ser Lys
        195                 200                 205
Pro Gln Gly Arg Ile Val Gly Gly Lys Val Cys Pro Lys Gly Glu Cys
    210                 215                 220
Pro Trp Gln Val Leu Leu Leu Val Asn Gly Ala Gln Leu Cys Gly Gly
225                 230                 235                 240
Thr Leu Ile Asn Thr Ile Trp Val Val Ser Ala Ala His Cys Phe Asp
                245                 250                 255
Lys Ile Lys Asn Trp Arg Asn Leu Ile Ala Val Leu Gly Glu His Asp
            260                 265                 270
Leu Ser Glu His Asp Gly Asp Glu Gln Ser Arg Arg Val Ala Gln Val
        275                 280                 285
Ile Ile Pro Ser Thr Tyr Val Pro Gly Thr Thr Asn His Asp Ile Ala
    290                 295                 300
Leu Leu Arg Leu His Gln Pro Val Val Leu Thr Asp His Val Val Pro
305                 310                 315                 320
Leu Cys Leu Pro Glu Arg Thr Phe Ser Glu Arg Thr Leu Ala Phe Val
                325                 330                 335
Arg Phe Ser Leu Val Ser Gly Trp Gly Gln Leu Leu Asp Arg Gly Ala
            340                 345                 350
Thr Ala Leu Glu Leu Met Val Leu Asn Val Pro Arg Leu Met Thr Gln
        355                 360                 365
Asp Cys Leu Gln Gln Ser Arg Lys Val Gly Asp Ser Pro Asn Ile Thr
    370                 375                 380
Glu Tyr Met Phe Cys Ala Gly Tyr Ser Asp Gly Ser Lys Asp Ser Cys
385                 390                 395                 400
Lys Gly Asp Ser Gly Gly Pro His Ala Thr His Tyr Arg Gly Thr Trp
                405                 410                 415
Tyr Leu Thr Gly Ile Val Ser Trp Gly Gln Gly Cys Ala Thr Val Gly
            420                 425                 430
His Phe Gly Val Tyr Thr Arg Val Ser Gln Tyr Ile Glu Trp Leu Gln
        435                 440                 445
Lys Leu Met Arg Ser Glu Pro Arg Pro Gly Val Leu Leu Arg Ala Pro
    450                 455                 460
Phe Pro
465
```

COMPOSITIONS AND METHODS FOR EVALUATING ANTICOAGULANT THERAPEUTIC EFFICACY

This application is a continuation of U.S. patent application Ser. No. 16/099,977, which application is the US National Phase of PCT Appl No.: PCT/US2017/032514, which application claims the benefit of priority to the U.S. Patent Appl. No. 62/336,264. Each of the above applications are incorporated by reference in its entirety, including the drawings and the sequence listings.

INCORPORATION OF SEQUENCE LISTING

This application contains references to nucleic acid and polypeptide sequences which have been submitted concurrently herewith as the sequence listing text file "Sequence_Listing", created on Apr. 4, 2018. The file is 4.18 kilobytes (kb) in size. The aforementioned sequence listing is hereby incorporated by reference in its entirety pursuant to 37 C.F.R. § 1.52(e).

FIELD OF THE INVENTION

The present disclosure is in the medical and biomedical field, specifically in the area of bleeding disorders.

BACKGROUND OF THE DISCLOSURE

Blood coagulation activation is key for hemostasis and innate immunity in response to tissue injury, but contributes also to vascular thrombosis and, thus, to the pathogenesis of serious diseases. In the current coagulation scheme, the extrinsic pathway initiation complex of factor (F) VIIa and tissue factor (TF) promotes a cascade of proteolytic reactions yielding FXa that, with FVa, forms active prothrombinase and converts prothrombin (FII) to thrombin (FIIa). Initially generated thrombin was thought to be the key for coagulation amplification by feedback activation of FVIII and FV cofactors, but recent data indicate that FXa is more likely responsible for FV activation during coagulation initiation.

Present literature is unclear whether additional reactions, such as activation of FVIII catalyzed by FXa or TF-FVIIa, play a significant role in triggering coagulation. The current coagulation scheme supported by current knowledge cannot explain why drugs selectively targeting the common coagulation pathway proteases, FXa and thrombin, reduce the risk of major and severe intracranial bleeding when dosed to achieve similar antithrombotic efficacy as vitamin K antagonists affecting multiple coagulation factors.

Thus there remains a need in the field to provide a mechanistic explanation for the reduced interference of anti-thrombotic FXa inhibitors with hemostatic coagulation for the development of novel and more effective medical treatments as well as diagnostic and prognostic tests.

SUMMARY OF THE DISCLOSURE

Various embodiments disclosed herein include a highly sensitive and rapid assay for measuring thrombin generated (TG) in a blood sample, comprising: incubating the blood sample with Tissue Factor (TF), FIXa, and $CaCl_2$ for up to 5 minutes; and measuring TG in the blood sample by using H-D-cyclohexyl-alanyl-alanyl-argininyl-amidomethylcoumarin (AMC) and/or butyloxycarbonyl-valyl-prolinyl-argininyl-AMC (V-P-R-AMC). In one embodiment, the assay further comprises terminating the reaction in step (a) by addition of EDTA. In one embodiment, the amount of TF added to the blood sample is between 1 pM to 1 fM. In one embodiment, the amount of FIXa added to the blood sample is between 1 µM to 1 pM. In one embodiment, the amount of $CaCl_2$ added to the blood sample is between 1 mM to 999 mM. In one embodiment, the blood sample is from a severe hemophilia patient. In one embodiment, the TF is recombinant tissue factor (rTF). In one embodiment, the assay is highly sensitive, having TG detection limit of about 5 pM. In one embodiment, the assay predicts the risk of hemorrhage and thrombogenesis in a patient. In one embodiment, the assay can be completed within 10 minutes. In one embodiment, the assay further comprises determining the level of FVIII in the blood sample. In one embodiment, the assay is useful for identifying FVIII variants with improved functionality and/or increased stability. In one embodiment, the assay is useful for screening novel hemostatic agents. In one embodiment, the assay is useful to detect FVIII inhibitors in hemophilia patients with improved precision and sensitivity.

Various embodiments disclosed herein also include an assay for determining a bleeding risk in a subject, comprising: obtaining a blood sample from the subject; adding to the blood sample Tissue Factor (TF) and/or Factor IXa (FIXa); determining the amount of coagulation factor VIII (FVIII:C) in the blood sample; and determining (a) a mild bleeding risk in the subject if the amount of FVIII:C in the sample is >5 IU/dL, (b) a moderate bleeding risk in the subject if the amount of FVIII:C in the sample is 1-5 IU/dL, and (c) a severe bleeding risk in the subject if the amount of FVIII:C in the subject is <1 IU/dL. In one embodiment, the assay is capable of discriminating moderate from severe bleeding risk. In one embodiment, the amount of TF added to the blood sample is 1 fM to 1 pM. In one embodiment, the amount of FIXa added to the blood sample is 1 pM to 1 nM. In one embodiment, the assay further comprises measuring FVIII activation by using monoclonal antibody 12C7, when free FXa generation is decreased, FIXa generation by TF-FVIIa is blocked but FVIII activation by nascent TF-FVIIa is normal. In one embodiment, the assay further comprises adding T99Y mutant of FVII to the sample, and measuring FVIII activation when free FXa generation is decreased. In one embodiment, the assay further comprises adding E154A mutant of FVII to the sample, and measuring FVIII activation when free FXa generation is decreased. In one embodiment, the assay allows differentiating activation of FVIII and FV co-factors. In one embodiment, the detection limit of the amount of FVIII:C is 0.1 IU/dL or less. In one embodiment, TF and FIXa are added to the individual blood sample simultaneously. In one embodiment, the TF is in re-lipidated form. In one embodiment, the subject has been previously diagnosed with severe hemophilia A. In one embodiment, the subject has been previously diagnosed with acquired FVIII deficiency. In one embodiment, the assay further comprises an accurate characterization of bleeding phenotypes. In one embodiment, assessing blood coagulation levels is part of an overall treatment regimen for severe hemophilia A patients. In one embodiment, assessing blood coagulation levels is part of an overall replacement therapy with FVIII products. In one embodiment, the assay determines the levels of FVIII:C in severe hemophilia patients with at least 10 times greater sensitivity than currently available methods. In one embodiment, the assay is useful for monitoring treatment with FVIII concentrates and for assessment of concentrate potency. In one embodiment, the assay further comprises identifying FVIII variants with improved functionality and/or increased stability. In one embodiment, the assay further comprises screening novel hemostatic agents with improved efficacy and safety for hemophilia A treatment. In one embodiment, the assay is useful for designing new methods and kits for monitoring safety and efficacy of anti-thrombotic therapy for individual patients. In one embodiment, the assay is useful for identifying and characterizing new anti-thrombotic agents with improved therapeutic efficacy. In one embodiment, the assay is useful for identifying and characterizing new anti-thrombotic agents with reduced impact for hemostasis. In one embodiment, the assay reduces life-threatening bleeding complication such as spontaneous or post-traumatic intracranial hemorrhage. In one embodiment, the assay is useful for identifying novel hemostatic agents with improved efficacy and safety. In one embodiment, the subject has congenital or acquired deficiencies of FVIII and FIX. In one embodiment, the assay measures the relative contribution of native TF-FVIIa-FXa to the generation of active FVIIIa cofactor as distinct from FVIIIa activation by free FXa or the thrombin-feedback loop. In one embodiment, the assay activates FVIII, but not FV, and does so without requiring initial thrombin generation. In one embodiment, the free FXa activates FV to FVa.

Various embodiments disclosed herein further include kits useful for determining blood coagulation, comprising: a composition comprising Tissue factor (TF), Factor IXa (FIXa), procoagulant phospholipids (PL), and/or Factor IIa (FIIa), or a pharmaceutical equivalent, derivative, analog, and/or salt thereof. In one embodiment, the kit further comprises a composition comprising H-D-cyclohexyl-alanyl-alanyl-argininyl-amidomethylcoumarin (AMC) and/or butyloxycarbonyl-valyl-prolinyl-argininyl-AMC (V-P-R-AMC). In one embodiment, the kit further comprises an apparatus for determining levels of FVIII:C activity. In one embodiment, the kit further comprises an apparatus for determining amount of TG. In one embodiment, the TF and/or FIXa composition is in picomolar and/or nanomolar dosages. In one embodiment, the kit is useful for individualized diagnosis of hemophilia patients. In one embodiment, the kit is useful for predicting bleeding risk in patients with congenital and acquired FVIII:C defects. In one embodiment, the kit is useful for monitoring and evaluation of anti-thrombotic regiments. In one embodiment, the kit further comprises diagnosing, monitoring, and/or evaluation of a disease based on treatment of drugs or combination of drugs.

Various embodiments disclosed herein also include a method of diagnosing, monitoring, or prognosing a disease in a patient, comprising: obtaining a blood plasma sample from the patient; incubating the blood sample with tissue factor (TF), FIXa and/or $CaCl_2$; assaying the sample to determine the level of FVIII:C and/or thrombin generated (TG); and diagnosing, monitoring, or prognosing the disease based on the amount of FVIII:C in the sample. In one embodiment, the disease is a bleeding disorder. In one embodiment, the disease is a thrombotic disorder. In one embodiment, the disease is a hemostatic disorder. In one embodiment, the patient has a mild bleeding risk if the amount of FVIII:C level detected is more than 5 IU/dL. In one embodiment, the patient has a moderate bleeding risk if the amount of FVIII:C level detected is between 1-5 IU/dL. In one embodiment, the patient has a severe bleeding risk if the amount of FVIII:C level detected is between 1-0.1 IU/dL. In one embodiment, TF and/or FIXa are administered to the patient blood sample in picomolar or nanomolar amounts. In one embodiment, the method further comprises additional treatment by administering an appropriate treatment of anti-thrombosis. In one embodiment, the method further comprises administering a combination of drugs for the treatment of thrombosis. In one embodiment, the method is useful for achieving an individualized treatment with different target-selective anticoagulants on mechanistic ground. In one embodiment, the patient is undergoing treatment with an anti-coagulant. In one embodiment, the anticoagulant is an oral anticoagulant. In one embodiment, the assay can detect low levels of FVIII:C in severe hemophilia A patients. In one embodiment, the assay can detect low levels of FVIII:C in individuals with acquired FVIII deficiency. In one embodiment, FVIII activity assays with increased sensitivity allows a more accurate characterization of bleeding phenotypes. In one embodiment, the FVIII activity assays with increased sensitivity allows a prediction of bleeding risk in severe hemophilia A patients. In one embodiment, the assay helps identify variants of anti-hemophilic FVIII with gain of function and/or increased stability in the newly identified coagulation pathway, thus improving replacement therapy in patients with defective anti-hemophilic FVIII function.

Other embodiments disclosed herein include a method of screening and/or evaluating new anti-thrombotic or pro-hemostatic drug candidates comprising: providing a blood plasma sample of a patient; adding to the blood sample a composition comprising TF, FIXa, and/or $CaCl_2$) and assaying the sample to determine FVIII:C level or thrombin generated (TG) level; and screening and/or evaluating new anti-thrombotic or pro-hemostatic drug candidates based on the FVIII:C level or thrombin generated (TG) level. In one embodiment, TF and FIXa are added to the blood sample in picomolar or nanomolar amounts. In one embodiment, evaluating new anti-thrombotic or pro-hemostatic agents comprises designing or screening for new anti-thrombotic or pro-hemostatic agents. In one embodiment, the anti-thrombotic or pro-hemostatic agents has improved therapeutic efficacy. In one embodiment, the anti-thrombotic or pro-hemostatic agents have improved safety profile. In one embodiment, evaluating new anti-thrombotic drug candidates specifically and quantitatively focuses on functional preservation or degradation of coagulation cofactors in the context of TF-initiated clotting, differentiating between pro-thrombotic and pro-hemostatic pathways. In one embodiment, the anti-thrombotic or pro-hemostatic agents are evaluated based on the best profile for antithrombotic effects versus safety profile with respect to bleeding complications.

Various embodiments disclosed herein also include a method of assessing therapeutic efficacy of an anticoagulant, comprising: providing a blood sample; perfusing the blood sample over a surface coated with collagen or immobilized rTF; measuring platelet aggregation and fibrin deposition on the surface coated with collagen or immobilized rTF; and assessing therapeutic efficacy of the anticoagulant based on the volume of platelet aggregates and/or deposited fibrin. In one embodiment, the anticoagulant is an FXa targeting coagulant. In one embodiment, the anticoagulant is heparin (anti-thrombin cofactor), warfarin (vitamin K antagonist), dabigatran (direct thrombin inhibitor), rivaroxaban and/or apixaban (two direct FXa inhibitors). In one embodiment, the coagulant is a targeted coagulant, such as an aptamer that decreases FXI level, and thus activity in plasma. In one embodiment, the perfusion is at a wall shear rate of $300\ s^{-1}$ for 5 minutes.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
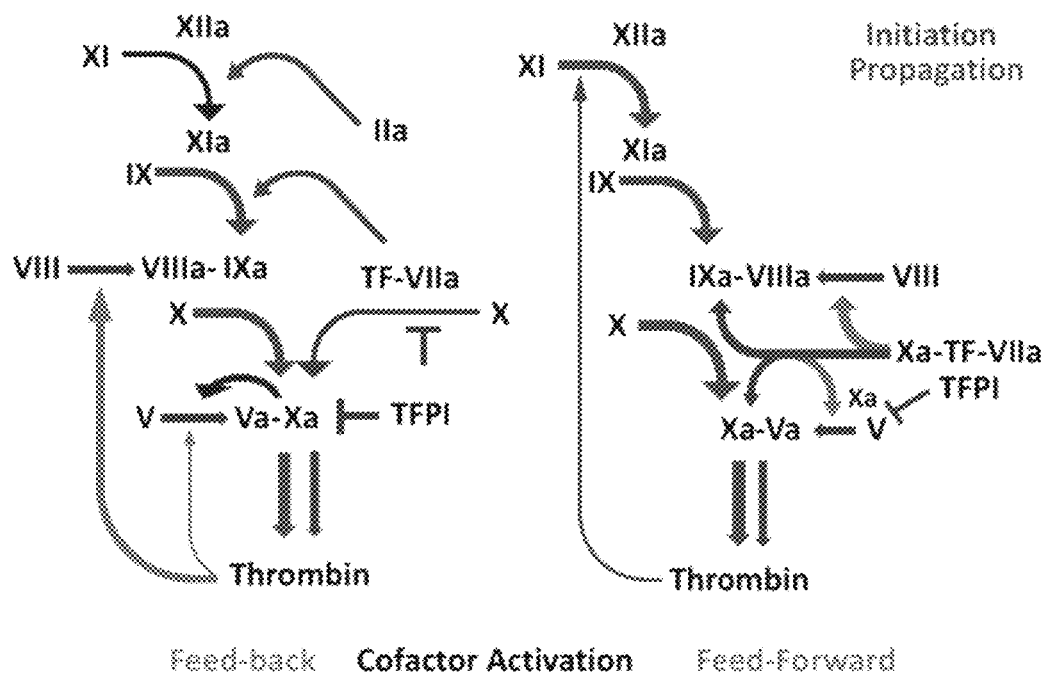
FIG. 1 illustrates, in accordance with embodiments herein, different schematic representations of coagulation initiation and amplification. In the current paradigm (left), activation of the FVIII and FV cofactors is considered to be primarily thrombin-mediated, although a key role of FXa relative to thrombin has been highlighted for FV activation. On the right is the novel coagulation scheme as described in this disclosure. FVIII is activated by nascent FXa within the extrinsic TF-FVIIa-FXa initiation complex prior to inhibition by TFPI. By concurrently activating FIX, the extrinsic TF-FVIIa complex can initiate directly the anti-hemophilic pathway and not only amplify intrinsic coagulation, as currently thought. The two depicted pathways of coagulation activation may be variably integrated in responses to different stimuli.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "subject" can be a vertebrate, such as a mammal, a fish, a bird, a reptile, or an amphibian. Thus, the subject of the present disclosure can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal.

As used herein, the term "patient" refers to a subject afflicted with a disease or disorder. The term "patient" includes human and veterinary subjects. In some aspects of the disclosed methods, the subject has been diagnosed with a need for treatment for a blood disorder and related diseases including, but not limited to a bleeding disorder, such as for example, hemophilia A (Factor VIII deficiency), hemophilia B (Factor IX deficiency), Von Willebrand disease, and rare factor deficiencies including Factors I, II, V, VII, X, XI, XII, and XIII, etc.

As used herein, the term "FVIII:C" contemplates plasma FVIII coagulant activity. In some embodiments, the term FVIII:C may refer to the concentration of FVIIIa in plasma. In some embodiments, the term FVIII:C may refer to the FVIII procoagulant function. As described throughout this disclosure, a previously unknown FVIII activation pathway is disclosed, wherein FVIII procofactor is converted to FVIIIa active cofactor independently of the FIIa feedback activation. In some embodiments, FVIII:C may be measured as described in the examples, assays, methods, and kits, of this disclosure. In some embodiments of this disclosure, hemophilia patients have been classified into three categories based on plasma FVIII coagulant activity (FVIII:C)—severe if FVIII:C level is less than 1 IU/dL; moderate if FVIII:C level is between 1 IU/dL and 5 IU/dL; and mild if FVIII:C level is more than 5 IU/dL.

As used herein, the terms "Factor IIa," "FIIa" and "Thrombin Generated" (TG), used interchangeably herein, refer to an enzyme in the blood plasma that causes the clotting of blood by converting fibrinogen to fibrin. TG may also refer to the amount of thrombin generated as a result of the assays disclosed herein.

As disclosed herein, the inventors have developed various assays and methods that may be used for assessing blood coagulation in a subject. The inventors have disclosed a new coagulation initiating pathway in which the TF-FVIIa-nascent FXa complex directly activates FVIII apart from thrombin feedback. Direct activation of the intrinsic pathway by TF may preserve hemostasis under anticoagulant therapy targeting thrombin amplification.

In one embodiment, disclosed herein is a highly sensitive and rapid assay for measuring thrombin generated (TG) in a blood sample, comprising: incubating the blood sample with Tissue Factor (TF), FIXa, and $CaCl_2$ for up to 5 minutes; and measuring TG in the blood sample by using H-D-cyclohexyl-alanyl-alanyl-argininyl-amidomethylcoumarin (AMC) and/or butyloxycarbonyl-valyl-prolinyl-argininyl-AMC (V-P-R-AMC). In one embodiment, the assay further comprises terminating the reaction in step (a) by addition of EDTA. In one embodiment, the amount of TF added to the blood sample is between 1 pM to 1 fM. In one embodiment, the amount of FIXa added to the blood sample is between 1 uM to 1 pM. In one embodiment, the amount of $CaCl_2$ added to the blood sample is between 1 mM to 999 mM. In one embodiment, the blood sample is from a severe hemophilia patient. In one embodiment, the TF is recombinant tissue factor (rTF). In one embodiment, the assay is highly sensitive, having TG detection limit of about 5 pM. In one embodiment, the assay predicts the risk of hemorrhage and thrombogenesis in a patient. In one embodiment, the assay can be completed within 10 minutes. In one embodiment, the assay further comprises determining the level of FVIII in the blood sample. In one embodiment, the assay is useful for identifying FVIII variants with improved functionality and/or increased stability. In one embodiment, the assay is useful for screening novel hemostatic agents.

In one embodiment, disclosed herein is an assay for determining a bleeding risk in a subject, comprising: obtaining a blood sample from the subject; adding to the blood sample Tissue Factor (TF) and/or Factor IXa (FIXa); determining the amount of coagulation factor VIII (FVIII:C) in the blood sample; and determining (a) a mild bleeding risk in the subject if the amount of FVIII:C in the sample is >5 IU/dL, (b) a moderate bleeding risk in the subject if the amount of FVIII:C in the sample is 1-5 IU/dL, and (c) a severe bleeding risk in the subject if the amount of FVIII:C in the subject is <1 IU/dL. In one embodiment, the assay is capable of discriminating moderate from severe bleeding risk. In one embodiment, the amount of TF added to the blood sample is 1 fM to 1 pM. In one embodiment, the amount of FIXa added to the blood sample is 1 pM to 1 nM. In one embodiment, the assay further comprises measuring FVIII activation by using monoclonal antibody 12C7, when free FXa generation is decreased. In one embodiment, the assay further comprises adding T99Y mutant of FVII to the sample, and measuring FVIII activation when free FXa generation is decreased. In another embodiment, the assay further comprises adding E154A mutant of FVII to the sample, and measuring FVIII activation when free FXa generation is decreased. In one embodiment, the assay allows differentiating activation of FVIII and FV co-factors. In one embodiment, the detection limit of the amount of FVIII:C is 0.1 IU/dL or less. In one embodiment, TF and FIXa are added to the individual blood sample simultaneously. In one embodiment, the TF is in re-lipidated form. In one embodiment, the subject has been previously diagnosed with severe hemophilia A. In one embodiment, the subject has been previously diagnosed with acquired FVIII deficiency. In one embodiment, the assay further comprises an accurate characterization of bleeding phenotypes. In one embodiment, assessing blood coagulation levels is part of an overall treatment regimen for severe hemophilia A patients. In one embodiment, assessing blood coagulation levels is part of an overall replacement therapy with FVIII products. In one embodiment, the assay determines the levels of FVIII:C in severe hemophilia patients with at least 10 times greater sensitivity than currently available methods. In one embodiment, the assay is useful for monitoring treatment with FVIII concentrates and for assessment of concentrate potency. In one embodiment, the assay further comprises identifying FVIII variants with improved functionality and/or increased stability. In one embodiment, the assay further comprises screening novel hemostatic agents with improved efficacy and safety for hemophilia A treatment. In one embodiment, the assay is useful for designing new methods and kits for monitoring safety and efficacy of anti-thrombotic therapy for individual patients. In one embodiment, the assay is useful for identifying and characterizing new anti-thrombotic agents with improved therapeutic efficacy. In one embodiment, the assay is useful for identifying and characterizing new anti-thrombotic agents with reduced impact for hemostasis. In one embodiment, the assay reduces life-threatening bleeding complication such as spontaneous or post-traumatic intracranial hemorrhage. In one embodiment, the assay is useful for identifying novel hemostatic agents with improved efficacy and safety. In one embodiment, the subject has congenital or acquired deficiencies of FVIII and FIX.

In one embodiment, the assays disclosed herein measures the relative contribution of native TF-FVIIa-FXa to the generation of active FVIIIa cofactor as distinct from FVIIIa activation by free FXa or the thrombin-feedback loop. In one embodiment, the assay activates FVIII, but not FV, and does so without requiring initial thrombin generation. In one embodiment, wherein the free FXa activates FV to FVa. Thus, the assay formats described herein can measure in a plasma or blood sample the relative contribution of native TF-FVIIa-FXa to the generation of active FVIIIa cofactor as distinct from FVIIIa activation by free FXa or the thrombin-feedback loop.

"Native" TF-FVIIa-FXa, as used herein, refers to the conversion of the initial TF-FVIIa-FX complex, in which FX is inactive, to TF-FVIIa-FXa, in which TF-associated FVIIa has converted FX into FXa active protease, has taken place, but FXa is still associated with TF-FVIIa. The unique property of this complex, never before recognized, is the ability to activate selectively FVIII to FVIIIa while escaping inhibition by physiologic as well as pharmacologic inhibitors of FXa. In one embodiment, the importance of this finding is that free FXa—i.e. the FX that has been activated by TF-FVIIa but released from the complex—in addition to FVIII activates also FV to FVa. FVa is the essential cofactor of the prothrombinase complex (FVa-FXa complex), essential for the efficient conversion of prothrombin into thrombin, which is the final active protease product of the coagulation system. Thrombin clots fibrinogen and activates platelets, both essential for normal hemostasis but also the cause of pathological thrombosis. In normal conditions, control by specific physiologic inhibitors ensures the balance that permits sufficient thrombin to be produces at the right time in the right location to support hemostasis. Uncontrolled thrombin generation becomes the cause of endovascular thrombosis in pathological conditions. Thus, the discovery of a reaction that activates FVIII but not FV and does so without requiring initial thrombin generation and the description of methods sensitive to the occurrence of this reaction is one important aspect of the disclosure because it provides a quantitative assessment of a pathway that can explain and gauge the preservation of hemostasis in the context of the use of anticoagulants that must dampen thrombin generation to cure or prevent thrombosis. Activating FVIII to FVIIIa without producing FVa at the same time is a mechanism that can bias the coagulation response towards hemostasis as opposed to thrombosis. Assessing quantitatively the relative function of this pathway is important in establishing risk of bleeding vs. risk of thrombosis in untreated individuals or patients receiving anticoagulants of different kind.

In one embodiment, disclosed herein is a kit useful for determining blood coagulation, comprising: a composition comprising Tissue factor (TF), Factor IXa (FIXa), procoagulant (PL), and/or Factor IIa (FIIa), or a pharmaceutical equivalent, derivative, analog, and/or salt thereof. In one embodiment, the kit further comprises a composition comprising H-D-cyclohexyl-alanyl-alanyl-argininyl-amidomethylcoumarin (AMC) and/or butyloxycarbonyl-valyl-prolinyl-argininyl-AMC (V-P-R-AMC). In one embodiment, the kit further comprises an apparatus for determining levels of FVIII:C activity. In one embodiment, the kit further comprises an apparatus for determining amount of TG. In one embodiment, the TF and/or FIXa composition is in picomolar and/or nanomolar dosages. In one embodiment, the kit is useful for individualized diagnosis of hemophilia patients. In one embodiment, the kit is useful for predicting bleeding risk in patients with congenital and acquired FVIII:C defects. In one embodiment, the kit is useful for monitoring and evaluation of anti-thrombotic regiments. In one embodiment, the kit further comprises diagnosing, monitoring, and/or evaluation of a disease based on treatment of drugs or combination of drugs.

In one embodiment, disclosed herein is a method of diagnosing, monitoring, or prognosing a disease in a patient, comprising: obtaining a blood plasma sample from the patient; incubating the blood sample with tissue factor (TF), FIXa and/or $CaCl_2$; assaying the sample to determine the level of FVIII:C and/or thrombin generated (TG); and diagnosing, monitoring, or prognosing the disease based on the amount of FVIII:C in the sample. In one embodiment, the disease is a bleeding disorder. In one embodiment, the disease is a thrombotic disorder. In one embodiment, the disease is a hemostatic disorder. In one embodiment, the patient has a mild bleeding risk if the amount of FVIII:C level detected is more than 5 IU/dL. In one embodiment, the patient has a moderate bleeding risk if the amount of FVIII:C level detected is between 1-5 IU/dL. In one embodiment, the patient has a severe bleeding risk if the amount of FVIII:C level detected is between 1-0.1 IU/dL. In one embodiment, TF and/or FIXa are administered to the patient blood sample in picomolar or nanomolar amounts. In one embodiment, the method further comprises additional treatment by administering an appropriate treatment of anti-thrombosis. In one embodiment, the method further comprises administering a combination of drugs for the treatment of thrombosis. In one embodiment, the method is useful for achieving an individualized treatment with different target-selective anticoagulants on mechanistic ground. In one embodiment, the patient is undergoing treatment with an anti-coagulant. In one embodiment, the anti-coagulant is an oral anticoagulant. In one embodiment, the assay can detect low levels of FVIII:C in severe hemophilia A patients. In one embodiment, the assay can detect low levels of FVIII:C in individuals with acquired FVIII deficiency. In one embodiment, FVIII activity assays with increased sensitivity allows a more accurate characterization of bleeding phenotypes. In one embodiment, the FVIII activity assays with increased sensitivity allows a prediction of bleeding risk in severe hemophilia A patients. In one embodiment, the assay helps identify variants of anti-hemophilic FVIII with gain of function and/or increased stability in the newly identified coagulation pathway, thus improving replacement therapy in patients with defective anti-hemophilic FVIII function.

In one embodiment, disclosed herein is a method of screening and/or evaluating new anti-thrombotic or pro-hemostatic drug candidates comprising: providing a blood plasma sample of a patient; adding to the blood sample a composition comprising TF, FIXa, and/or $CaCl_2$ and assaying the sample to determine FVIII:C level or thrombin generated (TG) level; and screening and/or evaluating new anti-thrombotic or pro-hemostatic drug candidates based on the FVIII:C level or thrombin generated (TG) level. In one embodiment, TF and FIXa are added to the blood sample in picomolar or nanomolar amounts. In one embodiment, evaluating new anti-thrombotic or pro-hemostatic agents comprises designing or screening for new anti-thrombotic or pro-hemostatic agents. In one embodiment, the anti-thrombotic or pro-hemostatic agents has improved therapeutic efficacy. In one embodiment, the anti-thrombotic or pro-hemostatic agents have improved safety profile. In one embodiment, evaluating new anti-thrombotic drug candidates specifically and quantitatively focuses on functional preservation or degradation of coagulation cofactors in the context of TF-initiated clotting, differentiating between pro-thrombotic and pro-hemostatic pathways. In one embodiment, the anti-thrombotic or pro-hemostatic agents are evaluated based on the best profile for antithrombotic effects versus safety profile with respect to bleeding complications.

In one embodiment, disclosed herein is a method of assessing therapeutic efficacy of an anticoagulant, comprising: providing a blood sample; perfusing the blood sample over a surface coated with collagen or immobilized rTF; measuring platelet aggregation and fibrin deposition on the surface coated with collagen or immobilized rTF; and assessing therapeutic efficacy of the anticoagulant based on the volume of platelet aggregates and/or deposited fibrin. In one embodiment, the anticoagulant is an FXa targeting coagulant. In one embodiment, the anticoagulant is an FXa targeting coagulant. In one embodiment, the anticoagulant is heparin (anti-thrombin cofactor), warfarin (vitamin K antagonist), dabigatran (direct thrombin inhibitor), rivaroxaban and/or apixaban (two direct FXa inhibitors). In one embodiment, the coagulant is a targeted coagulant, such as an aptamer that decreases FXI level, and thus activity in plasma. In one embodiment, the perfusion is at a wall shear rate of 300 $s^{-1}$ for 5 minutes.

Safe and effective antithrombotic therapy requires understanding of mechanisms that contribute to pathological thrombosis but have lesser impact on hemostasis. As described herein, and in accordance with the various embodiments disclosed herein, the inventors found that the extrinsic tissue factor (TF) coagulation initiation complex can selectively activate the anti-hemophilic cofactor, FVIII, triggering the hemostatic intrinsic coagulation pathway independently of thrombin feedback loops. In a mouse model with a relatively mild thrombogenic lesion, TF-dependent FVIII activation sets the threshold for thrombus formation through contact phase-generated FIXa. In vitro, FXa stably associated with TF-FVIIa activates FVIII, but not FV. Moreover, nascent FXa product of TF-FVIIa can transiently escape the slow kinetics of Kunitz-type inhibition by TF pathway inhibitor (TFPI) and preferentially activates FVIII over FV. Thus, TF synergistically primes FIXa-dependent thrombin generation independent of cofactor activation by thrombin. Accordingly, FVIIa mutants deficient in direct TF-dependent thrombin generation, but preserving FVIIIa generation by nascent FXa, can support intrinsic pathway coagulation. In ex vivo flowing blood, a TF-FVIIa mutant complex with impaired free FXa generation but activating both FVIII and FIX supports efficient FVIII-dependent thrombus formation. Thus, a previously unrecognized TF-initiated pathway directly yielding FVIIIa-FIXa intrinsic tenase complex may be pro-hemostatic before further coagulation amplification by thrombin-dependent feedback loops enhances the risk of thrombosis.

In one embodiment, the present disclosure provides a method of assessing blood coagulation in a hemophilic subject, comprising adding an effective dosage of a composition comprising Tissue Factor (TF) and/or Factor IXa (FIXa) to a blood sample obtained form an individual, and assaying the sample to determine coagulation factor VIII (FVIII:C) levels. The method is capable of discriminating moderate from severe bleeding risk resulting from FVIII:C levels in the ~1-0.1 IU/dL as severe bleeding risk arises when FVIII:C is <1 IU/dL, moderate bleeding risk arises when FVIII:C is 1-5 IU/dL, and mild bleeding risk arises when FVIII:C is >5 IU/dL. In one embodiment, the method is capable of discriminating moderate bleeding risk from severe bleeding risk resulting from FVIII:C levels in the 1-0.1 IU/dL range. In some embodiments, TF and FIXa are added to the patient blood sample simultaneously. In some embodiments, the TF is in re-lipidated form. In some embodiments, TF and FIXa are added into the patient's plasma (PRP or PPP). In some embodiments, TF and FIXa are added in picomolar or nanomolar quantities. In one embodiment, the method is used on severe hemophilia A patients. In some embodiments, the method is used on patients with acquired FVIII deficiency. In some embodiments, the method enables a more accurate characterization of bleeding phenotypes. In some embodiments, the method is useful for predicting bleeding risk in severe hemophilia A patients. In one embodiment, the method improves replacement therapy with FVIII products. In some embodiments, the method determines the levels of FVIII:C in severe hemophilia patients with at least 10 times greater sensitivity. In some embodiments, the method is useful for monitoring treatment with FVIII concentrates and for assessment of concentrate potency. In some embodiments, the method further comprises identifying FVIII variants with improved functionality and/or increased stability. In some embodiments, the method further comprises screening novel hemostatic agents with improved efficacy and safety for treatment of hemophilia A or other bleeding disorders. In some embodiments, the method is useful for designing new methods and kits for monitoring safety and efficacy of anti-thrombotic therapy for individual patients. In some embodiments, the method is useful for identifying and characterizing new anti-thrombotic agents with improved therapeutic efficacy. In some embodiments, the method is useful for identifying and characterizing new anti-thrombotic agents with reduced impact for hemostasis. In some embodiments, the method reduces life-threatening bleeding complication such as spontaneous or post-traumatic intracranial hemorrhage. In some embodiments, the method is useful for identifying novel hemostatic agents with improved efficacy and safety. In some of these embodiments, the patient has congenital or acquired deficiencies of FVIII and FIX (hemophilia).

In various embodiments, disclosed herein is a method of assessing blood coagulation in a subject, comprising: obtaining a suitable blood sample from a subject; adding to the individual sample prescribed concentrations of Tissue Factor (TF) and/or Factor IXa (FIXa); and assaying the sample to determine coagulation factor VIII (FVIII:C) levels, wherein mild bleeding risk arises when FVIII:C is >5 IU/dL; moderate bleeding risk arises when FVIII:C is 1-5 IU/dL; and severe bleeding risk arises when FVIII:C is <1 IU/dL. Thus, the assay is capable of discriminating moderate from severe bleeding risk resulting from FVIII:C levels in the ~1-0.1 IU/dL. In some of these embodiments, the use of monoclonal antibody 12C7 and any equivalent of the T99Y mutation allow measuring FVIII activation when free FXa generation is decreased. In some embodiments, the method allows differentiating activation of FVIII and FV co-factors. In some embodiments, using monoclonal antibody 12C7 allows measuring FVIII activation when free FXa generation is decreased. In some embodiments, using the T99Y mutant of FVII, or any equivalent thereof, allows measuring FVIII activation when free FXa generation is decreased. In some embodiments, the T99Y mutant of FVII, or any equivalent thereof, is used to assess FXI loops similar to assay formats with monoclonal antibody 12C7.

Further disclosed herein is an assay for out-competing blood FVII binding to TF comprising (a.) Obtaining a blood sample from an individual; (b) Adding a mutant of the coagulation factor VIIa at a high concentration; and (c) Out-competing blood FVII binding to TF. In some embodiments, the mutant of coagulation factor VIIa is E154A or a similar mutant that performs the substantially similar function.

Further disclosed herein is a method for evaluating new hemostatic drug candidates comprising: (a) initiating TG in TF initiated reactions with monoclonal antibody 12C7 present; (b) determining that TG is ineffective in the presence of 12C7; (c) adding the hemostatic drug candidate; and (d) evaluating that the hemostatic drug candidate is effective if it complements the ineffective TG in TF initiated reactions with 12C7 present.

As further disclosed herein, the inventors have developed various devices and apparatuses that may be used for the assessment of blood coagulation. For example, in one embodiment, the present disclosure provides a device for assessing blood coagulation, comprising an apparatus adapted for the measurement of one or more FVIII:C levels from a sample. In another embodiment, the TF and FIX may be administered in picomolar or nanomolar amounts. In some embodiments, the device is useful for individualized diagnosis of hemophilia patients. In some embodiments, the device is useful for predicting bleeding risk in patients with congenital and acquired FVIII:C defects.

In another embodiment, the present disclosure provides a pharmaceutical composition, comprising a quantity of a composition comprising TF and/or FIXa, or a pharmaceutical equivalent, derivative, analog, and/or salt thereof, and a pharmaceutically acceptable carrier. The pharmaceutical compositions disclosed herein may also comprise a pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the present disclosure may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the present disclosure can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the present disclosure can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the present disclosure may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 21st edition, Williams & Wilkins PA, USA) (2005).

Typical dosages of an effective composition can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

In various embodiments, also disclosed herein is a diagnostic method for monitoring anti-thrombotic therapy in a patient comprising: (a) adding to the an individual patient blood sample prescribed amounts of TF and FIXa; (b) determining the FVIII:C level in the patient blood sample; and (c) monitoring anti-thrombotic therapy in the patient based on the FVIII:C level. In some embodiments, TF and FIXa are added to the patient blood sample in picomolar or nanomolar amounts. In some embodiments, the method further comprises administering a drug for the treatment of thrombosis. In some embodiments, the method further comprises administering a combination of drugs for the treatment of thrombosis. In some embodiments, the method is useful for achieving an individualized treatment with different target-selective anticoagulants on mechanistic ground.

In various embodiments, disclosed herein is a diagnostic method for assessing the risk of causing bleeding complications in a patient, comprising: (a) adding to an individual patient blood sample prescribed amounts of TF and FIXa; (b) determining the FVIII:C level in the patient; and (c) assessing the risk of causing bleeding complication in the patient based on the FVIII:C level. In some of these embodiments, TF and FIXa are added to the patient blood sample in picomolar or nanomolar amounts.

In various embodiments, disclosed herein is a method of evaluating new anti-thrombotic or pro-hemostatic drug candidates comprising: (a) adding to the individual blood sample of a patient in need thereof, prescribed amounts of TF and FIXa; (b) determining the FVIII:C level in the patient; and (c) evaluating new anti-thrombotic or pro-hemostatic drug candidates based on the FVIII:C level. In some of these embodiments, TF and FIXa are added to the patient blood sample in picomolar or nanomolar amounts. In some embodiments, evaluating new anti-thrombotic or pro-hemostatic agents comprises designing or screening for new anti-thrombotic or pro-hemostatic agents. In some embodiments, the anti-thrombotic or pro-hemostatic agents have improved therapeutic efficacy. In some embodiments, the anti-thrombotic or pro-hemostatic agents have improved safety profile. In some embodiments, evaluating new anti-thrombotic drug candidates specifically and quantitatively focuses on functional preservation or degradation of coagulation cofactors in the context of TF-initiated clotting, differentiating between pro-thrombotic and pro-hemostatic pathways. In some embodiments, the anti-thrombotic or pro-hemostatic agents are evaluated based on the best profile for antithrombotic effects versus safety profile with respect to bleeding complications.

In various embodiments, disclosed herein is an assay for determining thrombotic or hemostatic risk in a patient comprising (a) adding to an individual patient blood sample prescribed amounts of TF and FIXa; (b) measuring the FVIII:C level in the patient blood sample; and (c) determining thrombotic or hemostatic risk in the patient based on the FVIII:C level. In some embodiments, TF and FIXa are added to the patient blood sample in picomolar or nanomolar amounts. In some embodiments, the patient is undergoing treatment with anticoagulant drugs. In some embodiments, the anticoagulant is an oral anticoagulant. In some embodiments, the assay can detect low levels of FVIII:C in severe hemophilia A patients. In some embodiments, the assay can detect low levels of FVIII:C in individuals with acquired FVIII deficiency. In some embodiments, FVIII activity assays with increased sensitivity allows for a more accurate characterization of bleeding phenotypes. In some embodiments, FVIII activity assays with increased sensitivity enables a prediction of bleeding risk in severe hemophilia A patients. In some embodiments, the assay helps identify variants of anti-hemophilic FVIII with gain of function and/or increased stability in the newly identified coagulation pathway, thus improving replacement therapy in patients with defective anti-hemophilic FVIII function.

In various embodiments, disclosed herein is a novel coagulation pathway wherein nascent FXa, formed by TF-FVIIa, directly activates FVIII independently of thrombin feedback reactions. In various embodiments, disclosed herein is a composition comprising: (a) Tissue Factor (TF) and (b) Factor IXa (FIXa), wherein the composition is capable of triggering thrombin generation when it is administered into an individual's plasma. In some embodiments of this composition, the individual is a hemophilia patient.

In various embodiments, also described herein is a pathway in the initiation of thrombus formation in vivo with broad significance for thrombosis and hemostasis. In some embodiments, this novel mechanism enables better diagnostic approaches for monitoring antithrombotic therapy and the design of new hemostatic agents with improved therapeutic efficacy. In some embodiments, disclosed herein is a novel function of the tissue factor (TF) coagulation initiation complex to provide de novo generated factor Xa leading to the activation of the coagulation pro-cofactors FV and FVIII in thrombosis. In some embodiments, generation of the protease cofactor FVIIIa required for hemostasis is preserved in the presence of clinically used anticoagulants with favorable safety profiles. In one embodiment, novel assays are disclosed for the identification of variants of the anti-hemophilic FVIII and FV with improved functionality in this pathway and utility for replacement therapy. In another embodiment, disclosed herein are novel assays for the evaluation of antithrombotic drugs with beneficial efficacy to safety profiles. In still other embodiments, disclosed herein are novel assays for monitoring antithrombotic therapy based on functional preservation or degradation of coagulation cofactors in the context of TF-initiated clotting. In some embodiments, the novel drug discovery approaches and diagnostic principles disclosed herein are applicable to large patient populations under anti-thrombotic therapy and/or in need of hemostatic therapy.

In various embodiments, the novel mechanism in the coagulation process as disclosed herein provides a hitherto unknown method to identify and measure differentially the function of pro-thrombotic and pro-hemostatic coagulation pathways and, consequently, the distinct effects of inhibitors. In some embodiments, the present disclosure presents new diagnostic methods for monitoring anti-thrombotic therapy in individual patients, providing quantitative parameters that distinctly define the level of anti-thrombotic effect and the risk of causing bleeding complications. In some embodiments, this novel mechanism may guide the process of designing and/or screening for new anti-thrombotic or pro-hemostatic agents with improved therapeutic efficacy and safety profile.

In various embodiments disclosed herein are novel coagulation assays that individualize the definition of thrombotic and bleeding risk for patients treated with new oral anticoagulants. In some embodiments, the assays disclosed herein objectively identify situations requiring dosage adjustment for better anti-thrombotic effect or for reducing the possibility of bleeding complications. In some embodiments, the disclosure provides new perspectives relevant to the identification and testing of new pharmacological approaches for the prevention and treatment of thrombosis while preserving sufficient hemostatic function.

In various embodiments, described herein is a pathway in the initiation of thrombus formation in vivo with broad significance for thrombosis and hemostasis. In various embodiments, the present disclosure delineate a novel function of the extrinsic coagulation initiation complex, namely providing selective feed-forward activation of the anti-hemophilic cofactor, FVIII, independently of thrombin feedback loops (FIG. 1).

In one embodiment, disclosed herein is that the TF pathway initiation complex directly activates the key FVIII coagulation cofactors enabling contact phase (CP)- or FXIa-initiated procoagulant protease generation. In some embodiments, inefficient TFPI inhibition of cofactor FVIII activation allows continued thrombin production through the intrinsic pathway when protease generation via extrinsic pathway initiation is physiologically limited. In some embodiments, like TFPI, the FXa-directed anticoagulant drug, rivaroxaban, reduces TF-mediated thrombin generation while preserving FVIII activation. In one embodiment, the selective escape of physiologic TFPI control permits intrinsic pathway-dependent rescue of thrombin generation and may explain reduced fatal bleeding complications in rivaroxaban-treated patients. In some embodiments, this alternative coagulation mechanism defines a novel TF and CP (intrinsic pathway) synergy in thrombosis, and has broad implications for the development of improved antithrombotic and hemostatic agents.

In various embodiments, disclosed here are experiments, methods, and results showing that nascent FXa generated by the TF-FVIIa complex activates the intrinsic pathway cofactor, FVIII, directly and independently of thrombin feedback loops. This alternative mechanism leading to thrombin generation evades physiological TF pathway inhibitor (TFPI) control as well as direct FXa pharmacologic inhibitors. Consequently, these anticoagulant drugs, unlike vitamin K antagonists, preserve fibrin formation through the anti-hemophilic FVIIIa-FIXa complex when extrinsic TF pathway prothrombotic functions are limited. Resistance to FXa inhibition explains how this novel link in coagulation promotes clot formation and prevents bleeding at vulnerable sites even in the presence of therapeutic concentrations of FXa-directed anticoagulants. The present disclosure provides new perspectives for enhancing antithrombotic efficacy while limiting negative consequences on hemostasis, as well as for personalized evaluation of bleeding risk during anticoagulant therapy.

The present disclosure is also directed to a kit comprising TF and FIXa. For example, in various embodiments disclosed herein, the present disclosure provides a kit for determining FVIII:C activity in an individual, comprising TF and FIXa, wherein therapeutically effective amounts of TF and FIXa may be administered into the individual's plasma to determine FVIII:C activity in the 1-0.1 IU/dL range. In some of these embodiments, TF and FIXa are administered into the individual's plasma in picomolar or nanomolar amounts. In some embodiments, the kit is useful for individualized diagnosis of hemophilia patients. In some embodiments, the kit is useful for predicting bleeding risk in patients with congenital and acquired FVIII:C defects. In some embodiments, the kit is useful for monitoring and evaluation of anti-thrombotic regiments. In some embodiments, the diagnosis, monitoring, or evaluation is based on new drugs or combination of drugs.

In various embodiments, the kit is useful for practicing the inventive method of treating, diagnosing, or screening new drugs for hemophilia and anti-thrombosis. The kit is an assemblage of materials or components, including at least one of the inventive compositions. Thus, in some embodiments the kit contains a composition including TF and FIXa, as described above.

The exact nature of the components configured in the inventive kit depends on its intended purpose. For example, some embodiments are configured for the purpose of individualized diagnosis and treatment of hemophilia patients. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to diagnose or treat hemophilia patients. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in the medical field. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing TF and FIXa and monoclonal antibodies or mutant proteins that influence the hemostatic pathway activation. The packaging material generally has an external label which indicates the contents and/or purpose of the kit and/or its components.

There are many techniques readily available in the field for detecting the presence or absence of polypeptides or other biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any numbers of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides may be detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

In accordance with various embodiments herein, an example of a sequence of FVII is illustrated in SEQ ID NO: 1. In accordance with various embodiments herein, examples of various mutants of FVII are illustrated in the following references hereby incorporated by reference: Larsen et al (Journal of Biological Chemistry, 2010); and Pike et al (Proc. Natl. Acad. Sci., Aug. 1999); and Shobe et al (Biochemistry, 1999).

As readily understood by one of skill in the art, various embodiments herein may be also used in conjunction with several diseases and conditions, and the present disclosure is by no means limited to only the field of blood therapeutics or blood complications. Various embodiments disclosed herein may be used, alone or in combination, for the treatment, diagnosis or prognosis of other diseases related to coagulation pathways described herein. For example, in one embodiment, the disclosure herein may be used for the evaluation, prognosis, diagnosis, or treatment of a tumor, cancer, and other related conditions.

Similarly, various methods and devices described herein may also be used in conjunction with additional apparatuses. In one embodiment, the present disclosure provides a method of assessing blood complications and/or coagulation in conjunction with one or more microfluidic devices.

Embodiments of the present disclosure are further described in the following examples. The examples are merely illustrative and do not in any way limit the scope of the invention as claimed.

EXAMPLES

Example 1

Both TF and CP Coagulation Pathways Contribute to FeCl$_3$-Induced Thrombosis

In the conventional view of the coagulation cascade, illustrated in FIG. 1, the extrinsic TF pathway generates limited amounts of thrombin promoting feedback reactions in which the soluble plasma procofactors, FVIII and FV, are activated along with FXI. Activated FXI (FXIa) in turn cleaves FIX to FIXa, which can also be generated by TF-FVIIa. FIXa then amplifies procoagulant protease production through intrinsic tenase (FVIIIa-FIXa) and prothrombinase (FVa-FXa) complexes. This paradigm explains why FVIIa, and not FXII, is pro-hemostatic, as is removal of TFPI control in FVIII deficiency. However, this current paradigm cannot explain why polyanion-dependent FXIIa-mediated activation of FXI is essential in TF-initiated experimental arterial thrombosis.

In various embodiments, the present disclosure addresses this problem. In one embodiment, the disclosure herein confirms through various experiments and results that both TF and CP coagulation pathways contribute to FeCl$_3$-induced thrombosis in the mouse carotid artery by showing that a monoclonal antibody (MoAb) inhibiting 80% of TF-dependent coagulation and one blocking FXI activation by FXII all individually prevented vascular occlusion. In another embodiment, a similar effect was obtained by combining sub-threshold concentrations of the two antibodies, suggesting that both intrinsic and extrinsic pathway concur in generating prothrombotic levels of coagulation proteases in this model. In some experiments, ex vivo experiments with re-calcified human FIX-deficient plasma supplemented with normal platelets, relipidated recombinant TF (rTF) at an individually inactive concentration synergistically enhanced thrombin generation by FIXa. In one embodiment, this finding demonstrated that the observed cooperative function of TF and CP pathways was not the consequence of direct or indirect feed-forward loops activating FIX. Moreover, in normal platelet-rich plasma (PRP), FXIIa or FXIa added with rTF had the same effect as FIXa, demonstrating that CP activation was an upstream pathway for FIXa generation. In some embodiments, TF and CP pathway synergism involved both FVII and FVIII, and low concentrations of TFPI present in plasma were responsible for the suppression of thrombin generation by rTF alone.

Example 2

Coagulation Protease Generation in Reactions with Purified Components

In some embodiments, coagulation protease generation in reactions with purified components was determined. In one embodiment, consistent with results in plasma, rTF produced only minimal FXa and thrombin (FIIa), but in combination with FIXa yielded more than additive amounts of each protease. In some embodiments, the activation of FVIII and FV preceded the burst of thrombin activity and, unexpectedly, was by far more efficient in the presence of rTF than FIXa alone. In various embodiments, these results suggested the possibility that the extrinsic coagulation initiation complex acted as a direct activator of plasma-derived coagulation cofactors prior to significant thrombin generation. In agreement with this concept, rTF caused dose-dependent cofactor activation in the presence of FVIIa and FX in a simplified prothrombin-free system with added lepirudin to inhibit potential trace contamination by thrombin. In some embodiments, FVIII was preferentially activated despite a 4-fold molar excess of FV. In some embodiments, monitoring prothrombin activation in the presence of the thrombin inhibitor, dansylarginine-N-(3-ethyl-1,5-pentanediyl) amide (DAPA), showed that this novel pathway led to assembly of a catalytic prothrombinase complex without contribution by cofactor-converting thrombin feed-back reactions.

In some embodiments, TF-FVIIa alone produced known inactive cofactor fragments smaller than FVIIIa and FVa, but addition of FX yielded properly processed cofactors, indicating that activating cleavages occurred preferentially when FXa was generated during TF-initiated coagulation. FXa inhibition with tick anticoagulant peptide (TAP) reverted the reaction to generating degradation fragments. In some embodiments, nematode anticoagulant protein (NAP) c2, a TFPI-like inhibitor that prevents FX activation by blocking the FVIIa active site, did not generate these fragments. In some embodiments, NAPc2 does not affect the FXa catalytic site. Thus, in some embodiments, in a NAPc2-stabilized TF complex with inactive Ser195Ala mutated FVIIa (iFVIIa) and FXa, only FXa is an active protease. In one embodiment, the TF-iFVIIa-FXa-NAPc2 complex was stable, as shown by the fact that it lacked prothrombinase activity. In one embodiment, this complex could activate FVIII, albeit not FV. In various embodiments, these findings establish the novel concept that cofactor activation is an early event during TF-initiated coagulation, mediated by de novo generated FXa still assembled within the TF-FVIIa-FXa complex.

Example 3

FVIIIa Generation by the TF Pathway Initiation Complex

In some embodiments, FVIIIa generation by the TF pathway initiation complex is a key step in the alternative coagulation paradigm disclosed here. In some embodiments, this concept was verified in reactions concurrently initiated by TF and FXIIa. It was found that pre-activated FVIIIa, but not pro-cofactor FVIII, bypassed the rTF-FVIIa effect on FXa generation after coagulation initiation by FXIIa or FXIa. Moreover, in a mouse model in which concurrent administration of sub-threshold concentrations of anti-TF and anti-FXI MoAbs prevented FeCl$_3$-induced femoral vein thrombosis, infusing FVIIIa—but not FVIII—restored occlusion by a fibrin-rich thrombus. In some embodiments, FVIIIa failed to reverse the antithrombotic effect of a higher, fully inhibitory anti-FXI MoAb dose, establishing that FVIIIa acted only in the CP-dependent synergistic coagulation pathway as disclosed herein. In some embodiments, these findings support the conclusion that FVIIIa is activated in a dynamic in vivo environment by the TF-dependent extrinsic coagulation pathway physiologically regulated by TFPI-mediated feedback inhibition.

Example 4

Consequences of Negative TFPI Regulation

In various embodiments, to elucidate in detail the consequences of negative TFPI regulation, the inventors showed that corn trypsin inhibitor (CTI), which blocks FXIIa, had no effect on TF-initiated thrombin generation unless TFPI was added. In some embodiments, this occurred even when TFPI was at a concentration that, by itself, had minimal effect in the static plasma assay system used. In some embodiments, in experiments performed to explain how FXIIa acquires a role in TF-initiated thrombin generation, it was found that TFPI only partially inhibited FV activation by the extrinsic pathway initiation complex and only at very high concentration. In some embodiments, inhibition of FVIII activation was minimal, as confirmed by FVIIIa activity measurements. In some embodiments, detailed time course analysis revealed that TFPI, although attenuating cofactor activation initially, prevented time-dependent degradation caused by exposure to FXa and, thus, essentially extended the functional cofactor half-life.

In one embodiment, confirming the generation of active FVIIIa, addition of FIXa prevented the time-dependent decrease of FXa activity caused by 40 nM TFPI at a fixed concentration of rTF-FVIIa in reactions without prothrombin. Concordant results were obtained at 8-fold lower TF concentration with correspondingly reduced FXa generation, excluding that a high initial FXa concentration was required for sustained activity. In another embodiment, cleavage of prothrombin (FIT) in the presence the thrombin inhibitor DAPA demonstrated that FVa generated in the presence of TFPI was assembled into an active prothrombinase complex. Thus, in some embodiments, TF-initiated coagulation under TFPI control establishes a direct path to thrombin generation without requiring cofactor activation by feedback reactions, and supports amplified thrombin production dependent on CP generated FIXa in the intrinsic tenase complex. Accordingly, in some embodiments, inhibition of rTF-initiated FXa and thrombin generation by TFPI was markedly diminished in the presence of FIXa.

In various embodiments disclosed herein the preferred cofactor substrate for activation by TF-FVIIa-FXa is FVIII, which plays a key role in hemostasis as an antihemophilic factor. In some embodiments, it was determined that persistent FVIII activation helps explain the reported lower incidence of bleeding complications in rivaroxaban as compared to warfarin treated patients. In one embodiment, at clinically relevant concentrations, rivaroxaban blocked FVa generation by the ternary TF-FVIIa-FXa complex while allowing cleavage into inactive fragments by TF-FVIIa. In another embodiment, rivaroxaban minimally affected FVIII activation. Even at 500 nM rivaroxaban, the peak plasma concentration at full anticoagulant dosage, FVIIIa generation was sustained and supported FIXa-dependent production of functionally meaningful thrombin concentrations when extrinsic coagulation was effectively turned off by TFPI control. Thus, in one embodiment, selectively targeting FXa with rivaroxaban has a built-in safety mechanism that allows for kinetically favored FVIII activation by the nascent product of the extrinsic coagulation initiation complex. As a consequence, in some embodiments, limited thrombin generation occurs that is selectively dependent on intrinsic pathway anti-hemophilic factors and is potentially useful for hemostasis. In various embodiments, the concepts disclosed herein provide new perspectives for developing improved hemostatic and targeted antithrombotic agents as well as evaluating their properties.

Example 5

Reciprocal Interplay Between Coagulation and Host Defense Mechanisms

In various embodiments, it was identified that nascent FXa product in the extrinsic coagulation initiation complex is a TFPI-escaping activator of the plasma cofactor, FVIII, enabling intrinsic pathway dependent thrombin generation. In some embodiments, the present disclosure explain the concurrent role of FXII and TF in developing vascular occlusion, and provide clues to understanding how coagulation initiation may differ in hemostasis and thrombosis. In this regard, in some embodiments, TFPI acts as a master switch primarily designed to control thrombin generation and maintain vascular patency. In some embodiments, in primary hemostasis, blood exposure to abundant TF at wound sites can directly overcome TFPI inhibition permitting initial coagulation protease generation and cofactor amplification mainly through the extrinsic pathway. In other embodiments, overcoming TFPI blockade of extrinsic FXa production may be difficult in endovascular thrombosis, particularly in arteries where abundant TFPI is released by platelet-rich developing thrombi. In some embodiments, TF plays an unanticipated and selective role by directly activating cofactors that prime the intrinsic coagulation pathway for continuing CP-initiated thrombin generation. The same mechanism may operate in pathologic conditions when secondary danger signals triggering the CP pathway, whether released from activated platelets, leukocytes, microbial pathogens or damaged cells, accompany TF induction. In one embodiment, atherothrombosis may be a specific example of such conditions, since endoarterial occlusion is often precipitated by the superposition of inflammation or infections onto TF-exposing vulnerable atherosclerotic plaques. Thus, in various embodiments, the findings reported here has broad significance not only for the contribution of coagulation to thrombosis and its treatment, but also for understanding the reciprocal interplay between coagulation and host defense mechanisms.

Example 6

Hemostatic and Thrombotic Clot Formations are Differentially Regulated.

Under the conventional view (FIG. 1), coagulation depends on feedback activation of plasma pro-cofactors, FVIII and FV, by limited amounts of thrombin (FIIa) initially produced by FXa, which in turn originates from FX activated by the TF-FVIIa complex under negative TFPI control. FIXa generated by TF-FVIIa or FXIa can then amplify clotting through sequential assembly of intrinsic tenase (FVIIIa-FIXa) and prothrombinase (FVa-FXa) complexes producing more FXa and thrombin, respectively. Amplified thrombin production is critical for hemostasis, requiring extrinsic pathway FVIIa, but not contact phase FXIIa; accordingly, removal of TFPI checkpoint control improves hemostasis in hemophilic mice. However, certain experimental thrombosis models depend on contact phase FXIIa activation of FXIa, suggesting that hemostatic and thrombotic clot formation is differentially regulated. In one embodiment, the inventors identified these differences in regulation of hemostatic and thrombotic clot formation.

In one embodiment, intrinsic and extrinsic pathways cooperate in generating coagulation proteases at levels needed to cause thrombosis. To establish this, a mouse carotid artery model was used in which a monoclonal antibody (MoAb) to TF, like an anti-FXI MoAb blocking activation by FXIIa, significantly reduced the frequency of stable vascular occlusion following a lesion induced by 7% $FeCl_3.6H_2O$. Importantly, after a more severe 8% $FeCl_3.6H_2O$ lesion, the two antibodies were no longer effective individually at the concentrations used but markedly inhibited vascular occlusion when combined. This demonstrated that intrinsic and extrinsic pathways cooperate in generating coagulation proteases at levels needed to cause thrombosis. A higher concentration of anti-FXI MoAb also prevented occlusion, in line with genetic evidence implicating the contact pathway as crucial for thrombosis in this experimental model.

In one embodiment, the cooperation of coagulation pathways was examined in vitro by measuring thrombin generation in plasma supplemented with normal platelets (reconstituted PRP). Addition of contact pathway proteases (FXIIa, FXIa, or FIXa) together with TF produced more thrombin than when the proteases or TF were added individually. However, low concentrations of TF alone produced essentially no thrombin when normal plasma contained the FXIIa-directed corn trypsin inhibitor (CTI) to prevent artificial contact pathway activation. Rather, TF synergistically enhanced thrombin production by FIXa in a way that required both FVIIa and FVIII. The same synergy occurred in FIX-deficient plasma, excluding that TF contributed to additional FIX activation by direct or indirect loops and indicating to FVIIIa cofactor generation as the enabling step for FIXa-dependent thrombin generation in the presence of physiological plasma coagulation inhibitors.

Example 7

TF Pathway Provides Functional FVIIIa in Reactions Reconstituted with Purified FVIII, FX, FV, and Prothrombin in which Relipidated TF Provided a Limiting Phospholipid Surface In one embodiment, the TF pathway may provide functional FVIIIa in reactions reconstituted with purified FVIII, FX, FV and prothrombin in which relipidated recombinant TF (rTF) provided a limiting phospholipid surface. Addition of FIXa alone induced low level FVIII and FX activation that was abolished by the thrombin inhibitor dansylarginine N-(3-ethyl-1,5-pentanediyl)amide (DAPA), consistent with the known feedback activation of FVIII by thrombin produced in this system. FVIIa alone produced significantly more FXa and FVIIIa than FIXa alone. Adding FIXa together with FVIIa did not appreciably change FVIIIa formation, but increased the amount of FXa above the sum of that obtained with FVIIa and FIXa individually. These results demonstrate that synergy arises from extrinsic pathway-generated FVIIIa which then complexes with FIXa to enhance protease formation further. Importantly, TF supported cofactor activation in a dose-dependent manner even in the absence of prothrombin and FVIII activation in complete reaction mixtures was reduced, but not abolished by DAPA. However, synergistic FXa production was unchanged in the presence of the thrombin inhibitor or when wild-type prothrombin in the reaction was replaced by the catalytically inactive S195A prothrombin mutant. Thus, on a limited initiating phospholipid surface, direct FVIII activation by the TF-FVIIa complex is sufficient to allow productive assembly of the FIXa-FVIIIa intrinsic tenase complex even in the absence of feedback cofactor activation by thrombin (FIG. 1).

In some embodiments, TFPIα present in plasma and released by activated platelets is the physiological regulator of TF-dependent protease generation and prothrombinase. Accordingly, adding anti-TFPI IgG to recalcified citrated PRP enhanced thrombin generation induced solely by a low TF concentration, but the response to FIXa added together with TF was minimally affected by TFPI blockade. Thus, the newly delineated pathway for FVIIIa generation is not under TFPI control. As expected, FXa produced by TF-FVIIa in the reconstituted system was reduced by >50% by TFPI alone and by >75% by TFPI with protein S (PS) cofactor. In contrast, the FIXa-dependent generation of FXa beyond the amount originating from TF-FVIIa (FXa by FVIIIa-FIXa), a reflection of functional FVIIIa in the reaction, was unaffected by TFPI added alone and only partially in reactions containing PS. In agreement with reduced protease generation, TFPI, TFPI/PS and the physiological inhibitor antithrombin with the pentasaccharide cofactor significantly reduced FVIIIa formation. However, these FXa inhibitors did not prevent FVIIIa generation by TF-FVIIa in the presence of thrombin blockade with DAPA, demonstrating that the novel thrombin-independent functional link between extrinsic and intrinsic coagulation can escape control by endogenous physiologic inhibitors.

In some embodiments, additional experiments showed that, besides FVIIIa, the TF pathway was capable of generating FVa with pro-thrombinase activity in the absence of thrombin feedback activation and evading control by TFPI, consistent with pharmacological evidence implicating FXa in FV activation. Thus, the TF pathway can initiate fibrin formation without the previously assumed thrombin feedback loops of cofactor activation. Because partially active FVa is released by stimulated platelets at vascular injury sites, thrombin-independent FVIIIa formation is likely the key in vivo function of the novel coagulation link disclosed herein. This concept was first verified in a recalcified PRP-based thrombin generation assay initiated by adding TF and FIXa in the presence of CTI to block FXIIa. In some embodiments, a function blocking anti-TF antibody significantly prolonged the lag time and reduced the amount of thrombin produced, but this effect was dose dependently reversed by adding FVIIIa.

Example 8

Figure 7:
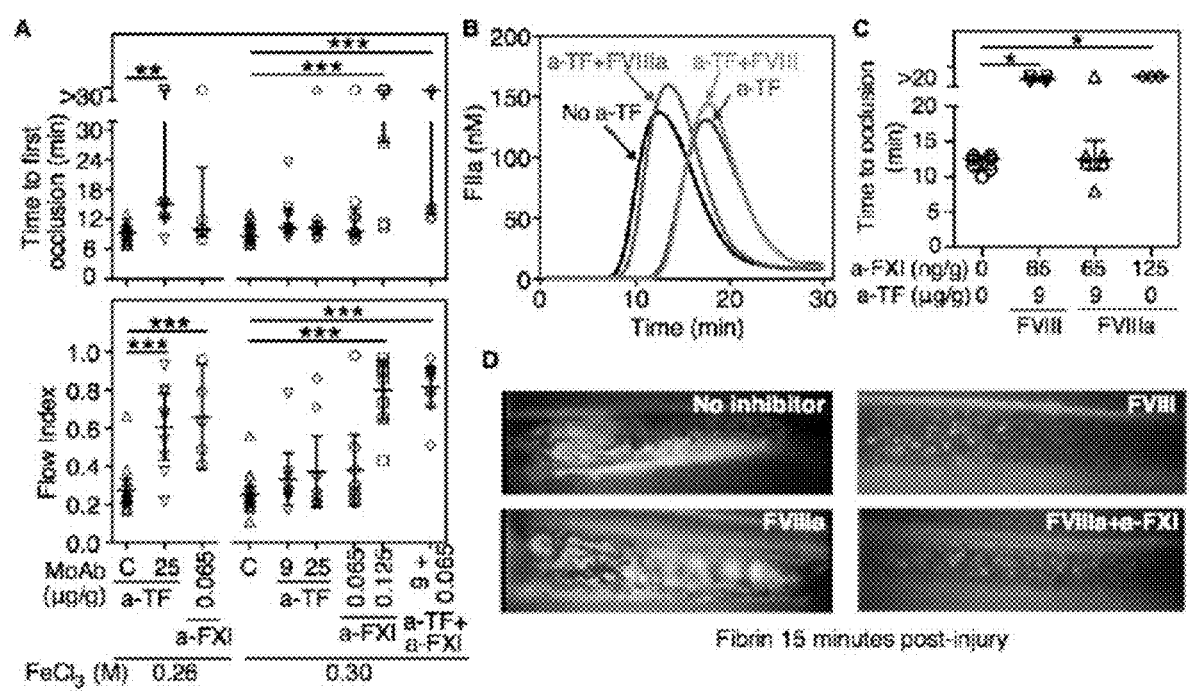
FIG. 7 illustrates, in accordance with embodiments herein, TF contributes to FVIIIa generation in thrombogenesis in vivo. (A) Carotid artery occlusion following a 7% (0.26 M) or 8% (0.3 M) $FeCl_3.6H_2O$ injury in C57BL/6J mice receiving the indicated concentrations of anti-TF 21E10 and anti-FXI 14E11. Time to first occlusion and flow index (n=5-20 in the different groups) were measured. (B) FVIIIa, but not FVIII (both at 40 pM), reversed the anti-TF 5G9 (50 µg/ml) MoAb-induced inhibition of TG initiated in human PRP by TF/FIXa (0.15/20 pM). (C) Femoral vein occlusion following an injury by 4% (0.15 M) $FeCl_3.6H_2O$ in C57BL6J mice (n=3-7 in the different groups) treated with the indicated antibodies and infused prior to injury with FVIII or FVIIIa (1.4 pmole bolus/0.47 pmole/min for 15 min). (D) Representative images of fibrin in the femoral vein showing clotting restoration by FVIIIa but not FVIII infusion following antithrombotic treatment with MoAbs. Top left, no antibody/no FVIII(a) infusion; top right, a-FXI 65 ng/g+a-TF 9 µg/g+FVIII; bottom left, same MoAbs, but+FVIIIa; bottom right, a-FXI 125 ng/g+FVIIIa. Dot plots show median and interquartile range (A, top and C) or mean with 95% CI (A, bottom). Statistical evaluation was performed with the Kruskal-Wallis/Dunn (A, top and C) or ANOVA/Tukey tests (A, bottom). *P<0.05, P<0.01, *P<0.001.

In-Vivo Experiments Evaluating Fibrin Deposition in the Mouse Femoral Vein Following a Ferric Chloride Induced Injury In some embodiments, in-vivo experiments were performed to evaluate fibrin deposition in the mouse femoral vein following a $FeCl_3.6H_2O$-induced injury. As seen in the carotid artery, concurrent administration of anti-TF and anti-FXI MoAb at individually ineffective doses prevented stable occlusion of the vessel and markedly reduced fibrin deposition in the area of the lesion (FIG. 7C, D). In one embodiment, infusion of FVIIIa, but not FVIII, reversed this inhibitory effect, demonstrating that activation of FVIII is a rate limiting step in this model of thrombosis. However, FVIIIa could not restore vascular occlusion in the presence of the fully inhibitory dose of anti-FXI MoAb (FIG. 7D), excluding contributions outside of the TF-dependent link to the intrinsic pathway disclosed here. Thus, FVIII can be activated in vivo by the TF-dependent extrinsic coagulation pathway under physiological TFPI control.

Figure 4:
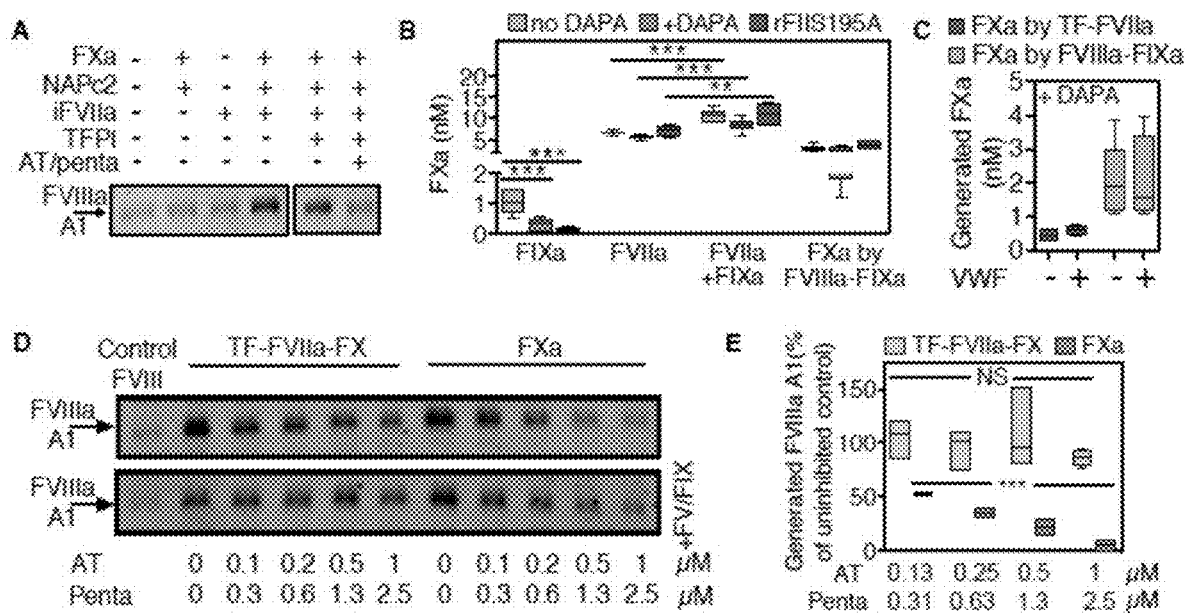
FIG. 4 illustrates, in accordance with embodiments herein, thrombin-independent FVIII activation by nascent FXa from TF-FVIIa. (A) WB analysis (representing 2) of FVIII activation by the stable complex of 50 pM TF (0.37 µM procoagulant phospholipids) with 100 pM inactive iFVIIa, 100 pM FXa, 5 nM NAPc2 incubated for 120 s with 0.7 nM FVIII, 3 nM FV, 200 nM lepirudin, without/with 10 nM TFPIα or 2.5 µM antithrombin (AT)/5 µM pentasaccharide cofactor (penta). (B) FXa generation induced by 10 nM FIXa or 200 pM FVIIa or the two combined added into 50 pM TF, 135 nM FX, 0.7 nM FVIII, 3 nM FV, 1 µM prothrombin, 2.5 mM $CaCl_2$), without (n=7) or with (n=13) 4 µM DAPA and incubated for 180 s at 37° C. In 4 experiments, inactive S195A mutant substituted for WT prothrombin (no DAPA). FXa by FIXa/FVIIIa was calculated by subtracting FXa generated by FVIIa and FIXa individually from that by FVIIa/FIXa added together. (C). FXa generation by TF-FVIIa or FIXa-FVIIIa after 180 seconds in reactions including 500 pM FVIIa, 400 pM TF, 10 nM FIXa, 135 nM FX, 0.7 nM FVIII, 3 nM FV, 1 µM prothrombin, 40 nM TFPIα, 4 µM DAPA, 2.5 mM $CaCl_2$), without (n=5) or with (n=4) 18 nM VWF. (D) WB analysis (representing 2) of FVIIIa generation by pre-activated or de novo generated FXa and its inhibition by increasing concentrations of AT/penta. Reactions (37° C.) initiated by 200 pM FXa or 20 pM FVIIa with 50 nM FX into mixtures of 400 pM TF, 0.7 nM FVIII, 200 nM lepirudin without (top, incubation 60 s) or with (bottom, incubation 120 s) 3 nM FV/50 nM FIX. (E) Quantification (relative to non-inhibited control) of FVIIIa generated as in D (bottom) calibrated with known FVIIIa quantities (n=6-8 by nascent FXa, 4-6 by pre-formed FXa). Results (B, C, E) are shown $25^{th}$-$75^{th}$ as 25 percentile bars with min to max whiskers and line at the median. Differences were evaluated by ANOVA followed by Tukey's (B) or Dunnett's (E) test; data in (B) were transformed as y=log 10 y before analysis. P<0.01; *P<0.001.

In one embodiment, these results illustrated that TF-mediated FVIII activation escaping TFPI inhibition was a function of product FXa still assembled with the extrinsic TF-FVIIa complex. This was determined by exploiting the properties of nematode anticoagulant protein (NAP) c2, a TFPI-like inhibitor that blocks the FVIIa active site preventing FX activation. Because NAPc2 has no effect on the FXa catalytic site, a NAPc2-stabilized complex of FXa, TF and catalytically inactive Ser195Ala FVIIa (iFVIIa) mutant was formed. In this complex, FXa was the only active protease. Remarkably, FXa in this complex, but not free FXa at the same concentration, generated FVIIIa (FIG. 4A). Consistent with a TFPI-like complex formation of NAPc2, TFPI did not inhibit FVIII activation by the stabilized complex, but antithrombin in complex with pentasaccharide (FIG. 4A) or other FXa inhibitors decreased FVIIIa formation, further confirming that FVIIIa was generated by FXa. These findings support the novel concept that cofactor activation is an early event during TF-initiated coagulation, mediated by de novo generated FXa possibly still assembled within the TF-FVIIa-FXa complex.

In one embodiment, nascent product FXa escapes inhibition by rivaroxaban and apixaban, two different pharmacologic small molecule inhibitors of FXa. This is similar to FXa escaping the physiological TFPI checkpoint. Persistent FVIII activation preserving hemostasis is likely to be the reason why the antithrombotic efficacy of FXa inhibitors is associated with a relatively low risk of bleeding complications. Rivaroxaban and apixaban had comparable potency in blocking purified FXa amidolytic and prothrombinase activities, with IC50 ~two-fold higher for the latter. At therapeutic concentrations, rivaroxaban and apixaban inhibited FVIII activation by free FXa on the TF phospholipid surface or by the stabilized TF/iFVIIa/FXa/NAPc2 complex by ~90%. In contrast, the IC50 was at least 1 order of magnitude higher when FVIII was activated by FXa generated de novo by TF-FVIIa. Inefficient inhibition of FVIIIa generation by nascent FXa was reflected in the preservation of FVIII-dependent thrombin production by TF-FVIIa in the presence of FIXa under TFPI inhibitory control at each of the rivaroxaban and apixaban concentrations tested.

Example 9

Physiological Relevance

In one embodiment, to assess the physiological relevance, TF-induced thrombin generation in recalcified PRP containing CTI to block contact phase FXIIa. Rivaroxaban and apixaban inhibited thrombin production with ~3-fold difference in dose response. Importantly, residual thrombin generation in the presence of these FXa inhibitors was remarkably sensitive to a function-blocking anti-FVIII antibody. In contrast, thrombin generation in the absence or presence of the pharmacologic FXa antagonists was not affected by an anti-FXI antibody that interrupted the thrombin feed-back loop operating through FXIa or other FXIa effects. These results confirm that, in the presence of all the physiological blood coagulation inhibitors, a measurable component of TF-initiated thrombin generation depends on FVIIIa and escapes, at least partially, direct FXa inhibitors in clinical use. Antibody blockade of TFPI increased the rivaroxaban and apixaban concentration required for an anticoagulant effect on thrombin generation in PRP. However, regardless of whether TFPI was functional, FVIII-dependent amplification of thrombin generation was preserved at clinically relevant inhibitory concentrations of the two drugs. Thus, even with reduced TFPI control, as may occur in thrombogenic environments, kinetically favored FVIII activation by nascent product FXa may contribute to hemostasis through this link with the intrinsic coagulation pathway.

Example 10

Novel Diagnostic Approaches

In one embodiment, to substantiate this concept with new diagnostic approaches, the inventors measured the volume of platelet aggregates and fibrin deposited onto surfaces coated with collagen or TF following perfusion of recalcified citrated blood from normal controls and patients treated with rivaroxaban or warfarin. The latter were regularly monitored by International Normalized Ratio (INR) test; the former received no laboratory monitoring in accordance with treatment guidelines. On a surface coated with a low TF concentration, a function blocking anti-FVIII MoAb reduced fibrin deposition in normal blood, but adding anti-TFPI IgG alleviated this inhibitory effect on both fibrin and platelet deposition. Increasing TF in the coating solution abolished the FVIII-dependence and TFPI regulation in normal blood, demonstrating that this condition mimicked a thrombogenic surface escaping TFPI checkpoint control. In contrast, on a surface coated with saturating collagen, FVIII inhibition had no effect on platelet aggregation—as immobilized collagen is a strong platelet agonist—but caused a significant decrease of fibrin volume that was unchanged in the presence of anti-TFPI IgG.

In one embodiment, this approach may be used to measure thrombus formation in control and patient blood perfused over a high density TF surface, where thrombin generation is driven by the extrinsic coagulation pathway independent of TFPI control, and on a high density collagen surface where clotting is driven by the intrinsic pathway. Fibrin deposition was significantly reduced on both surfaces in blood from warfarin treated patients. In rivaroxaban-treated patients, however, fibrin deposition was as low as in warfarin treated patients on the TF surface but, not significantly decreased as compared to untreated controls on collagen. Thus, both treatments are effective in inhibiting thrombogenesis directly driven by the extrinsic TF pathway. In contrast, drugs targeting FXa instead of affecting all vitamin K-dependent proteases selectively preserve FVIII-dependent fibrin formation that may support hemostasis at sites critical for bleeding in patients receiving anticoagulant therapy. In one embodiment, the experimental results disclosed herein further illustrate the novel coagulation link (FIG. 1) in which nascent FXa produced through the extrinsic TF-FVIIa coagulation initiation complex provides feed-forward activation of cofactors, in particular anti-hemophilic FVIII. In contrast to the canonical feedback mechanism dependent on initially generated thrombin, FVIII activation by nascent FXa escapes the TFPI checkpoint and is preserved in the presence of FXa targeted anticoagulants. In some embodiments, this mechanism of FVIII activation, specifically integrated within the TF-initiated coagulation pathway, may operate in a coordinated fashion with FIXa protease generation by TF-FVIIa that also escapes inhibitory control by physiological anticoagulants. In some embodiments, the novel link between extrinsic and intrinsic coagulation pathways also explains the hitherto poorly rationalized but experimentally evident contribution of contact phase FXII to TF-dependent fibrin formation in animal models of thrombosis. In some embodiments, these results provide an unexpected explanation for how, in stark contrast to traditional oral anticoagulants, specific targeting of FXa can preserve residual thrombin and fibrin generation through the anti-hemophilic intrinsic pathway. Thus, the concepts uncovered here helps individualize the definition of thrombotic and bleeding risk for patients treated with new oral anticoagulants, as well as lead to refined approaches for inhibiting thrombosis while preserving sufficient hemostatic function.

Example 11

FXa Inhibitors Preserve FVIII-Dependent Thrombin and Fibrin Formation

Figure 2:
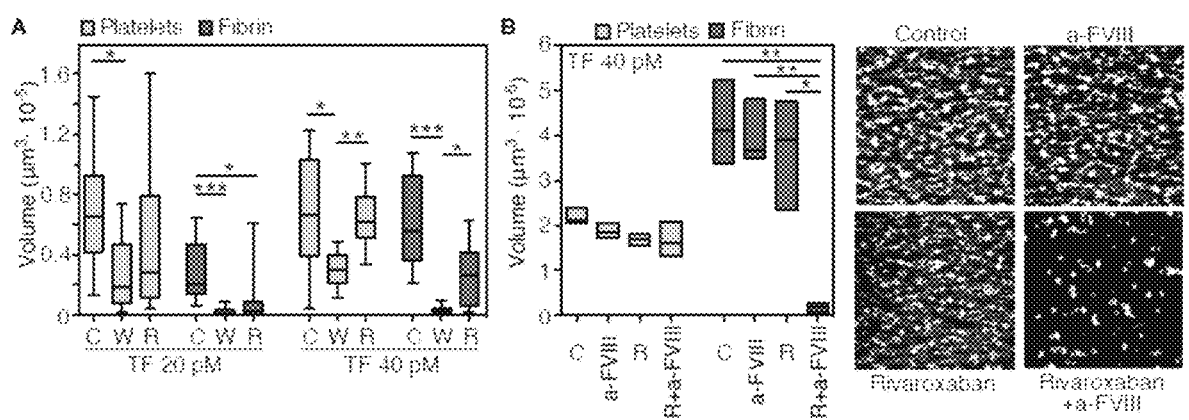
FIG. 2 illustrates, in accordance with embodiments herein, the effect of coagulation inhibitors on thrombus formation in flowing blood exposed to TF. (A) Platelet and fibrin deposition onto rTF immobilized using the indicated coating solution concentrations. Recalcified (1.29 mM $Ca^{2+}$) citrated blood from controls (C; n=9) and patients treated with warfarin (W; n=12, average INR 2.6) or rivaroxaban (R; n=10, 312 nM average plasma concentration 2 hours after drug intake) was perfused for 5 min at the wall shear rate of 300 s1. (B) Left: Normal blood without (C) or with 300 nM rivaroxaban (R) and/or anti-FVIII MoAb (ESH-8, 40 µg/ml) was perfused over immobilized rTF for 2 min as in (A); n=3 for all conditions. Note that, owing to different microscopes used, the quantified fields in (B) were 4.65 times larger than in (A). Right: Representative confocal images (side=312 µm) with superimposed signals from the green (platelets and leukocytes) and red (fibrin) fluorescence channels; co-localization yields yellow. Results are shown as 25th-75th percentile bars with min to max whiskers (A) or (when n≤3) as min to max bars (B); a horizontal line indicates the median. Statistical evaluation was performed with the Kruskal-Wallis/Dunn (A) or ANOVA/Tukey (B) tests. *P<0.05, P≤0.01, *P<0.001.

In one embodiment, the inventors have found that FXa inhibitors preserve FVIII-dependent thrombin and fibrin formation. In one embodiment, the inventors compared how the FXa-selective anticoagulant, rivaroxaban, and the vitamin K antagonist, warfarin, influence thrombogenesis by measuring fibrin formation with platelet aggregates in blood from treated individuals perfused over immobilized relipidated recombinant TF (rTF). The volume of deposited fibrin was markedly smaller in patients receiving anticoagulant drugs than untreated controls, but it was significantly greater in rivaroxaban than warfarin-treated patients when the rTF concentration on the surface increased (FIG. 2A). Rivaroxaban, added to normal blood in vitro at the average plasma concentration measured in treated patients two hours after drug intake, reduced fibrin volume partially, but nearly completely in the presence of an anti-FVIII monoclonal antibody (MoAb) that by itself produced modest inhibition (FIG. 2B). While prior studies had observed a limited inhibition by protease-specific anti-coagulants in thrombin generation (TG) assays, these data showed that selective targeting of FXa distinctly preserved TF-initiated thrombin generation through the intrinsic coagulation pathway under control of coagulation inhibitors in blood. Because there were no endothelial cells in the experiments, the results also indicated that rivaroxaban preserved hemostasis independently of interactions involving blood and the vessel wall.

Figure 3:
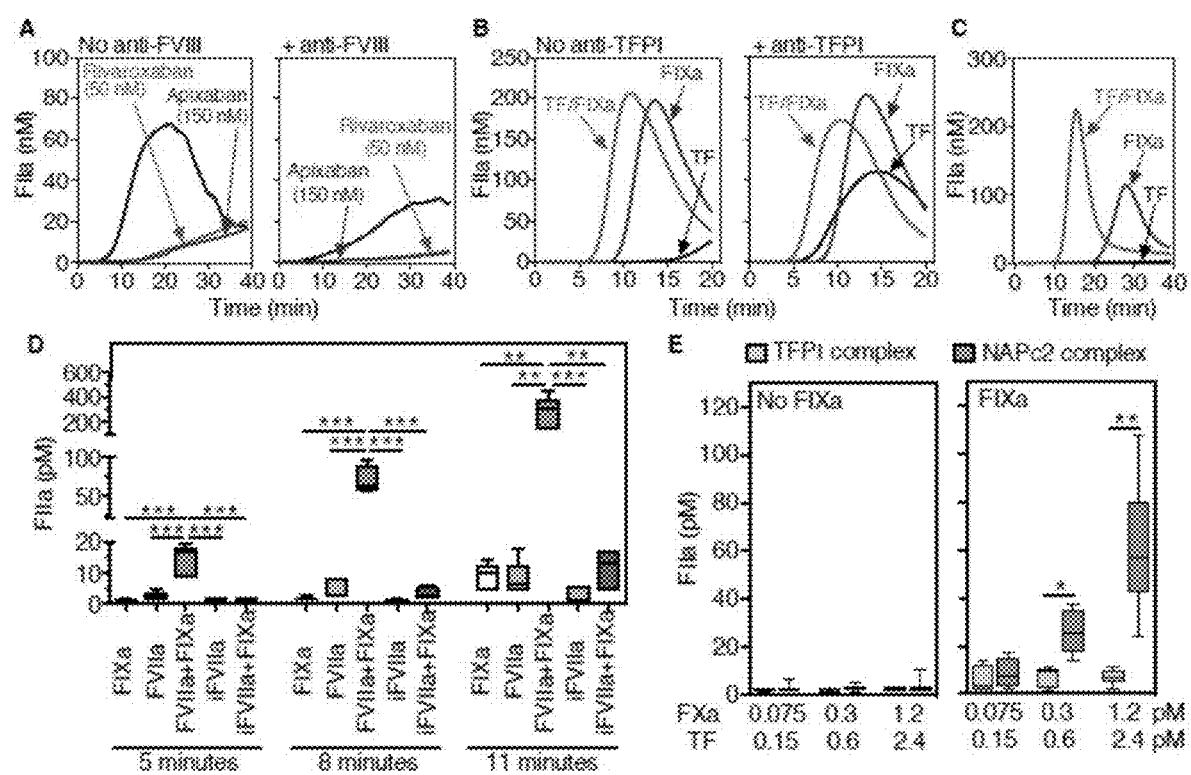
FIG. 3 illustrates, in accordance with embodiments herein, amplification of intrinsic pathway TG by subthreshold TF-FVIIa. (A) TG (representing 2) induced by 0.6 pM TF in recalcified citrated PRP (180×$10^3$ platelets/pi) containing 30 µg/ml CTI without or with rivaroxaban or apixaban and anti-FVIII MoAb (ESH-8, 40 µg/ml). (B) TG (representing 3) induced by 0.15 pM rTF or/and 20 pM FIXa added into recalcified citrated PRP with 30 µg/ml CTI and with 40 µg/ml rabbit non-immune (left) or anti-TFPI IgG (right). (C) TG (representing 2) induced by 0.15 pM rTF with 50 µg/ml CTI in FIX-deficient plasma reconstituted with 180×$10^3$ normal platelets/µl. (D) High sensitivity assay of TG induced by 0.15 pM rTF without/with 20 pM FIXa in FVII-deficient PRP, with 30 µg/ml CTI, reconstituted or not with 400 pM WT FVIIa or S195A inactive mutant (iFVIIa) and incubated for 5 (n=2-5), 8 (n=2-5) or 11 (n=3) min at 37° C. (E) High sensitivity assay of TG induced by pre-incubated (2 min, 37° C.) stable complexes formed with 10 nM TF, 10 nM iFVIIa, 5 nM FXa, 40 nM TFPI or NAPc2 and 2.5 mM $CaCl_2$). Complexes, without/with 10 pM FIXa, were added at the indicated TF and FXa concentrations into FVII-deficient plasma (with CTI) reconstituted with normal platelets, and incubated for 8 min at 37° C. (n=3-5). Results (D, E) are shown as 25th-$75^{th}$ percentile bars with min to max whiskers and a line at the median. Differences were evaluated by the ANOVA/Tukey test after transformation of the data as y=$log_{10}$ y. *P<0.05, P<0.01, *P<0.001.

To confirm these findings, TG was measured in platelet-rich plasma (PRP) containing corn trypsin inhibitor (CTI) to block FXI activation by contact phase FXIIa, which has no role in hemostasis. At the concentrations used, CTI has no reported effects on coagulation proteases downstream of FXIIa. Two distinct FXa antagonists, rivaroxaban and apixaban, inhibited TF-induced TG, and the residual TG in the presence of inhibitors were greatly diminished by additional blockade of FVIII activity (FIG. 3A). Moreover, the marginal TG response triggered by a low rTF concentration increased substantially after blocking TFPI with a specific antibody, showing that TG by threshold concentrations of TF was regulated by plasma and/or platelet TFPI (FIG. 3B). Although low TF failed to induce measurable early TG, it enhanced the effect of FIXa even without TFPI inhibition (FIG. 3B) and in FIX deficient PRP (FIG. 3C), excluding that the observed effect was caused by TF-dependent loops generating additional FIXa.

In one embodiment, using a sensitive thrombin substrate in a discontinuous TG assay, it was found that TF with FVIIa wild-type (WT)—but not with the active site mutant FVIIa S195A (iFVIIa)—amplified FIXa-induced TG in FVII-deficient plasma reconstituted with normal platelets even when initial thrombin generation was <10 pM in 5 min (FIG. 3D). In another embodiment, FIXa added with iFVIIa produced similar low levels of thrombin, but no TG burst as seen with active FVIIa. In one embodiment TF-FVIIa, despite TFPI control in PRP, enhanced TG by FIXa independently of thrombin. In order to exclude any influence on TG by unrecognized activities of the TFPI-inhibited complex of TF-FVIIa-FXa—perhaps caused by the formulation of the rTF preparation—a functionally inhibited TF complex preformed with inactive FVIIa S195A, FXa, and TFPI, was tested. FXa was efficiently inhibited in this complex that could not induce TG or amplify FIXa-dependent TG in FVII-deficient plasma (FIG. 3E, left). In contrast, a similar complex in which TFPI was replaced by the nematode anticoagulant protein (NAP) c2 still failed to induce TG by itself, but markedly enhanced FIXa-induced TG when added at TF concentrations similar to those used for triggering TG in PRP (FIG. 3E, right). Since NAPc2, unlike TFPI, inhibits TF-FVIIa in FXa-dependent manner without affecting FXa catalytic function, these data illustrated that nascent FXa, while still associated with TF-FVIIa, is the primary FVIII activator in the presence of physiologic plasma coagulation factors and inhibitors.

Example 12

Thrombin-Independent FVIII Activation by TF-FVIIa with Nascent FXa

In some embodiments, the present disclosure relates to thrombin-independent FVIII activation by TF-FVIIa with nascent FXa. In various embodiments, FVIII activation with purified components and rTF as the primary phospholipid surface was studied. In one embodiment, the NAPc2-stabilized pre-formed TF-FVIIa S195A complex with FXa as the only active protease activated efficiently FVIII (FIG. 4A). This TFPI-like complex was not inhibited by TFPI, but FXa in this complex was still accessible for other macromolecular inhibitors, such as antithrombin (AT) with the pentasaccharide cofactor (penta), which prevented FVIII activation (FIG. 4A). In a reconstituted coagulation reaction containing purified cofactors (FV and FVIII) and protease zymogens (FX, prothrombin), coagulation initiation by FIXa led to a limited FXa production that, consistent with FVIII activation by thrombin-feedback, was inhibited by dansylarginine N-(3-ethyl-1,5-pentanediyl)amide (DAPA) or when the inactive mutant S195A substituted for normal prothrombin (FIG. 4B). In some embodiments, absence of active thrombin had no effect on FXa generation by TF-FVIIa (FIG. 4B). In some embodiments, TF-FVIIa and FIXa combined yielded more FXa than the sum of the individual reactions and the additional FXa production was unaffected by thrombin blockade (FIG. 4B). In one embodiment, this illustrated that TF-FVIIa with nascent FXa can prime additional FXa production by an active complex of FIXa with newly generated FVIIIa. Consistent with the results in the plasma TG assays, thrombin-independent generation of FVIII activity by the TF initiation complex was unaffected by the presence of VWF (FIG. 4C).

Using the same phospholipid surface containing TF, the inventors compared FVIII activation by either 200 pM pre-activated FXa or 20 pM FVIIa/50 nM FX promoting de novo FXa generation by TF-FVIIa (FIG. 4D). Without added inhibitors, FVIII activation by nascent or pre-activated FXa was comparable in the absence (top panel) or presence (bottom panel) of the alternative zymogen substrate, FIX, and cofactor, FV. However, adding AT and pentasaccharide cofactor to the reaction caused a considerably greater dose-dependent inhibition of FVIIIa generation by pre-activated than nascent FXa (FIG. 4D, E). Thus, although preformed FXa in complex with TF-FVIIa was susceptible to inhibition by AT (FIG. 4A), de novo generated FXa escaped this inhibitory check point, consistent with FVIII activation being a rapid and preferred immediate reaction of TF initiated coagulation.

Example 13

Intrinsic Pathway Activation by TF is Sufficient for TG and Fibrin Formation Under Flow In some embodiments, intrinsic pathway activation by TF is sufficient for TG and fibrin formation under flow. In one embodiment, two FVIIa mutants were identified—T99Y and E154A—which retained catalytic activity for cleavage of FX but had markedly reduced substrate turnover rates. Unlike FVIIa WT, the two mutants could not sustain FXa generation after an initial burst in a phospholipid-free assay (FIG. 5A) or with phospholipid-reconstituted TF (FIG. 5B). Despite markedly decreased FXa generation, mutant and wild-type TF-FVIIa complexes supported comparable FVIII activation requiring presence of FX in the reaction (FIG. 5C). In one embodiment, TFPIα, which can be present in plasma at variable concentration due to release from platelets, did not appreciably inhibit FVIII activation by FVIIa WT or mutants, even when added at the supra-physiological concentration of 10 nM (FIG. 5D). In sharp contrast to FVIII, the FVIIa mutants in complex with TF and presence of FX failed to activate FV; and generation of FVa with FVIIa WT was blocked by TFPIα (FIG. 5D). Thus, in one embodiment, TFPI regulated FV activation. Additional control experiments provided no evidence that the TFPIα cofactor protein S enhanced TFPI inhibition of FVIII activation by TF-FVIIa with nascent FXa.

In some embodiments, both FVIIa mutants with impaired FXa generation supported FVIIIa-dependent FXa production by added FIXa (FIG. 5E). However, when zymogen FIX was added instead, only the FVIIa exosite mutant E154A, but not the FIX activation-deficient T99Y, fully supported formation of a functional FVIIIa-FIXa intrinsic tenase complex (FIG. 5E). Thus, besides the known ability to generate FIXa, the TF initiation complex directly activates the antihemophilic FVIII cofactor enabling intrinsic pathway coagulation before inhibitory control by TFPIα.

In some embodiments, using the identified FVIIa mutants, the inventors verified the validity of this conclusion in the presence of plasma inhibitors and platelets. Wild-type and mutant FVIIa E154A added to FVII-deficient plasma supplemented with normal washed platelets produced comparable levels of thrombin, while FVIIa T99Y was less efficient (FIG. 5F, left). Inhibiting FVIIIa generation essentially blocked TG by the two mutants, while WT FVIIa yielded residual TG (FIG. 5F, middle), consistent with the selective defect of the FVIIa mutants in triggering FXa and thus thrombin generation directly. In some embodiments, blocking FXIa activity had a modest effect on TG by FVIIa E154A as compared to WT, while it markedly reduced TG by FVIIa T99Y (FIG. 5F, right). This result demonstrated that activation of both FVIII and FIX are essential for TF-initiated intrinsic coagulation. That the mutant FVIIa E154A, with limited direct FXa generation, was comparable to FVIIa WT in supporting TF initiation of the intrinsic pathway further illustrates that thrombin feedback has a limited role in FVIII activation during TF-triggered coagulation.

Figure 6:
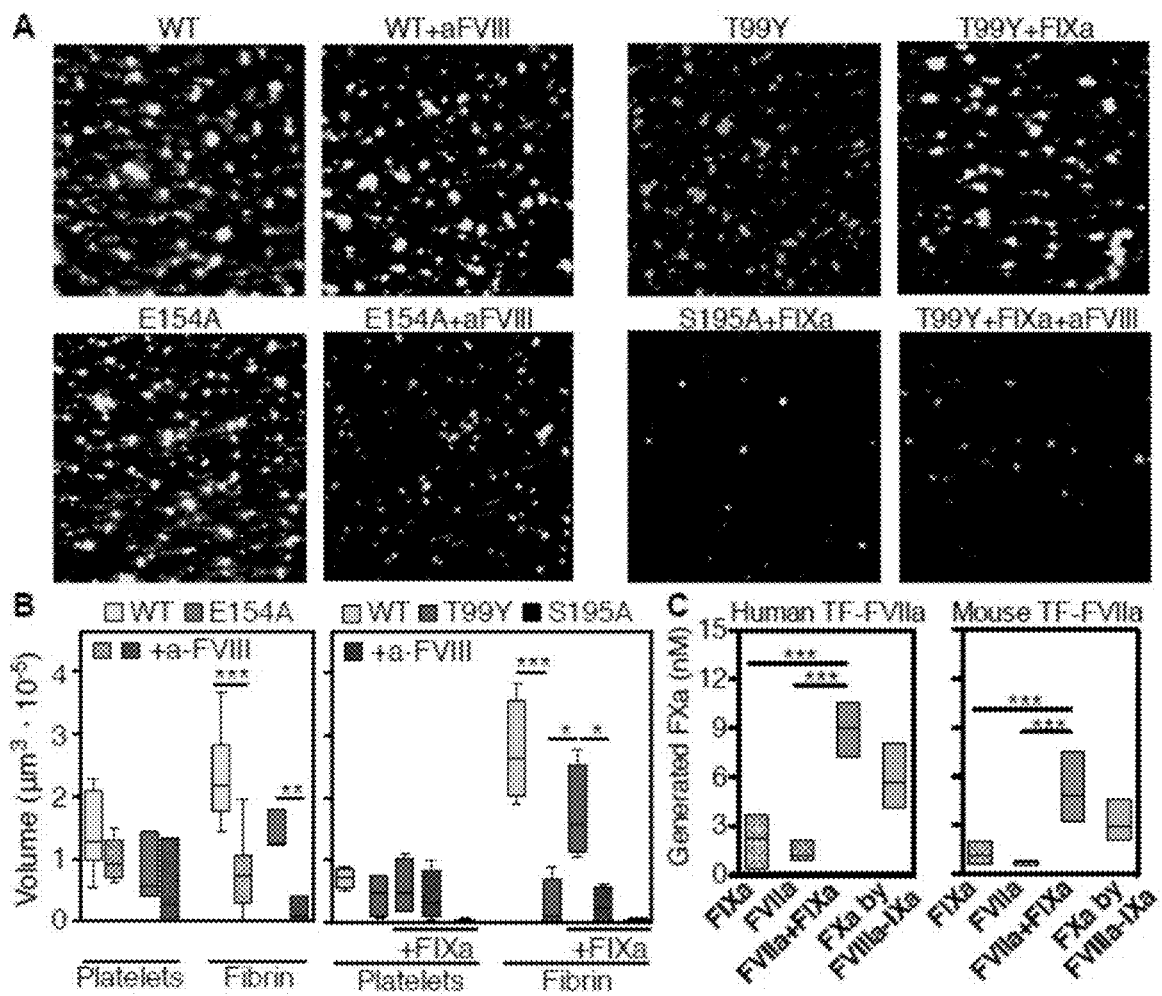
FIG. 6 illustrates, in accordance with embodiments herein, FVIIIa-dependent thrombus formation is induced by the TF coagulation initiation complex in flowing blood ex vivo. (A) Normal washed type O blood cells were resuspended to the original volume with FVII-deficient citrated PPP and supplemented with 200 pM WT or mutant FVIIa without or with addition of the anti-FVIII MoAb C5 (25 µg/ml), followed by recalcification (1.29 mM $Ca^{2+}$) and perfusion for 3.5 min at 300 $s^{-1}$ wall shear rate. The effect of adding FIXa (20 pM) to blood reconstituted with FVIIa T99Y mutant was also evaluated. Representative confocal images are shown with superimposed green (platelet aggregates and leukocytes) and red (fibrin) fluorescence channels. Image side=312 µm. (B) Quantification of the volume of platelet aggregates and fibrin deposited onto the TF-coated surface (n=4-6 for the different conditions). (C) Generation of functional FVIIIa on procoagulant microparticles (MP) from mouse macrophages expressing knocked-in human TF (left) or endogenous mouse TF (right). FVIIIa generation was induced by adding MP suspensions into reactions containing 10 nM species-matched human or mouse FVIIa and 0.7 nM FVIII, 3 nM FV, 135 nM FX, 200 nM lepirudin, without or with 2 nM FIXa. FX activation by FVIIIa-IXa was calculated from the total and individual reaction rates. Results are shown as $25^{th}$-$75^{th}$ percentile bars with min to max whiskers (B) or min to max bars (C, n=2-3) with a line at the median. Differences were evaluated by the ANOVA/Tukey test (*P<0.05, P<0.01, *P<0.001).

In one embodiment, the thrombogenic activity of FVIIa mutants with reduced free FXa turnover in flowing blood experiments ex vivo was studied. By limiting the surface TF concentration such that fibrin deposition depended on FVIIIa when the wall shear rate was 300 s−1, it was found that FVIIa with the E154A mutation, but not T99Y, supported mildly reduced to similar thrombus formation as WT FVIIa when reconstituted into FVII-deficient blood (FIG. 6A). Addition of 20 pM FIXa to blood containing FVIIa T99Y, but not the same concentration of catalytically inactive FVIIa S195A, restored FVIII-dependent fibrin formation to a level comparable to that seen with FVIIa E154A (FIG. 6B). This confirmed that the TF-FVIIa complex with nascent FXa directly generated FVIIIa with intrinsic tenase activity and the potential to be beneficial for hemostasis in low TF environments.

In some embodiments, the novel pathway described herein was evaluated in mouse models. In one embodiment, mouse TF-FVIIa supported the generation of functional FVIIIa in vitro. In one embodiment, pro-coagulant microparticles from mouse macrophages were generated. Then, this natural source of TF was analyzed for FVIII activation in a reaction with purified components. Incorporation of either knock-in human or endogenous mouse TF into microparticles in the presence of species-matched FVIIa stimulated FIXa-dependent FXa generation as seen with phospholipid-reconstituted recombinant TF (FIG. 6C). Thus, the direct FVIII activation pathway supported by TF-FVIIa with nascent FXa occurs with biologically relevant sources of TF and is conserved in the mouse.

Example 14

TF Contributes to FVIII Activation In Vivo

In some embodiments of the present disclosure, TF contributes to FVIII activation in vivo. Next, it was evaluated whether TF function contributed to generating FVIII activity in vivo in a model of ferric chloride-induced thrombosis. In agreement with the involvement of both contact phase and TF coagulation pathways in thrombosis, independent administration of MoAbs blocking TF function (such as 21E10) or FXI activation by FXIIa (such as, anti-FXI 14E11) significantly reduced mouse carotid artery occlusion after a lesion caused by 7% (0.26 M) FeCl$_3$.6H$_2$O (FIG. 7A). The same concentrations of MoAbs were individually ineffective after a more severe 8% (0.3 M) ferric chloride lesion, but markedly antithrombotic when combined, illustrating convergence of extrinsic and intrinsic coagulation in vivo. Higher concentrations of anti-FXI MoAb alone also prevented arterial occlusion, consistent with an essential role of FIX activation by FXIIa-FXIa in this model. In vitro, anti-TF MoAb inhibition of synergistic TG initiated by combined TF and FIXa in PRP was reversed by adding FVIIIa but not FVIII (FIG. 7B), confirming a predominant role for TF in FVIII activation in plasma. Similarly, FVIIIa but not FVIII reversed the inhibition of ferric chloride-induced femoral vein occlusion by combined sub-threshold doses of anti-TF and anti-FXI MoAbs. However, FVIIIa had no influence on inhibition of FXIIa/FXIa-mediated FIXa generation by full-dose anti-FXI MoAb in the absence of anti-TF (FIG. 7C, D), excluding that TF-FVIIa or alternative pathways could generate FIXa in sufficient amounts to utilize exogenously provided FVIIIa for triggering thrombosis. The finding that FVIIIa selectively reversed TF blockade illustrates that promoting FVIII activation is a key role of the TF-FVIIa extrinsic coagulation pathway in vivo.

Example 15

TF Initiation of the Intrinsic Pathway Escapes Pharmacological FXa Blockade

Figure 8:
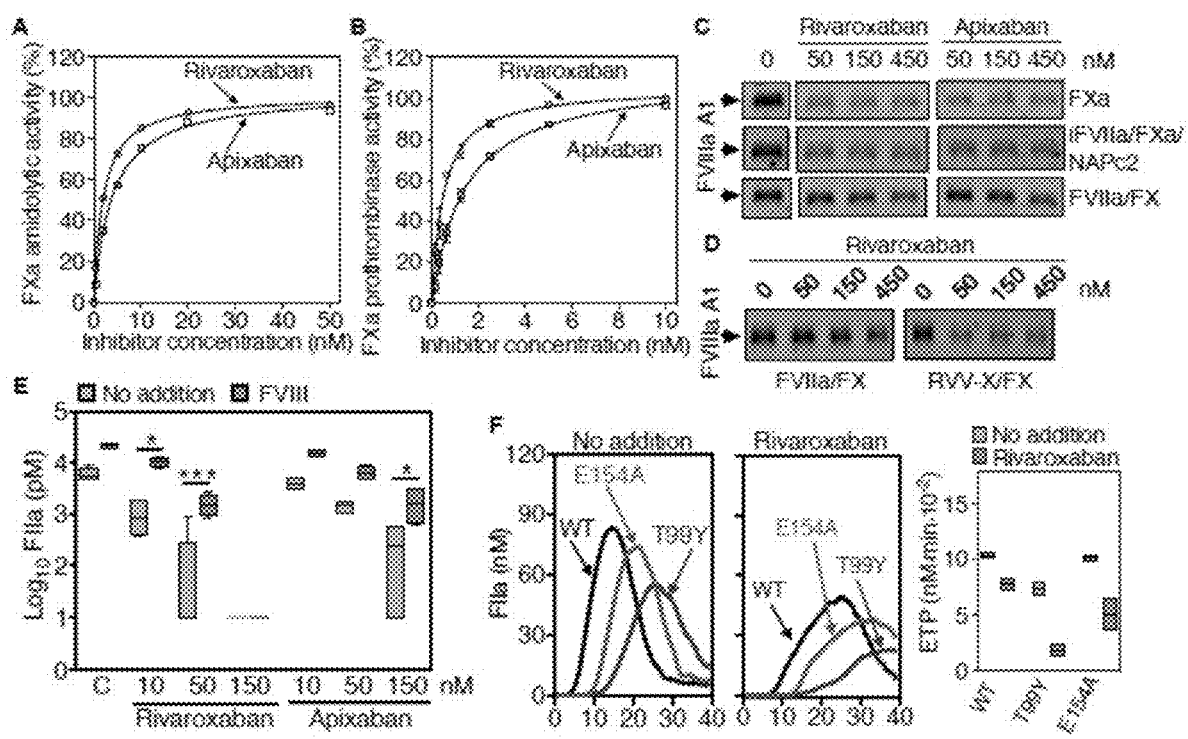
FIG. 8 illustrates, in accordance with embodiments herein, direct TF initiation of intrinsic coagulation escapes pharmacological FXa inhibitors. (A) Inhibition of FXa amidolytic activity by rivaroxaban and apixaban. FXa (1 nM) was incubated with rivaroxaban or apixaban (n=3 each) at the indicated concentrations and residual FXa activity was measured with the chromogenic substrate S-2765 (360 µM) at 37° C. for calculation of % inhibition (mean±SEM). IC50 values (nM) were: Rivaroxaban 1.9±0.09; apixaban 3.56±0.32. (B) Inhibition of FXa (50 pM) prothrombinase activity after incubation with the indicated concentrations of rivaroxaban or apixaban (n=3 each) for 4 min at 37° C. in reactions containing 50 pM rTF as the phospholipid surface, 3 nM FVa and 1 µM prothrombin. Thrombin was quantified with a fluorogenic substrate for calculation of % inhibition. IC50 values (nM) were: Rivaroxaban 0.43±0.06; apixaban 1.08±0.11 (C) WB analysis of FVIIIa generation and its inhibition by increasing concentrations of rivaroxaban or apixaban. Reactions were initiated by 100 pM FXa with 50 pM rTF as the phospholipid surface (top); or the preformed complex of 50 pM TF, 100 pM iFVIIa, 100 pM FXa, 5 nM NAPc2 (middle); or 50 pM TF/200 pM FVIIa/135 nM FX (bottom) in mixtures of 0.7 nM FVIII, 3 nM FV, 200 nM lepirudin, 10 nM TFPI, and 2.5 mM $CaCl_2$ incubated for 120 s at 37° C. (D) WB analysis of rivaroxaban effect on FVIII activation by FXa generated by Russel's viper venom (RVV) FX activator (13.5 pM) or TF-FVIIa—generating 1.25 and 1.23 nM FXa, respectively—after 120 s incubation of reactions as in (C). (E) Inhibition of TG induced by 200 pM FVIIa, 10 nM FIXa 50 pM rTF, 135 nM FX, 3 nM FV, 1 µM prothrombin, 10 nM TFPIα without or with 0.7 nM FVIII for 240 s at 37° C. (n=3-4). (F) Thrombograms showing rivaroxaban (left, no addition; middle, 50 nM) inhibition of TG initiated by 2.5 pM TF in FVII-deficient PRP reconstituted with 400 pM WT or mutant FVIIa T99Y or E154A. Endogenous thrombin potential (ETP, right) was calculated from the area under the TG curve (n=2). Results in (E) and (F) are shown as 25th-75th percentile bars with min to max whiskers or min to max bars (when n<3) with a line at the median. Differences were evaluated with the ANOVA/Tukey test (performed after log 10 transformation of the data shown in E); *P<0.05, ***P<0.001.

In some embodiments disclosed herein, TF initiation of the intrinsic pathway escapes pharmacological FXa blockade. In one embodiment, the inventors evaluated whether FXa inhibitors in clinical use (such as rivaroxaban and apixaban) preserve FVIII activation by the TF coagulation initiation complex. Both inhibitors comparably blocked FXa amidolytic and prothrombinase activities (FIG. 8A, B). At therapeutic concentrations, between 50-450 nM, both inhibited by ~90% FVIII activation by pre-activated FXa either free or in a NAPc2-stabilized complex with TFFVIIa S195A (iFVIIa), but only marginally reduced FVIII activation by nascent FXa generated by TFFVIIa (FIG. 8C). The latter was a specific effect, since rivaroxaban inhibited FVIII activation by FXa that was de novo generated to equivalent levels using the TF-independent Russel's viper venom (RVV) FX activator (FIG. 8D). Moreover, both rivaroxaban and apixaban at therapeutic doses inhibited TG initiated by TF alone in reactions containing FIXa without FVIII, but significantly more TG was preserved when FVIII was added (FIG. 8E). The inability of both small molecule and macromolecular inhibitors to block FVIIIa generation by the TF initiation complex identifies the anti-hemophilic cofactor FVIII as a preferred substrate for nascent FXa. In additional studies with the identified FVIIa mutants, it was found that TG in the presence of rivaroxaban was only slightly delayed with FVIIa E154A as compared to WT (FIG. 8F), demonstrating that intrinsic pathway activation in the presence of therapeutic concentrations of the FXa inhibitor was preserved by the mutant capable of generating FIXa. In contrast, significantly decreased TG with the FIX activation-deficient FVIIa T99Y relative to E154A and WT indicated that FXa-targeted anticoagulants could inhibit the thrombin feedback loop leading to FXIa-dependent FIXa generation.

In various embodiments, the inventors screened a panel of anti-FVIIa MoAbs for interference with TF-mediated intrinsic pathway activation. In some embodiments, inhibitory antibodies, such as MoAb 3G12, prevented FVIII activation by the TF initiation complex. In other embodiments, MoAb 12C7, known to react with a defined epitope close to the macromolecular substrate-binding exosite, was non-inhibitory in this reaction (FIG. 9A). This antibody limited FXa turnover mediated by FVIIa WT and required FIXa for amplified FXa generation in the presence of TF pathway-generated FVIIIa (FIG. 9B). Unlike the inhibitory anti-FVIIa MoAb 3G12, MoAb 12C7 preserved TG in normal PRP. However, FVIII-dependent TG in the presence of MoAb 12C7 became highly susceptible to inhibition by anti-FXI antibody (FIG. 9C). These results illustrated that MoAb 12C7 inhibits FIXa generation by TF-FVIIa, mimicking the properties of FVIIa T99Y. In addition, low rivaroxaban concentrations produced a more pronounced inhibition of TG in the presence of MoAb 12C7 (FIG. 9D), confirming that FXa targeted anticoagulants inhibit thrombin-FXI feedback loops while selectively preserving direct FVIII and FIX activation by the TF initiation complex.

Example 16

Coagulation Pathway

In various embodiments, the present disclosure delineate a novel function of the extrinsic coagulation initiation complex, namely providing selective feed-forward activation of the anti-hemophilic cofactor, FVIII, independently of thrombin feed-back loops (FIG. 1). This specific reaction of nascent FXa escapes control by physiologic coagulation inhibitors, TFPIα and AT, as well as by pharmacologic anticoagulants targeting FXa. In some embodiments, together with the TF-FVIIa capacity to activate the anti-hemophilic protease, FIX, direct FVIIIa generation constitutes a pathway to FVIIIa-FIXa intrinsic tenase activity fully integrated within TF-initiated coagulation.

In some embodiments, as revealed experimentally using FVIIa mutants and a complex stabilized with nematode NAPc2 protein, the TF-FVIIa-FXa complex selectively generates FVIIIa cofactor for intrinsic tenase, but not FVa cofactor for prothrombinase that requires FXa undocking from TF-FVIIa exposing free FXa to inhibitory control. Therefore, the newly identified TF-FVIIa-FXa function allows for accumulation of active pro-hemostatic anti-hemophilic cofactor without increasing prothrombotic FVa. In one embodiment, this can explain why, with comparable anti-thrombotic potency, targeted FXa and thrombin inhibitors have a lesser impact on hemostasis than vitamin K antagonists that reduce FIXa availability and, consequently, impair the direct activation of intrinsic tenase driven by the TF pathway leading to hemostatic fibrin generation. In one embodiment, such a mechanism is independent of FXI activity and may thus preserve hemostasis also in the context of recently validated anti-thrombotic strategies targeting FXI.

In some embodiments, the cofactor selectivity illustrates distinct functional properties of FXa in complex with or released from TF-FVIIa. While coagulation cofactor-enzyme complexes are typically geared towards efficient substrate turnover for rapid thrombin generation, throughout evolution the TF initiation complex appears to have preserved mechanisms favoring its stability. FX interacts with TF-FVIIa through an extended interface that is minimally affected by the zymogen to enzyme transition of the substrate. In this interface, FVIIa residue E154, which is conserved across various species, transmits conformational changes upon substrate docking to the active site of the protease, which may regulate subsequent product release. Elimination of this conformational switch was sufficient to segregate macromolecular substrate activation and product turnover by TF-FVIIa. Thus, mutant FVIIa E154A enabled recognition of the function of direct FVIII activation by nascent FXa associated with TF-FVIIa as well as the contribution of this novel pathway activating intrinsic coagulation to thrombin generation and thrombogenesis in platelet-rich plasma and whole blood under flow.

In some embodiments, stability of the TF coagulation initiation complex likely represents the evolutionary advantage of preserving key signaling roles of TF-FVIIa-FXa that link coagulation activation and innate immunity. In line with efficient FVIII activation, FVIIa T99Y is fully functional in mediating TF-FVIIa-FXa activation of protease activated receptor (PAR) 2. Moreover, as seen for FVIIIa generation, resistance to functional inhibition by TFPIα is also an important feature of PAR signaling induced by TFFVIIa-FXa in endothelial cells. This signaling complex is additionally stabilized by recruitment of the FXa binding partner, endothelial protein C receptor (EPCR), in mouse and man. Dendritic cells have a key innate immune signaling role for the TF-FVIIa-FXa-EPCR complex, where it is essential for toll like receptor 4 induction of responses involving TIR domain containing adapter inducing interferon-β/TIR domain-containing adapter molecule 1 (TRIF/TICAM-1). In some embodiments, negative regulation of this pathway by the alternative EPCR ligand, activated protein C, utilizes the canonical anticoagulant cofactor functions of FV and protein S. Thus, these and other nontraditional functions of the coagulation system likely utilize the same mechanistic features that simultaneously serve diverse roles in immunity, hemostasis and injury repair.

While target-selective oral anticoagulants are safe without close therapeutic monitoring, as required for vitamin K antagonists, the new concepts and diagnostic approaches disclosed here would individualize the definition of thrombotic and bleeding risk for patients treated with these drugs. The present disclosure provides the biochemical bases for defining distinct roles of TF in supporting hemostasis or contributing to thrombosis. Indeed, through direct feed forward activation of the intrinsic pathway protected from physiologic inhibitors, TF can sustain FXa and thrombin generation for hemostasis while being susceptible to TFPI control limiting thrombosis risk caused by excessive direct generation of FXa and FVa prothrombinase cofactor. The selectivity of FXa oral anticoagulants in targeting prothrombotic coagulation pathways versus hemostatic favorable FVIII activation can be evaluated by new diagnostic tests based on the reagents described here. In one embodiment, this may lead to selectively assessing the effects of recently developed and future new anticoagulants on the dual roles of TF in hemostasis and thrombosis. In some embodiments, the novel concepts on coagulation presented here may have implications for the development and evaluation of new hemostatic agents, capable of avoiding adverse thrombotic complications in patients with underlying vascular pathologies while at the same time providing protection from severe bleeding complications.

Example 17

Materials

Control mouse and rabbit IgG, quinacrine-HCl (mepacrine) and apyrase were from Sigma-Aldrich (St. Louis, MO). Human prothrombin (FII), thrombin (FIIa), FV, FVa, FIX, FIXa, FX, FXa, antithrombin (AT), corn trypsin inhibitor (CTI), dansylarginine N-(3-ethyl-1,5-pentanediyl)amide (DAPA), Russel's viper venom FX activator and anti-human FV monoclonal antibody (MoAb) AHV-5146 (binding to residues 306-506 in the FV A1-A2 domain) were from Haematologic Technologies (Essex Junction, VT). Rivaroxaban and apixaban were from Santa Cruz Biotechnology (Santa Cruz, CA). Bovine serum albumin (BSA) was from Calbiochem (San Diego, CA); relipidated human recombinant tissue factor (rTF; Dade Innovin) from Siemens Healthcare Diagnostics (Deerfield, IL). Since the manufacturer no longer provides protein and phospholipid (PL) concentration of Innovin, all used batches were calibrated against a lot (#53691) of known TF concentration (13.9 nM) using a FXa generation assay that included various rTF concentrations to obtain a dose-response curve, 100 pM FVIIa, 135 nM FX, 2.5 mM $CaCl_2$, incubated for 60 s at 37° C. Procoagulant PL concentration was determined by prothrombinase activity in a reaction that included rTF, 12.5 pM FXa, 10 nM FVa, 1 µM prothrombin, 2.5 mM $CaCl_2$, incubated for 60 s at 37° C. By calibration with PL vesicles consisting of 80% phosphatidylcholine (PC) and 20% phosphatidylserine (PS) mol/mol (Avanti Polar Lipids, Alabaster, AL)—sonicated in 0.15 M NaCl, 10 mM 4-(2-hydroxyethyl) piperazine-1-ethanesulfonic acid (HEPES), pH 7.4—the reference rTF solution contained 101.4 µM PL. Human protein S (PS) was from Enzyme Research Laboratories (South Bend, IN); the AT-binding pentasaccharide of heparin (fondaparinux sodium; Arixtra) from Glaxo-SmithKline S.p.A. (Verona, Italy); sheep anti-human prothrombin antibody from Affinity Biologicals (Ancaster, ON); nematode anticoagulant protein c2 (NAPc2) from Corvas International (San Diego, CA). The inhibitory anti-human FVIII MoAbs were ESH-8 and 8D4—from Sekisui Diagnostics (Stamford, CT) and Dr. Marc Jacquemin (Leuven, Belgium), respectively—and C5, previously described (56). FVIII was a gift from Bayer Healthcare (Berkeley, CA). Recombinant TFPI, human FVIIa, inactive FVIIa S195A (chymotrypsin numbering; iFVIIa), mutant FVIIa T99Y and FVIIa E154A, soluble TF extracellular domain (sTF1-218) and inactive prothrombin S195A were produced and characterized as known in the art. FVIIIa was prepared by incubating 190 nM FVIII with 19 nM thrombin and 5 mM $CaCl_2$ for 30 sec at 37° C., followed by 36 nM lepirudin (recombinant [Leu1-Thr2]-63-desulfohirudin; Refludan, Bayer Corp, Pittsburgh, PA) to neutralize thrombin activity.

Example 18

Blood Perfusion Experiments

Glass coverslips treated with 0.2 mg/ml poly-L-lysine for 6 h at 37° C. were coated with rTF for 18-20 hours at 37° C. or 2.5 mg/ml acid-insoluble type I collagen for 2 hours at 22-25° C. Then they were rinsed with pH 7.4 buffered-saline, assembled in a rectangular flow chamber with a 125 µm-high silicon gasket and positioned on a confocal microscope stage for analysis. Venous blood for testing was collected into final 10.9 mM trisodium citrate using a plastic syringe for normal volunteers or Vacutainer tubes (Becton Dickinson, Buccinasco, Milan) for patients and controls. Before perfusion at a flow rate yielding an initial wall shear rate of 300 $s^{-1}$ maintained with a syringe pump (Harvard Apparatus, Holliston, MA), $CaCl_2$ was added to obtain 1.29 mM In the blood of patients—potentially hypercoagulable—and related controls, lepirudin (50 nM) was also added to neutralize thrombin possibly generated before testing. In preliminary experiments, this amount of lepirudin had a limited effect on the deposited fibrin volume in the flow chamber. For experiments with WT and mutant FVIIa, cells from group O citrated blood, containing 50 µg/ml CTI and 10 U/ml (ADPase activity) apyrase, were washed free of plasma by sequential centrifugation steps at 1500 g for 7 min. After the first, plasma was replaced with an equal volume of calcium-free Tyrode buffer, pH 6.5, with 5 U/ml apyrase; then with buffer and 1.25 U/ml apyrase; and finally with human FVII deficient plasma (George King Bio-Medical, Overland Park, KS) up to the original blood volume. Cell count results in reconstituted and native blood were within 90%. Experiments in Milan (Italy) were performed with a Leica TCS SP5 microscope and HCX PL APO 63x/1.40 NA oil immersion objective (Leica Microsystems GmbH, Wetzlar, Germany); in La Jolla (California) with a Zeiss Axiovert 135M/LSM 410 and Plan-Apochromat 40x/1.40 NA oil immersion objective (Carl Zeiss AG, Oberkochen, Germany).

Platelets adhering and aggregating onto the surface were visualized by adding quinacrine-HCl (mepacrine; 10 µg/ml; Sigma-Aldrich) to blood. Deposited fibrin was visualized with Alexa Fluor 546-labeled (Invitrogen) mouse monoclonal IgG (50 µg/ml) specific for the B chain of mouse and human fibrin (HB-8545; ATCC). Blood was perfused for 3-5 min at 37° C. with a syringe pump (Harvard Apparatus Inc.) at a flow rate yielding an initial (in the unobstructed flow path) wall shear rate of 300 $s^{-1}$. This was followed by buffer (DMEM) for 2 minutes to facilitate fibrin quantification by confocal z section analysis using a Zeiss Axiovert 135M/LSM 410 microscope (Carl Zeiss) and Plan-Apochromat x63/1.40 NA oil immersion objective. Image analysis was performed with NIH ImageJ64. Deposited fibrin volume was measured from confocal sections collected at 4 preset positions in the flow chamber. Total volume of deposited platelets and fibrin was calculated from the sum of the respective area coverage per section multiplied by the z interval (2 μm). All studies involving human subjects were conducted following institutionally approved protocols.

Example 19

TG Analysis in Human Native or Reconstituted PRP

TG in PRP or reconstituted PRP was evaluated as known to those skilled in the art. Native PRP was prepared from blood collected into final 12.9 mM trisodium citrate by centrifugation at 250 g for 10 min at 25° C. The platelet count was adjusted to $180 \times 10^3/\mu l$ by dilution with homologous PPP obtained by centrifuging PRP for 10 min at 1,500 g. CTI was added at 30-50 μg/ml depending on calibrated potency as assessed by FXIIa inhibition. Reconstituted PRP was prepared with washed platelets prepared from normal PRP by adding ⅕th volume of acidcitrate-dextrose (71 mM citric acid, 85 mM trisodium citrate, and 111 mM dextrose, pH 4.5) and 5 U/ml apyrase; following centrifugation at 1,500 g for 10 minutes at 25° C., the platelet pellet was resuspended into PPP lacking FVII (George King Bio-Medical) or FIX (Haematologic Technologies) to give a final platelet count of 180·103/μl. PRP was mixed with varying concentrations of rTF and/or 20 pM FIXa in 96-well microtiter plates. The reaction was started by adding 18 mM $CaCl_2$ with 360 μM of the thrombin substrate benzyloxycarbonyl-glycyl-glycyl-L-arginine coupled to the fluorogenic group 7-amido-4-methylcoumarin (Gly-Gly-Arg-AMC; Bachem Americas, Torrance, CA). Fluorescence was measured continuously at 37° C. for up to 40 min in a spectrofluorometer (355/460 nm excitation/emission). The rate of fluorescence intensity increase as a function of time (dF/dt) was calculated with Turbo Delphi 2006 (Borland Software Corporation, Austin, TX) and converted to thrombin-equivalent concentration (nM) using a calibration curve. The endogenous thrombin potential (ETP) of samples, i.e. total generated thrombin activity, was determined from the area under the TG curve. When specified, TG was measured with a discontinuous 2-stage assay with a detection limit of 5 pM. For this, TG was induced by 0.15 pM rTF and 18 mM $CaCl_2$ in reconstituted FVII-deficient PRP including 30 μg/ml CTI with 400 pM WT FVIIa or iFVIIa without or with 20 pM FIXa. After incubation for up to 11 min at 37° C., reactions were terminated by adding 20 mM EDTA and generated thrombin was measured using the highly sensitive thrombin substrate H-D-CHA-Ala-Arg-AMC·2AcOH (Pefafluor TH, Pentapharm, Basel, Switzerland) at 50 μM concentration. In other experiments, TG was induced by TFiFVIIa-FXa-TFPI or TF-iFVIIa-FXa-NAPc2. These stable complexes were pre-formed by incubating 5 nM FXa, 10 nM TF, 10 nM iFVIIa and 40 nM TFPI or NAPc2 in the presence of 2.5 mM $CaCl_2$ for 2 min at 37° C. Complexes were added into FVII-deficient PRP, followed by incubation for 8 min at 37° C.

Example 20

Analysis of FVIII and FV Activation by Western Blot (WB)

Coagulation reaction products were separated by reducing sodium dodecyl sulfate-polyacrylamide gel electrophoresis (SDS-PAGE), except for the analysis of FVIII activation in the presence of anti-FVIIa MoAbs that was performed under non-reducing conditions. After transfer to a polyvinylidene fluoride membrane, blots were probed with MoAb C5, biotinylated or not (0.5 μg/ml), for FVIII activation; MoAb AHV-5146 (1 μg/ml) for FV. Quantitative infrared detection of FVIIIa and FVa was obtained with IRDye 800CW-conjugated anti-mouse IgG or streptavidin followed by analysis with the Odyssey infrared imager (Li-COR, Lincoln, NE). Concentrations were calculated by calibration with known quantities of FVIIIa and FVa.

Example 21

Coagulation Activation in Reactions with Purified Components

The synthetic reaction mixtures comprised 0.7 nM FVIII, 3 nM FV, 135 nM FX, 1 μM prothrombin in 50 mM Tris-buffered saline, pH 7.4, with 0.1% BSA. Coagulation inhibitors TFPI, PS, AT/pentasaccharide, NAPc2, and direct FXa inhibitors (such as, rivaroxaban and apixaban) were added at the indicated concentrations. Reactions to prevent thrombin effects were carried out in the presence of 200 nM lepirudin or 4 μM DAPA. Reactions were initiated by adding 0.6 to 400 pM rTF, 200 to 500 pM FVIIa or/and 10 nM FIXa, followed by 2.5 mM $CaCl_2$ and incubation at 37° C. for the indicated times. 10 mM EDTA was then added to quench the reaction. Generation of FXa, FIIa and thrombin were evaluated by measuring amidolytic activity toward the chromogenic substrate S-2765 (180 μM; N-α-benzyloxycarbonyl-D-arginyl-L-glycyl-L-arginine-p-nitroaniline; DiaPharma, West Chester, OH) and the fluorogenic substrate Z-Gly-Gly-Arg-AMC (360 μM) respectively.

Contact phase generation of FXa was studied by adding FXIIa (500 pM) without or with 0.6 pM TF/200 pM FVIIa into reactions including 0.2 μg/ml DS, 100 nM HMWK, 30 nM FXI, 50 μM ZnCl2, 90 nM FIX, 135 nM FX, 700 pM FVIII or FVIIIa, 18 nM VWF, 20 μM PL and 2.5 mM $CaCl_2$. Generation of FIIa in the presence of DAPA and activation of FVIII and FV were determined by Western blotting (WB) as described below. The extrinsic pathway activation complex (TF-FVIIa-FXa) was stabilized by mixing NAPc2 (5 or 40 nM) with iFVIIa (100 or 200 pM), FXa (100 or 200 pM) and rTF (50 or 400 pM). Prothrombinase activity of FXa was measured in reactions containing 10 nM FVa, 1 μM FII and 2.5 mM $CaCl_2$ at 37° C. for the indicated incubation times. The anti-FXa activity of rivaroxaban and apixaban was measured as inhibition of amidolytic or prothrombinase activities. To measure inhibition of FXa amidolytic activity, 1 nM FXa was mixed with varying inhibitor concentrations and the chromogenic substrate S-2765 (360 μM); (OD) at 405 nm was measured continuously at 37° C. for up to 10 min in a microplate reader. The amidolytic activity of FXa was determined from the slope of the OD/min curve calculated using GraphPad Prism (GraphPad Software, La Jolla, CA). To measure inhibition of FXa prothrombinase activity, 50 pM FXa was incubated with 50 pM rTF, 3 nM FVa and 1 μM FII at 37° C. After 4 min, the reaction was quenched with 10 mM EDTA and generated FIIa was determined using the fluorogenic substrate Z-GGR-AMC. The half maximal inhibitory concentration (IC50) of both inhibitors was determined using GraphPad Prism.

To block thrombin activity, reactions were carried out in the presence of 4 μM DAPA or with inactive S195A replacing WT prothrombin. In some experiments, prothrombin was omitted from reactions and 200 nM lepirudin was added to inactivate potentially contaminating thrombin. The effect of rivaroxaban and apixaban on FVIII activation by de novo generated FXa was also examined by adding Russel's viper venom FX activator (13.5 pM) into reactions containing 50 pM rTF as phospholipid surface, but no FVIIa, and 10 nM TFPI, followed by WB of FVIIIa. A stable complex with FXa as the only active protease was prepared with 50 pM rTF, 100 pM FVIIa-S195A (iFVIIa), 100 pM FXa and 5 nM NAPc2 incubated for 120 s at 37° C. FVIII activation by this complex was examined in reactions including FVIII, FV and lepirudin incubated for 120 s.

Substrate turnover by TF-FVIIa was evaluated by monitoring FXa generation in reactions without phospholipids including 10 nM FVIIa, 2 µM sTF1-218, and 1 µM FX. Inhibition of FXa amidolytic activity by rivaroxaban or apixaban was measured by mixing 1 nM FXa with varying inhibitor concentrations and the chromogenic substrate S-2765 (360 µM); OD at 405 nm was measured continuously at 37° C. for up to 10 min in a microplate reader. The amidolytic activity of FXa was determined from the slope of the OD change as a function of time calculated using GraphPad Prism (GraphPad Software, La Jolla, CA). Inhibition of prothrombinase activity was measured by incubating 50 pM FXa with 50 pM rTF as the phospholipid surface, 3 nM FVa and 1 µM prothrombin at 37° C.; after 240 s, the reaction was quenched with 10 mM EDTA and generated thrombin was quantified using the fluorogenic substrate Z-GGR-AMC (360 µM). The half maximal inhibitory concentration (IC50) for each substance was determined by fitting the corresponding inhibitory dose-response curve using GraphPad Prism.

Example 22

Ferric Chloride-Induced Thrombosis in Mice

All animal procedures complied with the Guide for Care and Use of Laboratory Animals and were approved by the IACUC of the Scripps Research Institute. Vascular injury was induced in C57BL/6J mice using a single 0.8 µl drop of 7% (0.26 M) or 8% (0.30 M) FeCl3.6H2O on the carotid artery for 3 min; or a 0.4 µl 4% (0.15 M) drop for 1 min on the femoral vein, followed by rinsing.

Carotid artery thrombosis was described by two parameters: 1) Time to first occlusion, defined as the time at which blood flow in the artery dropped to 0.1 ml/min or less; and 2) flow index (FI), defined as the ratio between the total blood volume flowing through the artery in 30 min post injury (integrated from the volumetric blood flow sampled every 1 s) and the corresponding volume in the uninjured artery (calculated from the flow measured over 1 min before injury); thus, FI=1 indicates no change in flow. Venous thrombosis was assessed by epifluorescence video microscopy-based evaluation of platelet aggregate and fibrin formation in real time in an injured vessel. Washed platelets labeled with calcein red-orange ($2\times10^6$/g body weight) were injected into the mouse jugular vein before establishing the vascular lesion. Fibrin was visualized by injecting fluorescein isothiocyanate-labeled anti-fibrin antibody (0.8 µg/g body weight) with the labeled platelet suspension. Thrombus size was assessed quantitatively by measuring integrated pixel density on selected images of fluorescent platelet aggregates and fibrin using Image J software.

Antibodies against TF or FXI were administered by bolus injection of the indicated quantities into the catheterized jugular vein. FVIII and FVIIIa were administered by a bolus injection (1.4 pmoles) followed by maintenance with continuous infusion at the rate of 0.47 pmoles/min for 15 min. Time to first occlusion after initiation of injury is that required for a decrease of blood flow to less than 10% of the value initially measured in the uninjured artery. Flow index is the ratio between the total blood volume flowing through the artery after the injury (integration of flow measured in ml/min and sampled every second for 30 minutes) and the expected flow in the uninjured artery (calculated from the flow measured during 1 minute before injury multiplied by 30).

Example 23

Statistical Analysis

For statistical analyses, GraphPad Prism (GraphPad Software, Inc, La Jolla, CA) and XLSTAT (Addinsoft, Paris, France) were used. Variance homogeneity was evaluated with the Levene's median and Bartlett's tests. For multiple comparisons among groups, one-way ANOVA was used, after y=log 10 y data transformation when necessary for homoscedasticity, followed by the Tukey's or Dunnett's tests; or the Kruskal-Wallis nonparametric test followed by the Dunn's tests. In some embodiments, the data shown in this disclosure are mean with standard error of the mean (SEM) of the indicated number of experimental values.

Example 24

Thrombin Generation in Human Platelet-Rich Plasma (PRP) or Reconstituted PRP

PRP was prepared from blood collected into trisodium citrate (final concentration 0.0129 M) by centrifugation for at 250 g for 10 min at 25° C.; the platelet count was adjusted at 180.103 per µl by diluting with homologous platelet-poor plasma (PPP) obtained by centrifuging PRP for an additional 10 min at 1,500 g. When indicated, CTI was added at 30 to 50 µg/ml depending on calibrated potency measured by FXIIa inhibition. Reconstituted PRP was prepared by adding normal washed platelets into PPP (without or with CTI) lacking FVII, FVIII (both from George King Bio-Medical, Overland Park, KS) or FIX (Haematologic Technologies). TFIIa generation in PRP was measured as described by Hemker et al. 53 µl of PRP was mixed in 96-well microtiter plates with 15 µl of a solution containing rTF and/or one of the intrinsic coagulation pathway proteases—FXIIa, FXIa or FIXa—to achieve the indicated final concentrations. Antibodies or inhibitors were also added at this point at the concentration indicated for each specific case. The reaction was started by adding between 15 and 20 µl of 100 mM $CaCl_2$ and 2 mM fluorogenic substrate, benzyloxycarbonyl-glycyl-glycyl-L-arginine-7-amido-4-methylcoumarin (Gly-Gly-Arg-AMC; Bachem Americas, Torrance, CA). FIIa generation in PPP was also examined in the presence of inhibitory anti-TFPI polyclonal antibody or control rabbit IgG (20 µg/ml) with added phospholipid vesicles (5 µM). The relative fluorescence intensity developing during the reaction was measured continuously at 37° C. for up to 40 min in a spectrofluorometer (excitation 355 nm and emission 460 nm). Fluorescence intensity velocity increase as a function of time (dF/dt) was calculated using the program Turbo Delphi 2006 (Borland Software Corporation, Austin, TX) and converted to thrombin-equivalent concentration (nM) using a calibration curve. FIIa generation was described by determining the lag time (time until 3 nM thrombin was formed), and the endogenous thrombin potential (ETP; total generated thrombin activity determined from the area under the thrombin generation time-course curve).

Example 25

Western Blotting Analysis of FII, FVIII and FV Activation

Samples for Western blotting (WB) analysis were first subjected to polyacrylamide gel electrophoresis (PAGE) in the presence of sodium dodecyl sulfate (SDS) and 512 nM 2-mercaptoethanol. After transfer to a polyvinylidene fluoride membrane, protein bands were revealed with anti-human FII sheep polyclonal antibody (0.5 µg/ml), anti-FVIII MoAb C5 (0.5 µg/ml) or anti-FV MoAb AHV-5146 (2 µg/ml). Activation fragments of FII were detected by chemiluminescence using biotinylated anti-sheep IgG (Thermo Fisher Scientific, Rockford, IL) and horseradish peroxidase (HRP)-streptavidin conjugate (Life Technologies, Grand Island, NY). For quantitative infrared (IR) detection of FVIIIa and FVa, IRDye 800CW-conjugated anti-mouse IgG (Li-COR, Lincoln, NE) was used, followed by analysis with the Odyssey infrared imager (Li-COR). Values were derived from calibration curves obtained with known quantities of FVIIIa and FVa.

Example 26

Unique Function of FXa

In some embodiments, the disclosure provided herein provides two important lines of evidence demonstrating a unique function of FXa derived from TF-FVIIa in supporting cofactor VIII activation. In some embodiments, in the first line of evidence is that TF-FVIIa can generate FXa that in turn generates FVIIIa without significant effect of the physiologic TFPI anticoagulant or pharmacologic direct FXa inhibitors such as rivaroxaban. However, Russel's viper venom FX activator (RVV-X), which is a heterotrimeric metalloproteinase with a mammalian ADAM-like heavy chain and two lectin-like light chains, cannot generate FXa. In some embodiments, even in the presence of TFPI and rivaroxaban combined—the latter at concentration as high as 450 nM—there was substantial FVIIIa generation when TF-mediated coagulation was initiated by FVIIa but substantial inhibition when the initiator was RVV-X. In some embodiments, all reactions contained the potent thrombin inhibitor, lepirudin, to eliminate any feed-back on FVIII activation by generated thrombin. In some embodiments, these findings provided further experimental support of the identification of a FVIII activation function of nascent FXa associated with the extrinsic coagulation initiation complex (TF-FVIIa) that is distinct from the known direct FVIII activation by FXa itself.

In some embodiments, this concept is strengthened by the second line of evidence that single point mutations in FVIIa can abolish direct FXa generation by the extrinsic TF-FVIIa tenase complex, relative to the WT species, while preserving TF-FVIIa-dependent FVIII activation by nascent FXa and, thus, intrinsic tenase activity.

In some embodiments, the disclosure provided herein establish the structural and biochemical bases for the newly identified function of nascent FXa induced by the associated TF-FVIIa complex leading to FVIIIa generation. In some embodiments, this new function is distinct from the generally recognized extrinsic tenase activity generating FXa that becomes incorporated into the prothrombinase complex. Because this function enables intrinsic tenase activity, which in turn is strictly dependent on the anti-hemophilic FVIII essential for hemostasis, it constitutes the TF-initiated hemostatic loop defined here in its mechanistic details for the first time.

Example 27

Quantitative Measurements

In some embodiments, this disclosure allows distinct quantitative measurements of prothrombotic potential and hemostatic efficiency in individual blood samples under baseline conditions or during anticoagulant and/or anti-thrombotic treatment. In some embodiments, disclosed herein are methods of identification of new prohemostatic molecules for therapeutic use with decrease risk of inducing thrombosis (i.e. modified FVIIa molecules retaining support of the TF-initiated hemostatic loop through intrinsic tenase but decreased direct FXa generation).

It is commonly known that hemostasis is essential for arresting hemorrhage and preventing spontaneous bleeding. Blood coagulation plays a central role in sustaining hemostasis. In blood coagulation, factor (F) VIII functions as the essential co-factor for the intrinsic coagulation protease, FIXa. Once activated to its active form (FVIIIa), FVIIIa binds to FIXa and the FVIIIa-FIXa complex amplifies thrombin (FIIa) generation by promoting FXa generation. Finally, the generated FIIa converts fibrinogen to stable fibrin clot, leading to hemostasis. In support of the concept, the congenital defect of FVIII (hemophilia A) is associated with severe, sometime life-threatening, bleeding episodes. Hemophilia patients have been classified into three categories based on plasma FVIII coagulant activity (FVIII:C): severe (<1 IU/dl FVIII:C), moderate (1-5 IU/dl) and mild (>5 IU/dl). The FVIII:C is currently determined by clotting-based assays such as the partial activated thromboplastin time (APTT). The conventional clotting assay is useful for a general classification of patients, but among severe cases thus classified there is a considerable heterogeneity of clinical phenotypes. This is because the low sensitivity of the current coagulation-based FVIII assay is insufficient to discriminate moderate from severe bleeding risk resulting from FVIII:C levels in the ~1-0.1 IU/dl.

Example 28

Novel Assay

In some embodiments, a novel assay is disclosed herein that has a higher sensitivity and capable of discriminating between moderate and severe bleeding risk in patients. In some embodiments, the assay described herein allows a more detailed classification of patients, an accurate prediction of bleeding risk, and association with the prophylactic or therapeutic infusion of FVIII. In some embodiments, the sensitivity of the disclosed assay is up to 10 times greater than currently available methods. In other embodiments, the sensitivity of the disclosed assay is more than 10 times greater than currently available methods.

Figure 10:
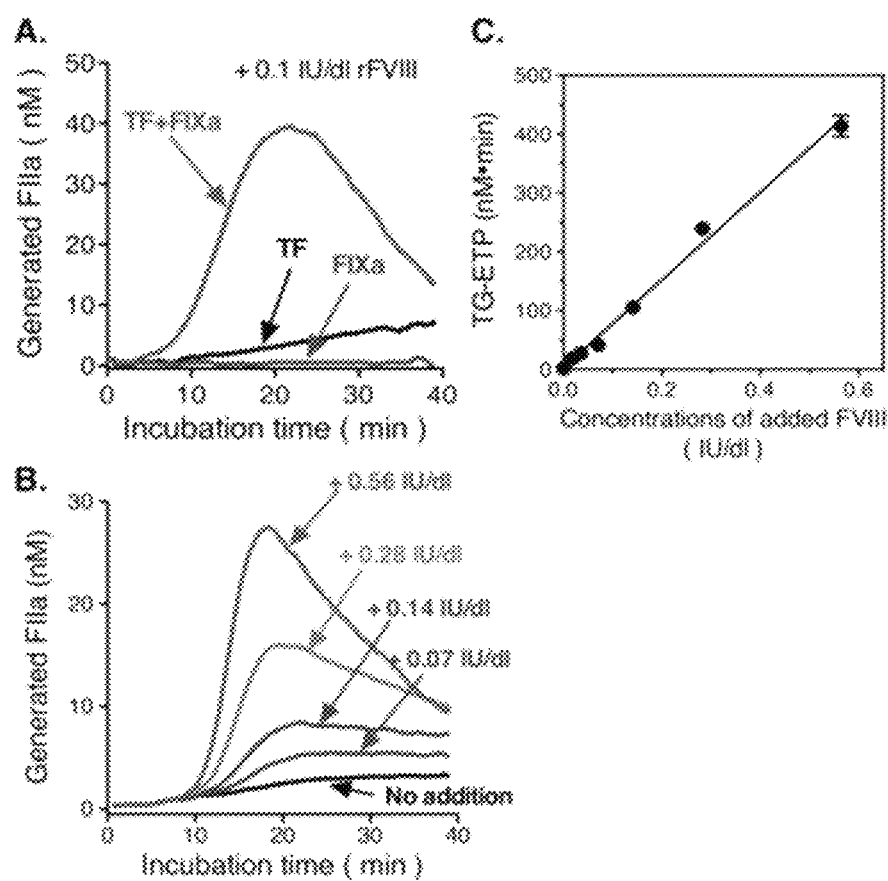
FIG. 10 illustrates, in accordance with embodiments herein, TG tests for measuring coagulant activity of spiked FVIII into severe hemophilia A patient plasma. TG was induced by an addition of re-lipidated TF (0.15 pM), FIXa (200 pM), or combined the two, followed by re-calcification. A. TG in patient plasma, which 0.1 IU/dl recombinant FVIII (rFVIII) was spiked. B. TG in patient plasma induced by combined TF and FIXa with phospholipids (5 μM), which 0.07-0.56 IU/dl plasma-derived FVIII was spiked. C. Calibration curve for FVIII constructed with TG parameter endogenous thrombin potential (ETP) determined by calculating area under the curves shown in panel B.

Based on the novel FVIII activation mechanism disclosed herein, a new assay is described. In some embodiments of this assay, TG is triggered by the combined addition of extremely low concentrations (e.g., picomolar concentrations) of re-lipidated TF and FIXa (picomolar or nanomolar concentrations) into patient plasma. In some embodiments, addition of TF or FIXa individually does not generate significant FIIa in hemophilia A patient plasma due to TF pathway inhibitor (TFPI) control and slow reaction, respectively. In other embodiments, combined addition of the two coagulation initiators at individually inactive concentrations synergistically amplifies TG (FIG. 10). In some embodiments, biochemical studies on the synergy mechanism in plasma shows that TF forms a complex with FVIIa and FX in which the latter is activated to FXa that, while still bound to TF-FVIIa and protected from TFPI inhibition (thus, with a different mechanism as compared to free FXa) activates FVIII to FVIIIa, which in turn binds to FIXa amplifying FXa generation and TG. In some embodiments, the novel TG method disclosed herein enables the detection of very low FVIII levels in plasma, as shown by assays of FVIII-spiked hemophilia A patient plasma to a detection limit of 0.07 IU/dl FVIII:C (FIGS. 10B and C). Thus, in one embodiment, the method disclosed herein specifically determines TF-driven FVIII activation and TG induced by the FVIIIa-FIXa complex.

In some embodiments, provided herein is a sensitive method for determining low levels of FVIII:C in severe hemophilia A patients and individuals with acquired FVIII deficiency. In some embodiments, provided herein is a novel assay that allows a more accurate characterization of bleeding phenotypes and prediction of bleeding risk in severe hemophilia A patients, thus improving replacement therapy with FVIII products.

In some embodiments, the novel assay disclosed herein is useful for monitoring treatment with FVIII concentrates and for assessment of concentrate potency. In other embodiments, the assay is utilized to identify FVIII variants with improved functionality, and/or increased stability, and/or for screening novel hemostatic agents with improved efficacy and safety for hemophilia A treatment.

Example 29

Factor FVIIa Mutants

In some embodiments, further evidence supporting the novel mechanism of cofactor VIII activation was obtained by characterizing two FVIIa mutants, T99Y and E154A. Both retain catalytic activity for cleavage of FX but with markedly reduced substrate turnover rates as compared to wild type (WT) FVIIa, thus cannot sustain FXa generation after the initial burst. In some embodiments, despite markedly decreased FXa generation, mutant and wild-type TF-FVIIa complexes supported comparable FXa-dependent FVIII activation. In some embodiments, under the same conditions the two mutants, unlike WT FVIIa, failed to activate the FV prothrombinase pro-cofactor that is highly homologous to FVIII. In some embodiments, despite the greatly impaired direct FXa generation, both FVIIa mutants supported FVIIIa-dependent FXa production in the presence of added FIXa as efficiently as WT. In some embodiments, these results show that FXa generation can be directly blocked by the TF-FVIIa extrinsic tenase complex. In some embodiments, this generates pro-thrombotic thrombin, without interfering with the pathway disclosed herein through which nascent TF-FVIIa-FXa activates the pro-hemostatic antihemophilic FVIIIa-FIXa intrinsic tenase complex.

In some embodiments, disclosed herein are biochemical bases for the novel FVIIIa generating function of nascent FXa within the TF-FVIIa complex that are distinct from that of free FXa released from extrinsic tenase for incorporated into the prothrombinase complex. In some embodiments, this novel function enabling intrinsic tenase activity, which in turn is strictly dependent on the antihemophilic FVIII essential for hemostasis, constitutes the TF-initiated hemostatic loop defined here in its mechanistic details for the first time.

In some embodiments, a difference between the two FVIIa mutants is in the ability to convert FIX to FIXa, a known function of the TF-FVIIa complex. In some embodiments T99Y and E154 FVIIa has comparable ability to support FVIII activation by nascent FXa product. Thus, both mutants as well as WT FVIIa supported FVIIIa-dependent FXa production by added FIXa. In some embodiments, when zymogen FIX was added instead, only the FVIIa exosite mutant E154A, but not T99Y, supported formation of a functional FVIIIa-FIXa intrinsic tenase complex leading to FXa generation.

Figure 5:
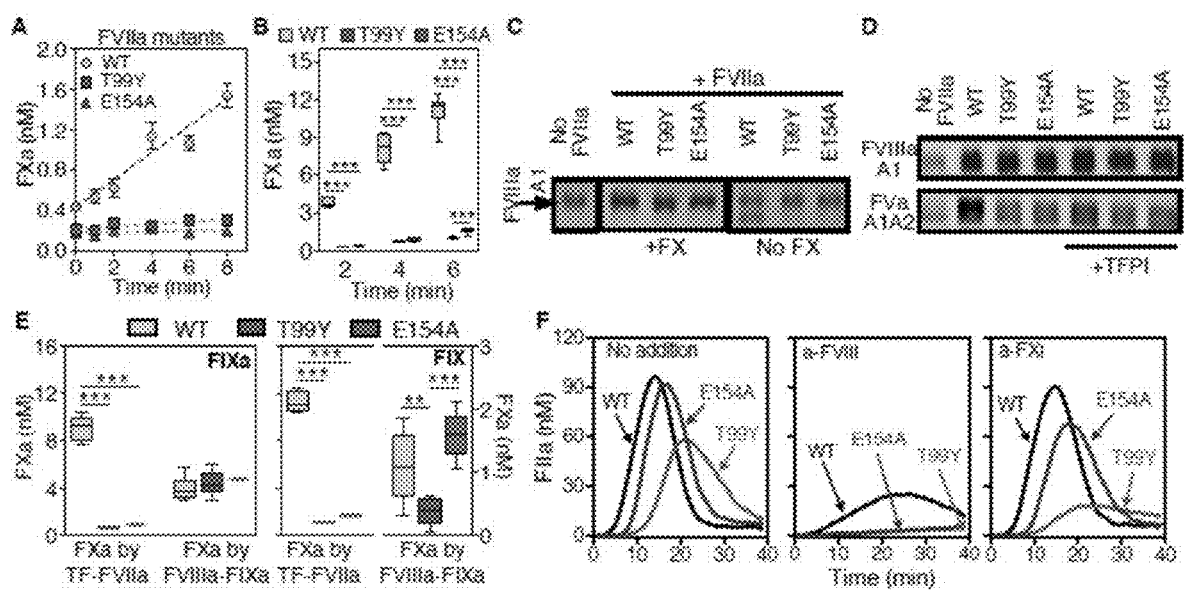
FIG. 5 illustrates, in accordance with embodiments herein, an embodiment wherein FVIIa mutants with impaired FXa product release can still support FVIII activation by nascent FXa. (A) Phospholipid-free assay of FX (1 µM) to FXa conversion by the complex of 2 µM soluble rTF with 10 nM FVIIa WT, T99Y or E154A. (B) FXa generation by 50 pM phospholipid-reconstituted rTF with 200 pM FVIIa WT, T99Y or E154A added to 135 nM FX, 0.7 nM FVIII, 3 nM FV and 200 nM lepirudin (2 min, n=2-3; 4 min, n=4-5; 6 min, n=6-9). (C) WB (representing 2) of FVIII activation in reactions of 50 pM TF, 200 pM FVIIa WT or mutants, 0.7 nM FVIII, 3 nM FV and 200 nM lepirudin without/with 135 nM FX, incubated for 120 s at 37° C. Note the smaller inactive FVIII A1337-372 domain generated by FVIIa WT in the absence of FX (11), indicating that activating cleavages are preferentially by nascent FXa. (D) WB (representing 2) of FVIII (top; incubation 180 s) and FV (bottom; incubation 420 s) activation induced by 50 pM TF, 200 pM FVIIa WT or mutant, 135 nM FX, without or with 10 nM TFPIα. (E) FXa generation measured in reactions as in (D) without TFPIα and in the presence of 10 nM FIXa (left, incubation 180 s; n=5-6 except=2 for E154A) or 90 nM FIX (right, incubation for 360 s; n=5-6). (F) TG (representing 3) by 2.5 pM TF in 30 µg/ml CTI-containing FVII deficient reconstituted PRP supplemented with 400 pM FVIIa WT or mutant without antibody (left), with anti-FVIII (8D4, 8 µg/ml; middle) or with anti-FXI (O1A6, 20 µg/ml; right). Results are shown as 25th-75th percentile bars with min to max whiskers (line at the median). Differences were evaluated by the ANOVA/Tukey test; results at 4 and 6 min in (B) and in reactions with FIX in (E, right) were analyzed after transformation as y=log 10 y (P<0.01, *P<0.001).

In some embodiments, the two FVIIa mutants were used to evaluate the importance of FIX conversion to FIXa by TF-FVIIa for thrombin generation in the setting of platelet-rich plasma (PRP) with physiologic coagulation inhibitors. Thus, by adding FVIIa to FVII-deficient plasma supplemented with normal washed platelets, it was found that WT or E154A FVIIa produced comparable levels of thrombin but T99Y FVIIa was less efficient (FIG. 5F). In some embodiments, inhibiting FVIIIa generation blocked TG by the two mutants, while WT FVIIa yielded residual TG (FIG. 5). This is consistent with the selective defect of the FVIIa mutants in triggering FXa and thus thrombin generation directly. In some embodiments, blocking FXIa activity had a modest effect on TG by FVIIa E154A as compared to WT, while it markedly reduced TG by FVIIa T99Y (FIG. 5). In some embodiments, these results demonstrated that activation of both FVIII and FIX are essential for TF-initiated intrinsic coagulation. In some embodiments, that the mutant FVIIa E154A, with limited direct FXa generation, was comparable to FVIIa WT in supporting TF initiation of the intrinsic pathway reinforces the concept that thrombin feedback has a limited role in FVIII activation during TF-triggered coagulation.

In one embodiment, the mutant E154A allows the measuring of the relative contribution of TF-FVIIa or FXIa-thrombin feedback loop to the generation of FIXa, the protease that combines with FVIIIa as cofactor to form the intrinsic tenase complex that activates FX to FXa escaping control by TFPI, the physiologic inhibitor of direct FXa generation by TF-FVIIa. This also is relevant to the discrimination of pro-hemostatic vs. pro-thrombotic reactions. In one embodiment, the assays disclosed herein can quantitatively assess the preservation of a pro-hemostatic mechanism resulting from FVIIIa generation though nascent TF-FVIIa-FXa.

In one embodiment, the mutant E154A of FVIIa was used in studing the direct pathway of FXa generation, caused by the inability to release generated FXa for assembly of prothrombinase. Surprisingly, the E154A mutant can nonetheless support FVIIIa generation by nascent FXa in the complex TF-FVIIa154A-FXa. It is contemplated that other mutant forms of FVIIa may have a similar effect. The format of this assay could include the properties of anti-FVIIa monoclonal antibody 12C7, which produces an effect similar to the FVIIa Y76F mutant. The latter is similar to FVIIa E154A with respect to minimal support of prothrombinase activity with preservation of the mechanism of prohemostatic FVIII activation by nascent FXa; but in addition causes FVIIa to lose the capacity to activate FIX to FIXa. This allows discriminating the pathway of FIXa generation supported by the thrombin-FXI loop, which is likely pro-thrombotic, from that supported by TF-FVIIa, which is integrated in the TF-FVIIa-FXa complex with FVIII activation. Thus, assays based on the use of antibodies like 12C7 should be protected.

Example 30

Screening of Anti-FVIIa Monoclonal Antibodies

Figure 9:
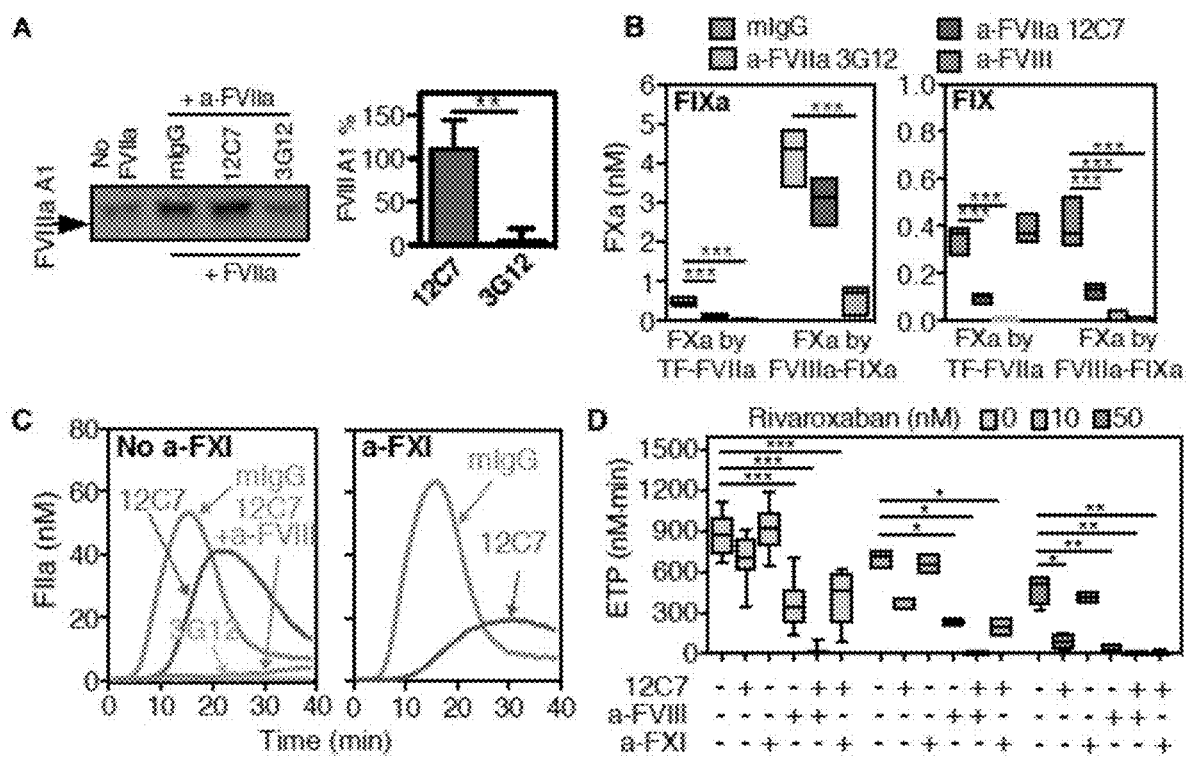
FIG. 9 illustrates, in accordance with embodiments herein, one embodiment of the disclosure provided herein. (A) WB analysis (representing 3) of the effect of anti-FVIIa MoAbs 3G12 and 12C7 (20 µg/ml) on TF-dependent FVIIIa generation after 120 s in reactions including 50 pM TF, 200 pM FVIIa, 135 nM FX, 3.5 nM FVIII, 3 nM FV and 200 nM lepirudin; quantification as in FIG. 4E. (B) Preservation of FVIIIa-dependent FXa generation by anti-FVIIa MoAb 12C7 in the presence of 10 nM FIXa (180 s incubation, n=3) but not 90 nM FIX (360 s incubation; n=3-5), in contrast to inhibition by MoAb 3G12. Reactions contained 50 pM TF, 200 pM FVIIa, 0.7 nM FVIII, 3 nM FV, 135 nM FX, 10 nM TFPI, 200 nM lepirudin and 2.5 mM $CaCl_2$; anti-FVIIa MoAbs or control mouse IgG were at 20 µg/ml; the function-blocking anti-FVIII MoAb 8D4 was at 8 µg/ml. (C) Effect of anti-FVIIa MoAbs 3G12 and 12C7 (20 µg/ml), without or with anti-FVIII MoAb 8D4 (8 µg/ml) or anti-FXI MoAb O1A6 (20 µg/ml), on TG in normal PRP. (D) Dose-dependent effect of rivaroxaban on TF-dependent TG in PRP in the presence of anti-FVIIa 12C7, anti-FVIII and anti-FXI MoAbs, as indicated (n=2-13 in different groups). Results in (B) and (D) are shown as 25th-75th percentile bars with min to max whiskers or min to max bars (when n≤3) with a line at the median. Differences were evaluated by a two-tailed t-test with Welch correction (A) or the ANOVA/Tukey test (B and D). *P<0.05, P<0.01, *P<0.001.

In some embodiments, a panel of anti-FVIIa monoclonal antibodies (MoAbs) was screened for interference with TF-mediated intrinsic pathway activation. This enabled applying the novel coagulation pathway to the characterization of prohemostatic and pro-thrombotic coagulation pathways in different individuals and patients treated with different anticoagulants. Whereas most inhibitory antibodies, exemplified by MoAb 3G12, prevented FVIII activation by the TF initiation complex, MoAb 12C7, known to react with a defined epitope close to the macromolecular substrate-binding exosite, had no inhibitory effect on this reaction (FIG. 9). In some embodiments, the antibody limited direct FXa turnover mediated by FVIIa WT (FIG. 9). In some embodiments, it allowed amplification of FXa generation through TF pathway-generated FVIIIa, but only when FIXa and not zymogen FIX was provided (FIG. 9B). In some embodiments, this finding demonstrates that MoAb 12C7 inhibits FIX conversion to FIXa by TF-FVIIa. In some embodiments, this provides a tool to dissect functionally the different pathways potentially leading to FIXa generation in blood and testing their functional significance for hemostasis or thrombosis. Indeed, in various embodiments, unlike the inhibitory anti-FVIIa MoAb 3G12, MoAb 12C7 preserved TG in normal PRP. In other embodiments, FVIII-dependent TG in the presence of MoAb 12C7 became highly susceptible to inhibition by anti-FXI antibody (FIG. 9C). In some embodiments, MoAb 12C7 mimics the properties of mutant FVIIa T99Y. Furthermore, low rivaroxaban concentrations caused a more pronounced inhibition of thrombin generation (TG) in the presence of MoAb 12C7 (FIG. 9D), confirming that FXa targeted anticoagulants inhibit thrombin-FXI feedback loops while selectively preserving direct FVIII and FIX activation by the TF initiation complex.

Example 31

Assay or Test

In some embodiments, the newly identified TF-dependent FVIII activation pathway has a key role in initial thrombin generation (TG) via the FVIIIa-FIXa complex, leading to the secondary TG burst essential for hemostasis. In some embodiments a test was implemented in which TG is triggered by the combined addition of extremely low concentrations (e.g., 0.15 pM) of re-lipidated TF at and FIXa (e.g., 200 pM) into patient plasma. Addition of TF or FIXa individually does not generate significant FIIa in hemophilia A patient plasma due to TF pathway inhibitor (TFPI) control and slow reaction, respectively. In contrast, combined addition of the two coagulation initiators at individually inactive concentrations synergistically amplifies TG (FIG. 10). In some embodiments, the novel method disclosed herein enables the detection of very low FVIII concentrations in plasma. Importantly, the mechanism detected by this new assay differs from the known mechanism of FVIII activation by free FXa. In some embodiments, as shown by measurements in FVIII-spiked hemophilia A patient plasma, the detection limit of the new assay is 0.07 IU/dl FVIII:C. Thus, in one embodiment, the invented method specifically determines TF-driven FVIII activation and TG induced by the FVIIIa-FIXa complex.

In some embodiments, the present disclosure is the basis for newly designed coagulation assays that can help individualize the definition of thrombotic and bleeding risk for patients treated with new oral anticoagulants. For example, in one embodiment, the method disclosed herein can objectively identify situations requiring dosage adjustment for better anti-thrombotic effect or for reducing the possibility of bleeding complications. In some embodiments, the present disclosure provides new perspectives relevant to the identification and testing of new pharmacological approaches for the prevention and treatment of thrombosis while preserving sufficient hemostatic function.

In some embodiments, the present disclosure allows the evaluation of new anti-thrombotic drug candidates specifically and quantitatively focusing on functional preservation or degradation of coagulation cofactors in the context of TF-initiated clotting, differentiating between pro-thrombotic and pro-hemostatic pathways. In some embodiments, this improves the section of drug candidates with the best profile for antithrombotic effects versus safety profile with respect to bleeding complication. In some embodiments, the same benefits improves the monitoring and evaluation of anti-thrombotic regimens based on new drugs or combination of drugs, a key issue to achieve the best individualized treatment with different target-selective anticoagulants on mechanistic ground. With respect to hemostasis, novel assays disclosed herein detects low levels of FVIII:C in severe hemophilia A patients, and individuals with acquired FVIII deficiency. In some embodiments, FVIII activity assays with increased sensitivity allows a more accurate characterization of bleeding phenotypes and prediction of bleeding risk in severe hemophilia A patients, thus improving replacement therapy with FVIII products. In some embodiments, such assays also help identify variants of antihemophilic FVIII with gain of function and/or increased stability in the newly identified coagulation pathway, thus improving replacement therapy in patients with defective anti-hemophilic FVIII function.

Example 32

Generally

Blood clotting in response to tissue injury is key for hemostasis and innate immunity, but can cause vascular thrombosis leading to serious diseases. In the current coagulation scheme (FIG. 1, left), the extrinsic pathway initiation complex of tissue factor (TF) with active factor (F) VIIa promotes a cascade of proteolytic reactions yielding FXa that combines with FVa in the pro-thrombinase complex converting prothrombin to thrombin. Initially generated thrombin activates the FVIII and FV cofactors in feedback reactions that amplify coagulation. How active cofactors can be generated prior to significant thrombin production remained a puzzling question and FXa is now viewed as the relevant FV activator during coagulation initiation. This disclosure provides the contribution of FXa and/or TF-FVIIa to coagulation initiation through direct FVIII activation.

Extrinsic coagulation initiation is controlled by the TF pathway inhibitor (TFPI), which by inactivating FVIIa and FXa within a quaternary complex with TF attenuates thrombosis. Moreover, a positively charged TFPIα carboxyl terminal region interacts with a specific acidic sequence in partially processed FV interfering with FXa formation of active prothrombinase. These mechanisms reducing direct thrombin generation are compensated by TF-FVIIa activating the intrinsic pathway FIX in a kinetically favored reaction in the presence of physiologic plasma inhibitors. Alternatively, FIXa is generated by FXIa activated in a thrombin feedback loop also promoting vascular inflammation or by contact phase FXIIa. In mouse models FXIIa contributes to amplified thrombin generation in experimental thrombosis but, consistent with human data has no role in hemostasis.

The currently known coagulation paradigm, with the expanded function of TFPI tightly controlling both TF-dependent initiation and prothrombinase generation, cannot readily explain how initially produced thrombin can be the origin of FVIIIa cofactor for FIXa produced by the contact pathway or by TF-FVIIa itself. Thus, the inventors have herein disclosed a novel function of the extrinsic coagulation initiation complex whereby nascent FXa associated with TF-FVIIa directly activates FVIII resisting inhibitor control by TFPI. Such a mechanism may be relevant for the function of TF in hemostasis and provides new perspectives for interpreting the distinct roles of coagulation reactions in physiologic and pathologic thrombus formation.

Example 33

Methods

Materials. Mouse and rabbit IgG, quinacrine-HCl and apyrase were from Sigma-Aldrich (St. Louis, MO). Human prothrombin (FII), thrombin (FIIa), FV, FVa, FIX, FIXa, FX, FXa, CTI, dansylarginine N-(3-ethyl-1,5-pentanediyl)amide (DAPA) and anti-human FV MoAb AHV-5146 (binding to A1-A2 domain residues 306-506) were from Haematologic Technologies (Essex Junction, VT). Bovine serum albumin was from Calbiochem (San Diego, CA); rTF (Dade Innovin) from Siemens Healthcare Diagnostics (Deerfield, IL); human protein S from Enzyme Research Laboratories (South Bend, IN); nematode anticoagulant protein (NAP) c2 and tick anticoagulant peptide (TAP) from Corvas International (San Diego, CA). Of the anti-human FVIII MoAbs used, ESH-8 was from Sekisui Diagnostics (Stamford, CT); 8D4 was a gift of Dr. Marc Jacquemin (Leuven, Belgium); and C5, directed against the A1 domain, was prepared in the laboratory. FVIII was a gift from Bayer Healthcare (Berkeley, CA). Recombinant TFPI; soluble TF (residues 1-218); human FVIIa WT and mutants S195A (chymotrypsin numbering; iFVIIa), T99Y and E154A; and prothrombin S195A were produced and characterized as described. Hirugen, MoAbs anti-mouse TF 21E10, anti-human FVIIa 12C7, anti-mouse FXI 14E11 and anti-human FXI O1A6 were previously characterized. Inhibitory anti-TFPI polyclonal antibody, anti-human FVIIa 3G12 and anti-human TF 5G9 MoAbs were made by the inventors.

Blood perfusion experiments. TF-coated glass coverslips were perfused with venous blood at a wall shear rate of 300 $s^{-1}$. A Zeiss Axiovert 135M/LSM 410 and Plan-Apochromat 40x/1.40 NA oil immersion objective (Carl Zeiss AG, Oberkochen, Germany) was used to visualize platelets/leukocytes and fibrin stained with mepacrine and a specific anti-body, respectively. Image analysis to calculate volumes was performed as described herein.

TG analysis in human native or reconstituted platelet-rich plasma (PRP). TG in PRP or reconstituted PRP was evaluated as described herein. Platelets in PRP were adjusted to $180 \cdot 10^3/\mu l$ with homologous platelet-poor plasma (PPP) and CTI was added at 30-50 µg/ml. Reconstituted PRP was prepared with washed platelets resuspended at $180 \cdot 10^3/\mu l$ into PPP. Thrombin generation (TG) was initiated by adding rTF and/or FIXa at defined concentrations with 18 mM $CaCl_2$ into micro-titer plate wells containing 360 µM benzyloxycarbonyl-glycyl-glycyl-L-arginine coupled to fluorogenic 7-amido-4-methylcoumarin (Gly-Gly-Arg-AMC; Bachem Americas, Torrance, CA) as thrombin substrate. The rate of fluorescence intensity increase (measured at 355/460 nm excitation/emission) as a function of time (dF/dt) was calculated with Turbo Delphi 2006 (Borland Software Corporation, Austin, TX) and converted to thrombin-equivalent concentration (nM) using a calibration curve. TG was also measured with a discontinuous 2-stage assay with a detection limit of 5 pM. In this assay, reactions incubated for up to 11 min at 37° C. were terminated with 20 mM EDTA and generated thrombin was measured using the sensitive thrombin substrate H-D-CHA-Ala-Arg-AMC•2AcOH (Pefafluor TH, Pentapharm, Basel, Switzerland) at 50 µM.

Analysis of FVIII and FV activation by immunoblotting. Coagulation products were separated by sodium dodecyl sulfate-polyacrylamide gel electrophoresis (SDS-PAGE) under reducing conditions, except for reactions containing anti-FVIIa MoAbs that were processed under non-reducing conditions to avoid confounding effects from IgG light chains with a molecular mass comparable to FVIII A1 domain. Proteins transferred to polyvinylidene fluoride membranes were probed with anti-FVIII MoAbs C5 (0.5 µg/ml) or anti-FV AHV-5146 (1 µg/ml). FVIIIa and FVa were quantified by infrared detection with the Odyssey infrared imager (Li-COR, Lincoln, NE) calibrated with known FVIIIa and FVa quantities.

Coagulation activation in reactions with purified components. Reactions in 50 mM Tris-buffered saline, pH 7.4, with 0.1% bovine serum albumin included 0.7 nM FVIII, 3 nM FV, 135 nM FX and 1 µM prothrombin without/with 4 µM DAPA. TFPI and other inhibitors were added as indicated. Reactions were initiated by rTF (50 or 400 pM) with FVIIa (200 or 500 pM) and/or FIXa (2 or 10 nM) added with 2.5 mM $CaCl_2$ and incubated at 37° C. for the indicated times. After quenching the reaction with 10 mM EDTA, generated FXa was measured with S-2765 (180 µM). FVIIIa procoagulant activity was measured as FIXa-dependent FXa generation; FVIIIa procoagulant activity generated by the nascent TF-FVIIa-FXa complex was calculated by subtracting the amount of FXa produced in reactions initiated by FVIIa and FIXa individually from that produced in reactions initiated by FVIIa/FIXa combined. When indicated, 200 nM lepirudin was used to inactivate possible thrombin contamination.

Ferric chloride-induced thrombosis in mice. Animal procedures complied with the Guide for Care and Use of Laboratory Animals and were approved by the TSRI Animal Care and Use Committee. Vascular injury was induced in C57BL/6J mice by one 0.8 µl drop of 7% (0.26 M) or 8% (0.30 M) $FeCl_3 \cdot 6H_2O$ applied on the carotid artery for 3 min; or a 0.4 µl 4% (0.15 M) drop for 1 min on the femoral vein, followed by rinsing. Antibodies were administered by bolus injection into the catheterized jugular vein. FVIII and FVIIIa were administered by a bolus injection (1.4 pmoles) followed by maintenance with continuous infusion at the rate of 0.47 pmoles/min for 15 min. Time to first occlusion after injury and flow index were quantified as described in the art.

Study approval. Studies involving human subjects were approved by appointed Institutional Re-view Boards. Human volunteers gave informed consent to participate in the studies before blood collection and experiments were performed in accordance with established procedures.

Statistics. Group variances were evaluated with Levene's median and Bartlett's tests; differences with one-way ANOVA or Kruskal-Wallis tests followed by Tukey's and Dunn's tests, respectively, for multiple comparisons. Data were transformed as $y=\log_{10} y$ when necessary to obtain homoscedasticity. Software packages used were GraphPad Prism version 7 (GraphPad Software, La Jolla, CA) and XLSTAT (Addinsoft, Paris, France).

Example 34

Results

Figure 11:
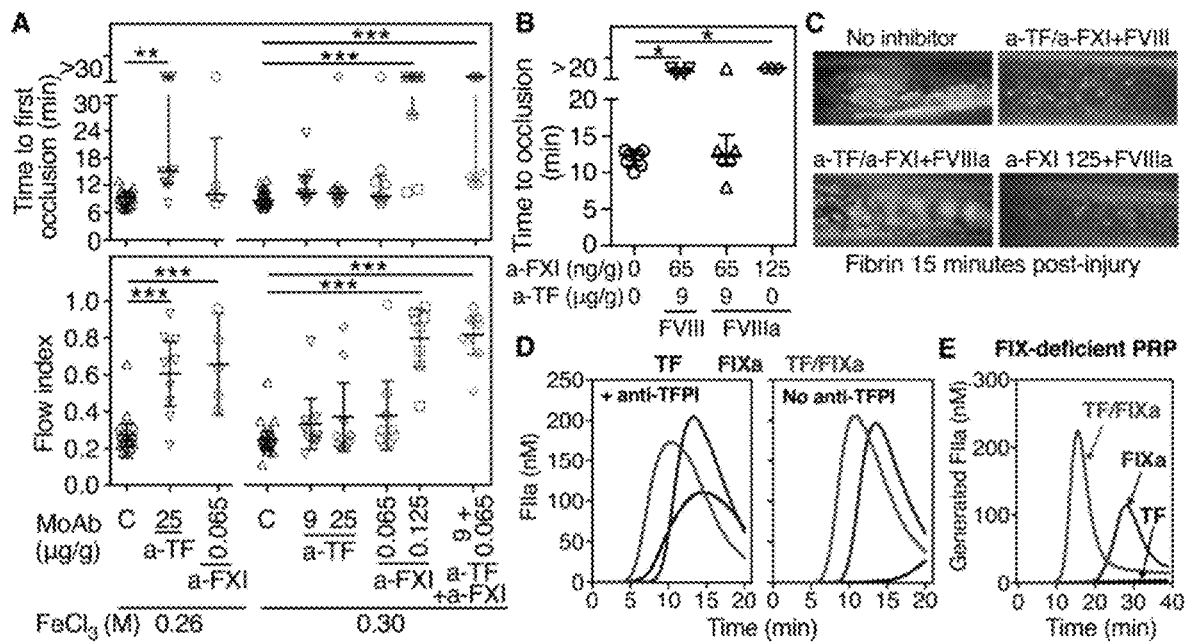
FIG. 11 illustrates, in accordance with embodiments herein, TF pathway and FVIII activation in vivo. (A) Carotid artery occlusion after injury by 7% (0.26 M) or 8% (0.3 M) $FeCl_3 \cdot 6H_2O$ in C57BL/6J mice treated with anti-TF 21E10 and/or anti-FXI 14E11 MoAbs, as indicated (n=5-20 in different groups); control mice (C) were injected with buffer or isotype-matched non-immune mouse IgG. (B) Femoral vein occlusion after injury by 4% (0.15 M) $FeCl_3 \cdot 6H_2O$ in mice (n=3-7) receiving FVIII or FVIIIa (1.4 pmole bolus/ 0.47 pmole/min for 15 min) before injury and MoAb treatment. Results in A, top, and B (dot plots, median and interquartile range) were analyzed with Kruskal-Wallis/ Dunn tests; in A, bottom (dot plot, mean and 95% CI) with ANOVA/Tukey tests. *P<0.05, P<0.01, *P<0.001. (C) Fibrin formation in the femoral vein. Top left, control mice injected with phosphate-buffered saline; top right, FVIII injection does not prevent the anti-thrombotic effect of 9 μg/g anti-TF/65 ng/g anti-FXI MoAbs combined; bottom left, FVIIIa injection bypasses inhibition by this anti-body combination; bottom right, FVIIIa cannot bypass inhibition by a full dose (125 ng/g) of anti-FXI MoAb alone. (D) Representative TG (n=3) induced by 0.15 pM rTF and/or 20 pM FIXa in citrated human PRP ($180 \cdot 10^3$ platelets/μl) recalcified with 18 mM $CaCl_2$ at 37° C. and containing 30 μg/ml CTI to block FXIIa and (left) 40 μg/ml rabbit anti-TFPI IgG or (right) non-immune IgG. (E) Representative TG (n=2) induced by rTF and/or FIXa as above in recalcified FIX-deficient PPP containing 50 μg/ml CTI and $180 \cdot 10^3$ normal washed platelets/μl.

The TF pathway activates FVIII in vivo. As previously shown, contact phase FXII and TF contribute to experimental thrombosis in the ferric chloride-induced carotid artery occlusion model, but how this happens remains unclear. The inventors found that monoclonal antibodies (Mo-Abs) blocking TF function or FXI activation by FXIIa independently reduced occlusion after a vessel wall lesion caused by 7% (0.26 M) $FeCl_3$ (FIG. 11A). After a lesion by 8% (0.3 M) $FeCl_3$ the same MoAb concentrations were ineffective, but a higher dose of the anti-FXI MoAb—not of the anti-TF—still prevented thrombosis (FIG. 11A). Thus, even after the more severe lesion, thrombogenesis required FIXa generation by FXIIa-FXIa. Remarkably, under the latter conditions, combining the low doses of anti-TF and anti-FXI MoAbs that individually had no antithrombotic activity reduced arterial occlusion significantly (FIG. 11A), confirming a role for the TF pathway in this intrinsic coagulation-dependent model of thrombus formation. Thus, TF might contribute to activate FVIII, the essential cofactor for the intrinsic tenase protease, FIXa. As visualized in the femoral vein, FVIIIa—but not FVIII—prevented inhibition of $FeCl_3$-induced fibrin deposition by the low-dose anti-TF/anti-FXI MoAb combination, but not by high-dose anti-FXI alone (FIG. 11B, C). These results ruled out that FIXa generated by TF-FVIIa or alternative pathways used exogenously-provided FVIIIa to trigger thrombosis, supporting the concept that TF-FVIIa contributes to FVIII activation in vivo.

To obtain experimental evidence supporting this concept, thrombin generation (TG) was measured in platelet-rich plasma (PRP). In reactions containing an inhibitory polyclonal antibody blocking TFPI and corn trypsin inhibitor (CTI) preventing FXI activation by FXIIa, the inventors defined the concentrations of FIXa or recombinant relipidated TF (rTF) yielding comparable TG (FIG. 11D, left). At the same concentration but without TFPI blockade (FIG. 11D, right), rTF produced little thrombin and late in the reaction, but enhanced TG with FIXa added concurrently. This amplification of FIXa-triggered TG required FVIII at <10% plasma concentration but not FIX (FIG. 11E), excluding additional TF-dependent FIXa generation. Since FVIII concentrations known to be sufficient to prevent severe spontaneous bleeding in FVIII-deficient patients could support synergistic TG amplification, the conditions of this assay appear to be relevant for assessing hemostatic competence in PRP.

Figure 12:
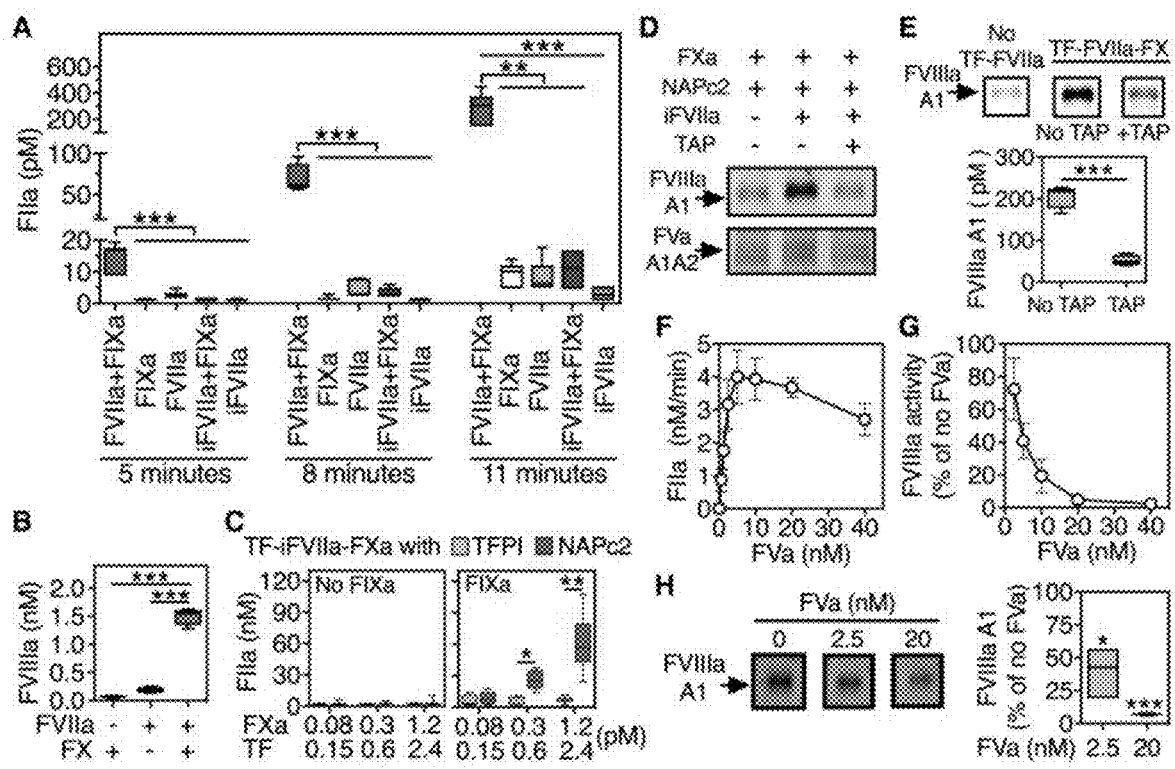
FIG. 12 illustrates, in accordance with embodiments herein, that the TF initiation complex activates FVIII. (A) TG was induced by 20 pM FIXa; or 400 pM FVIIa WT or inactive S195A mutant (iFVIIa); or FIXa combined with FVIIa WT or iFVIIa added into FVII-deficient reconstituted PRP ($180 \cdot 10^3$ platelets/μl) containing 30 μg/ml CTI, 0.15 pM rTF and 18 mM $CaCl_2$, followed by incubation for 5 (n=2-5), 8 (n=2-5) or 11 (n=3) min at 37° C. (B) FVIII (1.4 nM) activation by 400 pM rTF-500 pM FVIIa with/without 135 nM FX in reactions containing 40 nM TFPIα and 200 nM lepirudin incubated for 30 s at 37° C. After blocking residual FXa and TF-FVIIa with 70 nM tick anticoagulant peptide (TAP) and 20 μg/ml each of MoAbs 5G9 and 12C7, respectively, FVIIIa clotting activity (n=2-4) was measured adding the reaction mixture into FVIII-deficient plasma with 10 nM FIXa, 20 μM PL and 8 mM $CaCl_2$. (C) TG as in (A) but induced by a preformed complex of 10 nM TF/10 nM iFVIIa/5 nM FXa and 40 nM TFPI or NAPc2 added at the indicated TF/FXa concentrations without (left) or with (right) 10 pM FIXa. Incubation for 8 min at 37° C. (n=3-5). Results in (A-C) are shown as 25th-75th percentile bars (min-to-max whiskers, line at the median) or, when n<3, min-to-max floating bars (line at the mea; analysis by ANOVA/Tukey tests (after $y = \log_{10} y$ transformation in C). *P<0.05, P<0.01, *P<0.001. (D) Representative immunoblots (n=2) of FVIIIa and FVa generation after 30 or 60 s in reactions with the indicated combinations of 200 pM FXa, 500 pM iFVIIa, 40 nM NAPc2 and 1 μM TAP added to 400 pM rTF, 700 pM FVIII, 3 nM FV and 200 nM lepirudin. (E) Top. Representative immunoblots showing the effect of TAP (1 μM) on FVIII activation by TF-FVIIa (400 and 500 pM, respectively) and 135 nM FX. Reactions, containing also 700 pM FVIII, 3 nM FV and 200 nM lepirudin, were incubated for 30 s at 37° C. Bottom. Quantification of experiments as shown in the top panel (n=4), presented as 25th-75th percentile bars and analyzed by two-tailed t-test. ***P<0.001. (F) Dose-response of FVa effect on 1 μM prothrombin conversion to thrombin in reactions containing 10 pM FXa, 50 pM rTF and 700 pM FVIII incubated 180 s at 37° C.; mean±95% CI (n=4). (G) Dose-response of FVa effect on FVIII activation by 10 pM FXa in reactions with 50 pM rTF, 700 pM FVIII, and 200 nM lepirudin incubated 180 s at 37° C. FVIIIa activity (mean±95% CI, n=4) was measured as generated FXa in the presence of 2 nM FIXa and expressed as percent of that measured in the absence of FVa. (H) Left. Representative immunoblots (n=3) of FVIIIa generation in reactions as in G. Right. Quantification of generated FVIIIa (n=3) expressed as in (G) and shown by min-to-max floating bars; analysis by one sample t test.

The TF-FVIIa-FXa complex activates FVIII. The mechanism of TF-induced priming of intrinsic coagulation was studied using a sensitive two-stage TG assay. In FVII-deficient plasma reconstituted with normal platelets, 0.15 pM rTF with wild-type (WT) FVIIa produced little thrombin (<20 pM in 11 min), similar to that generated by the active site mutant FVIIa S195A (iFVIIa) or FIXa alone (FIG. 12A). However, rTF and FVIIa WT—but not inactive FVIIa S195A—combined with FIXa amplified TG ~5-20 times in 5-11 min (FIG. 12A). Thus, the additive quantities of thrombin produced in this assay by TF-FVIIa and FIXa separately were far less than the amount yielded by the two combined, demonstrating a synergistic interaction linking TF-initiated and intrinsic coagulation upstream of thrombin generation.

To identify the reaction that, apart from thrombin, could yield the FVIIIa required for FIXa-dependent coagulation, the inventors considered TF-FVIIa and FXa as potential FVIII activators. First, it was determined that TF-FVIIa without FX- or TF-FX without FVIIa-generated no or minimal FVIIIa activity, but TF-FVIIa with FX-generating FXa-produced substantial amounts of FVIIIa when all reactants were at physiologically relevant concentrations (FIG. 12B). In order to distinguish between functions of FXa after release from TF-FVIIa as opposed to FXa associated with TF-FVIIa, the inventors formed a stable TF-FVIIa-FXa complex with the nematode anticoagulant protein (NAP) c2. In the formed complex, catalytic activity of FVIIa was excluded by the S195A active site mutation (iFVIIa), while it is known that FXa retains catalytic function when trapped in the NAPc2 complex. This complex failed to induce TG in FVII-deficient reconstituted PRP, but markedly enhanced FIXa-induced TG (FIG. 12C), suggesting that FXa associated with TF-FVIIa can activate FVIII. A similar complex formed with TFPI, which inhibits FXa, was inactive alone and did not support FIXa-dependent TG in PRP (FIG. 12C). Surprisingly, the preformed complex of TF-iFVIIa-FXa stabilized by NAPc2 could activate purified FVIII, but not the homologous cofactor FV (FIG. 12D). Specific inhibition with TAP confirmed that FXa in the stabilized TF-iFVIIa-FXa complex activated FVIII (FIG. 12D), implying that nascent FXa still associated with TF-FVIIa can exert the same function (FIG. 12E).

Next, the inventors evaluated whether free FXa, which triggers coagulation by forming the prothrombinase complex, could serve as a FVIII activator in physiologic settings akin to its function in generating the prothrombinase cofactor, FVa. On the same procoagulant membrane used in the experiments above, increasing concentrations of FVa markedly stimulated prothrombin conversion by a low concentration of FXa (FIG. 12F). In contrast, generation of FVIIIa activity (FIG. 12G) or proteolytic cleavage of FVIII (FIG. 12H) by the same FXa concentration was progressively inhibited by adding FVa in the same concentration range, indicating that FXa bound to FVa cannot efficiently activate FVIII. Thus, nascent FXa associated with TF-FVIIa preferentially activates FVIII, triggering the intrinsic coagulation pathway. Subsequent FXa transfer from TF-FVIIa into the prothrombinase complex with FVa marks the transition to direct TF-induced coagulation.

Figure 13:
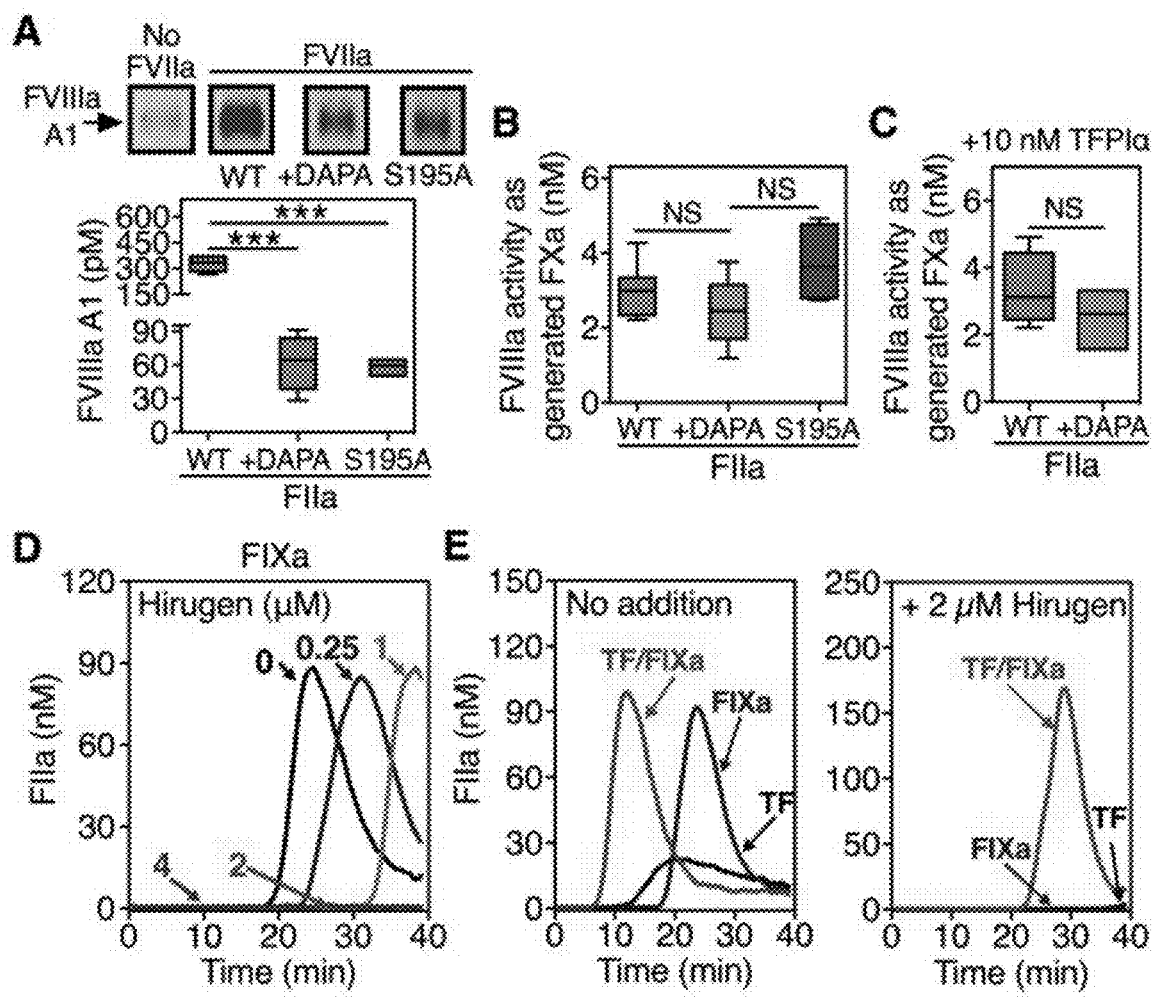
FIG. 13 illustrates, in accordance with embodiments herein, Thrombin-independent FVIII activation by nascent TF-FVIIa-FXa. (A) Top. Representative immunoblots showing FVIIIa A1 activation fragment generation induced by 200 pM FVIIa/50 pM rTF (0.37 μM phospholipids) in reactions containing 700 pM FVIII, 3 nM FV, 135 nM FX, 1 μM prothrombin (FII)—WT without/with 4 μM DAPA (n=4) or inactive S195A mutant (n=3)—and 2.5 mM $CaCl_2$) incubated at 37° C. for 120 s. Bottom. Quantification of generated FVIIIa-A1 calibrated with known quantities of the fragment. (B) FVIIIa activity calculated from FXa generation in reactions as in (A), but with 10 nM FIXa added and incubated for 180 s at 37° C. (n=4-12). FXa generation depend-ent on FVIIIa-FIXa activity was calculated by subtracting FXa generated by FVIIa and FIXa added individually from that by FVIIa/FIXa added together. (C) FVIIIa activity generated and calculated in reaction as in (A, B) but with the addition of 10 nM TFPIα. Results in A (bottom), B and C—shown as 25th-75th percentile bars, min-to-max whiskers, line at the median; or min-to-max floating bars with line at the mean when n≤3—were analyzed by ANOVA/Tukey tests. ***P<0.001; NS, not significant. (D) Effect of different hirugen concentrations on TG initiated by 10 pM FIXa in normal PRP ($180 \cdot 10^3$ platelets/pi) containing 30 μg/ml CTI and 20 μg/ml anti-FXIa blocking MoAb O1A6 (n=3). (E) Representative thrombograms initiated in normal PRP-containing CTI and anti-FXIa MoAb as in (D)—by 0.15 pM rTF and/or 10 pM FIXa without (left) or with (right) 2 μM hirugen (n=3).

The TF-FVIIa-FXa complex activates FVIII independently of thrombin. To assess the relative roles of the nascent TF-FVIIa-FXa complex and thrombin in generating FVIIIa, pro-cofactor activation on rTF-bearing phospholipid vesicles mixed with purified FX, prothrombin, FVIII and FV was studied. Activation of FVIII after FVIIa addition was partially inhibited by blocking thrombin with DAPA or by replacing normal prothrombin with inactive S195A mutant, but ~15% FVIIIa was still detectable under both conditions (FIG. 13A). Importantly, although thrombin could generate more FVIIIa, as expected from efficient FVIII cleavage in the solution phase, the amount of VIII activated by the TF-initiated reaction in the absence of active thrombin was sufficient for full function of membrane assembled FVIIIa- FIXa intrinsic tenase complex (FIG. 13B). In agreement with the results in PRP containing endogenous coagulation inhibitors (see FIG. 11D), TFPI that markedly suppressed direct FXa generation by TF-FVIIa had limited effect on the formation of functional FVIIIa-FIXa complex in TF-initiated reactions (FIG. 13C). The latter was also resistant to inhibition by TFPIα with the co-factor protein S—partial inhibition by protein S alone likely resulted from competition for limited procoagulant surfaces. Consistent with the observed thrombin-independent FVIII activation by nascent FXa in PRP, FVIII activation by TF-FVIIa-X was not influenced by von Willebrand Factor (VWF) binding FVIII.

To demonstrate directly that rTF can support FVIII activation in a physiological plasma milieu independently of thrombin feedback reactions, the inventors used hirugen (63-O-Sulfo-Tyr-hirudin to block thrombin exosite I required for cofactor activation. Hirugen dose-dependently inhibited FVIII activation by thrombin, but not FXa generated by TF-FVIIa-FIXa. In PRP with CTI and anti-FXI MoAb to block feedback TG amplification through increased FIXa generation by FXIa, 2 µM hirugen blocked FIXa-dependent TG (FIG. 13D), demonstrating this reaction required thrombin feedback activation of FVIII. In contrast, the same hirugen concentration failed to inhibit TG by FIXa combined with rTF, even though no TG could be detected when FIXa and rTF were added separately (FIG. 13E). Thus, the TF pathway activates FVIII in plasma when thrombin feedback loops are inhibited. Of note, experiments with mouse microvesicles generated from WT or human TF knock-in macrophages showed that thrombin-independent FVIIIa generation occurred also on a natural pro-coagulant surface with human or mouse TF-FVIIa.

Figure 14:
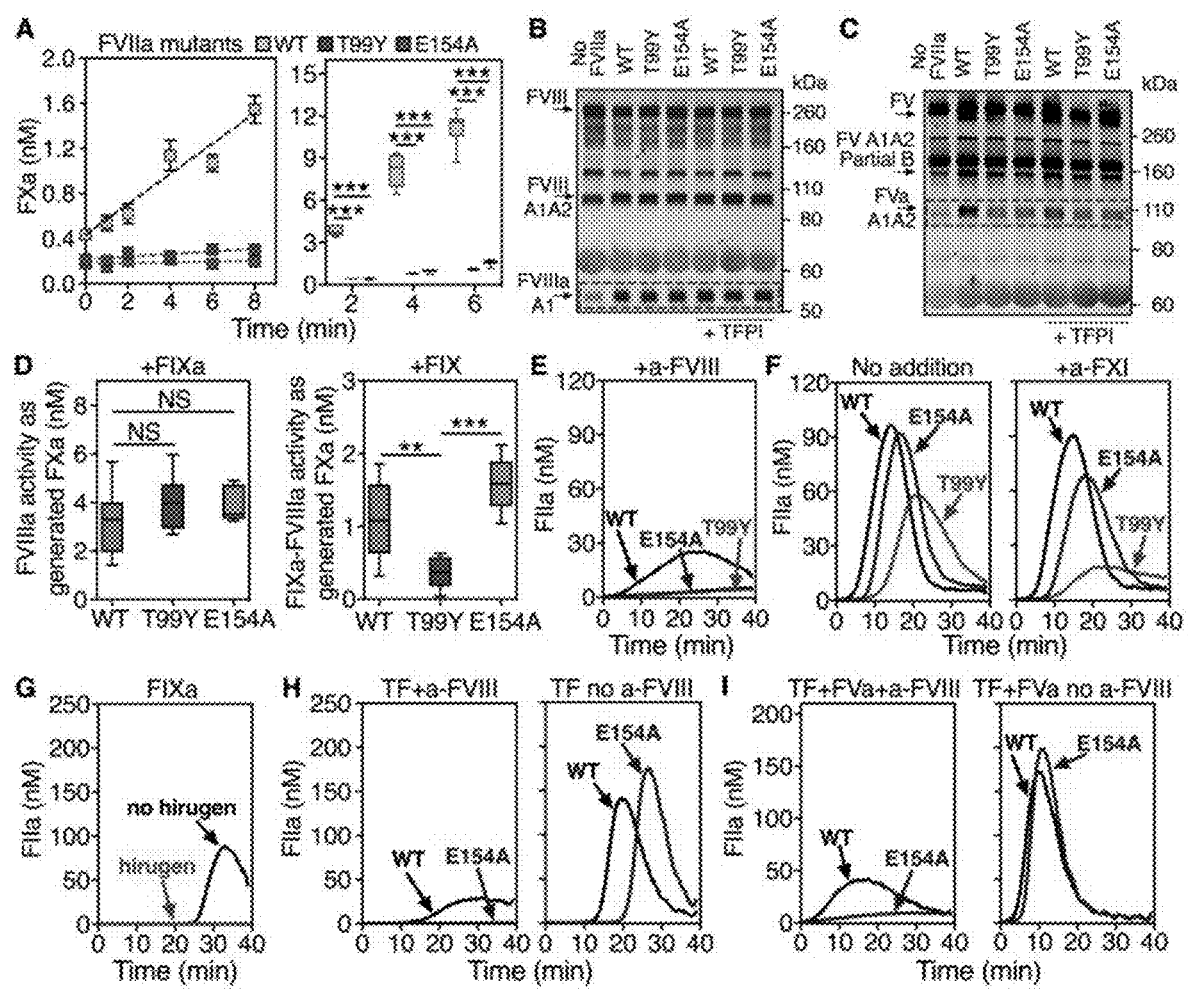
FIG. 14 illustrates, in accordance with embodiments herein, FVIIa mutants with impaired FXa product turnover support FVIII activation by nascent FXa when thrombin feedback is blocked. (A) Left. Time-course (mean±SEM) of 1 μM FX activation by 2 μM phospholipid-free soluble recombinant TF with 10 nM FVIIa WT (n=4-7), T99Y (n=2-3) or E154A mutants (n=3-4); incubation at 37° C. Right. FXa generation in reactions with 50 pM phospholipid-reconstituted rTF, 200 pM FVIIa WT or mutants, 135 nM FX and 700 pM FVIII incubated for 2 (n=2-3), 4 (n=4-5) or 6 (n=6-9) min. (B) Representative immunoblots (n=2) of FVIII activation by 50 pM rTF, 200 pM FVIIa WT or mutants, 135 nM FX, 700 pM FVIII, 3 nM FV, 200 nM lepirudin, without/with 10 nM TFPIα incubated for 180 s. (C) Representative immunoblots (n=2) of FV activation in reactions as in (B) incubated 420 s. (D) Left. FVIIIa activity (25th-75th percentile bars, min to max whiskers, line at the median) generated as in (B), but without TFPIα, measured as FXa produced by 10 nM FIXa (n=9 for FVIIa WT and T99Y; n=5 for E154A). P<0.01, *P<0.001) by ANOVA/Tukey tests. Right, FVIIIa-FIXa activity generated with 90 nM FIX replacing FIXa; incubation 360 s (n=5-6). (E) Representative TG (n=3) initiated by 2.5 pM rTF/400 pM FVIIa WT or mutants in FVII-deficient reconstituted PRP containing 30 µg/ml CTI, 8 µg/ml anti-FVIIIa MoAb 8D4. (F) Representative TG (n=3) as in (E) but without anti-FVIIIa MoAb and without (left)/with (right) 20 µg/ml anti-FXIa MoAb O1A6. (G) Representative TG (n=3) initiated by 20 pM FIXa in FVII-deficient reconstituted PRP containing 4 µM hirugen, 30 µg/ml CTI, 20 µg/ml anti-FXIa MoAb. (H) Representative TG as in (G) but initiated by 2.5 pM rTF/400 pM FVIIa WT or E154A with (left; n=3)/ without (right; n=5) 8 µg/ml anti-FVIIIa MoAb. (I) Representative TG as in (H) but with added 3 nM FVa with (left; n=4) or without (right; n=5) anti-FVIIIa MoAb.

Intrinsic coagulation pathway activation by the nascent TF-FVIIa-FXa complex contributes to thrombin generation independently of direct extrinsic pathway function. To elucidate further how FXa generation by TF-FVIIa distinctly contributes to intrinsic pathway activation as opposed to direct extrinsic pathway TG, two FVIIa mutants were studied—T99Y and E154A. These mutants retain FX cleaving activity but display very low substrate turnover because of impaired FXa release. In a phospholipid-free assay or with phospholipid-reconstituted TF the FVIIa mutants produced an initial burst but, in contrast to FVIIa WT, could not sustain FXa generation (FIG. 14A). Remarkably, TF complexes with both mutants were comparable to FVIIa WT in supporting FXa-dependent FVIII activation, and, importantly, TFPIα at supra-physiological concentrations (10 nM) did not appreciably influence this pathway of FVIIIa generation (FIG. 14B). In marked contrast to FVIII, the FVIIa mutants failed to induce FV activation and TFPIα inhibited FVa generation induced by FVIIa WT (FIG. 14C).

Both FVIIa mutants with impaired FXa turnover supported formation of a functional FVIIIa-FIXa intrinsic tenase complex when FIXa was available, but only the FVIIa exosite mutant E154A produced FVIIIa-IXa activity when zymogen FIX was present instead (FIG. 14D). This is explained by the inability of FVIIa T99Y, unlike FVIIa E154A, to activate FIX. Thus, complementing the ability to generate FIXa, direct activation of the anti-hemophilic FVIII cofactor by nascent FXa product of TF-FVIIa enables intrinsic pathway coagulation before TFPIα inhibitory control.

These conclusions were further tested in FVII-deficient plasma-containing endogenous coagulation inhibitors—reconstituted with normal platelets as a potential source for additional TFPIα. Under these conditions, FVIIa WT, but not E154A or T99Y mutants, induced TG in the presence of a neutralizing anti-FVIII MoAb (FIG. 14E), confirming that the mutants could not directly generate thrombin in a plasma milieu. Without FVIII inhibition, FVIIa E154A induced TG with only a slight delayed as compared to WT, while FVIIa T99Y was clearly less efficient. FXIa inhibition further reduced TG by FVIIa T99Y, but affected only modestly FVIIa WT or E154A (FIG. 14F). These data are in line with the latter generating FIXa as well as FVIIIa.

To prove directly that thrombin-independent FVIII activation occurred in these reactions, the inventors first verified that the thrombin exosite blocker, hirugen, abolished FIXa-initiated TG in FVII-deficient plasma (FIG. 14G). In the presence of the same hirugen concentration, TG by mutant FVIIa E154A, not by FVIIa WT, was entirely FVIII dependent while, without FVIII inhibition, TG induced by FVIIa WT and E154A was of similar magnitude, but TG by the latter was clearly delayed (FIG. 14H). The delay was likely due to impaired direct FXa generation by the mutant FVIIa could reduce FVa cofactor generation for initial prothrombinase assembly. Indeed, adding FVa normalized the delay in FVIIIa-dependent TG by FVIIa E154A (FIG. 14I). Accordingly, adding FVa to normal PRP accelerated TF-initiated TG but not more than blocking TFPI function. These data indicated that prothrombinase activity is regulated by TFPI control of FXa generation that contributes to FV activation; and reinforce the concept that FVIII activation during TF-initiated coagulation generates FVIIIa-FIXa intrinsic tenase activity independently of thrombin feedback reactions and escaping TFPI control.

Figure 15:
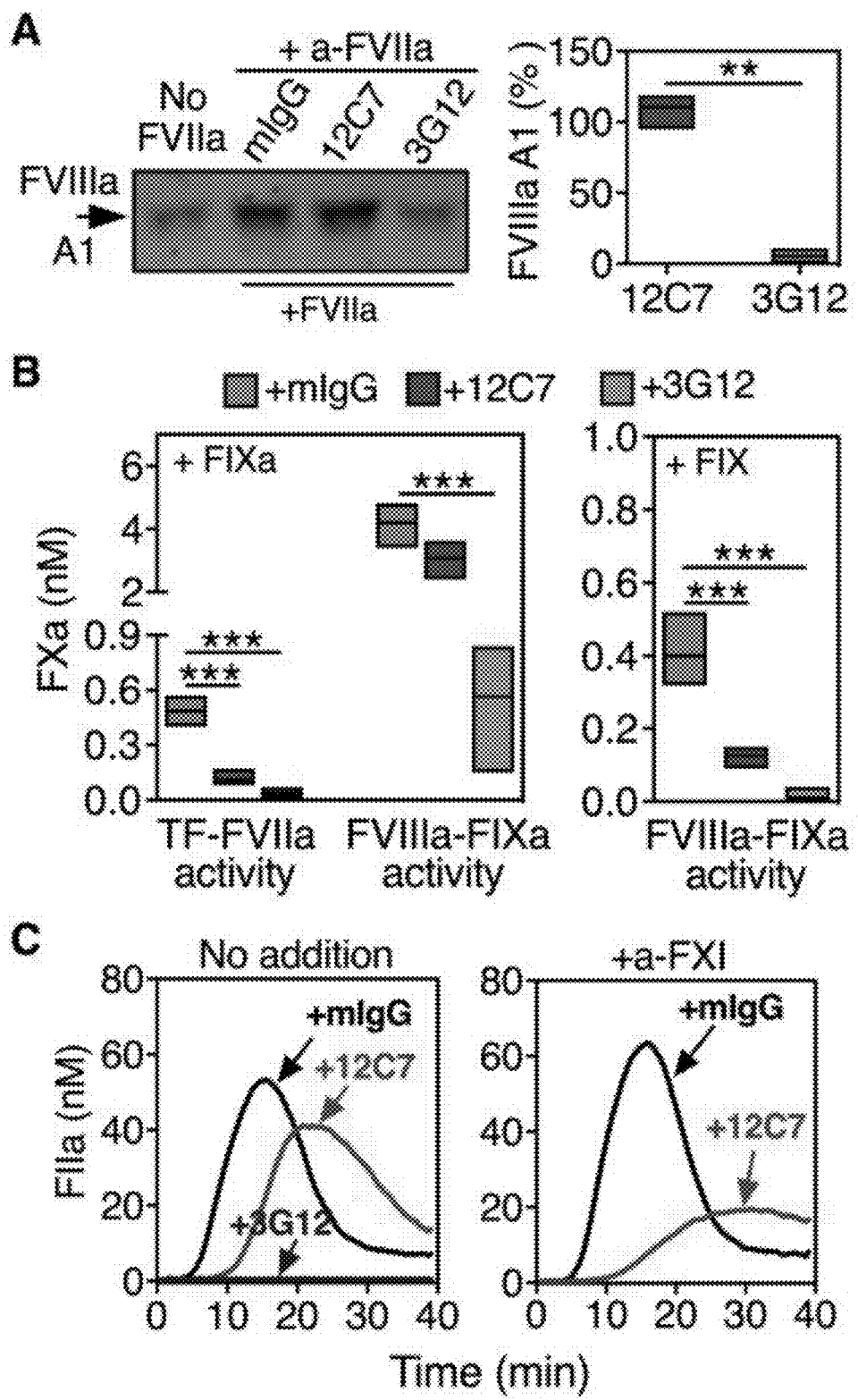
FIG. 15 illustrates, in accordance with embodiments herein, Anti-FVIIa MoAb 12C7 mimics FVIIa Y99A functional properties. (A) Left. Representative immunoblot showing the effect of anti-FVIIa MoAbs 3G12 and 12C7 (20 µg/ml) on TF-dependent FVIIIa generation in reactions including 50 pM rTF, 200 pM FVIIa, 135 nM FX, 3.5 nM FVIII, 3 nM FV, 200 nM lepirudin incubated for 120 s at 37° C. Right. Quantification of the data on the left (n=3; min-to-max floating bars, line at the mean); differences were evaluated by Welch-corrected two-tailed t-test. (B) Anti-FVIIa MoAb 12C7—but not 3G12—preserves FVIIIa-dependent FXa generation by 10 nM FIXa (left; n=3), but not 90 nM FIX (right; n=3-5), in reactions containing 50 pM rTF, 200 pM FVIIa, 700 pM FVIII, 3 nM FV, 135 nM FX, 10 nM TFPIα, 200 nM lepirudin and 2.5 mM $CaCl_2$ incubated 180 or 360 s, respectively, 37° C. Anti-FVIIa MoAbs or control mouse IgG were added at 20 µg/ml. Results (min-max floating bars, line at the mean) were analyzed by ANOVA/Tukey tests. ***P<0.001. (C) Representative thrombograms (n=2) showing the effect of anti-FVIIa MoAbs 3G12 and 12C7 (20 µg/ml) on 1.2 pM rTF-induced TG in normal PRP with CTI (30 µg/ml) and without (left) or with (right) addition of anti-FXI MoAb O1A6 (20 µg/ml) blocking FIX activation by FXIa.

The inventors then screened a library of MoAbs to FVIIa to identify a proof of principle inhibitor that could recapitulate the shift in functional properties—loss of efficient FXa and FIXa generation, but not of FVIII activation—seen with the FVIIa mutant T99Y. In contrast to the fully inhibitory MoAb 3G12, antibody 12C7 had no effect on FVIII activation (FIG. 15A). Moreover, it had no significant effect on the generation of intrinsic tenase activity when FIXa was present, but it markedly inhibited when FIX was supplied instead (FIG. 15B). MoAb 12C7 attenuated TG in PRP but, as seen with FVIIa T99Y, rendered TG FXIa-dependent (FIG. 15C). Thus, results with mutant FVIIa molecules and inhibitory antibodies concordantly show that the TF-FVIIa complex can initiate intrinsic and extrinsic coagulation pathways in distinct reactions.

Figure 16:
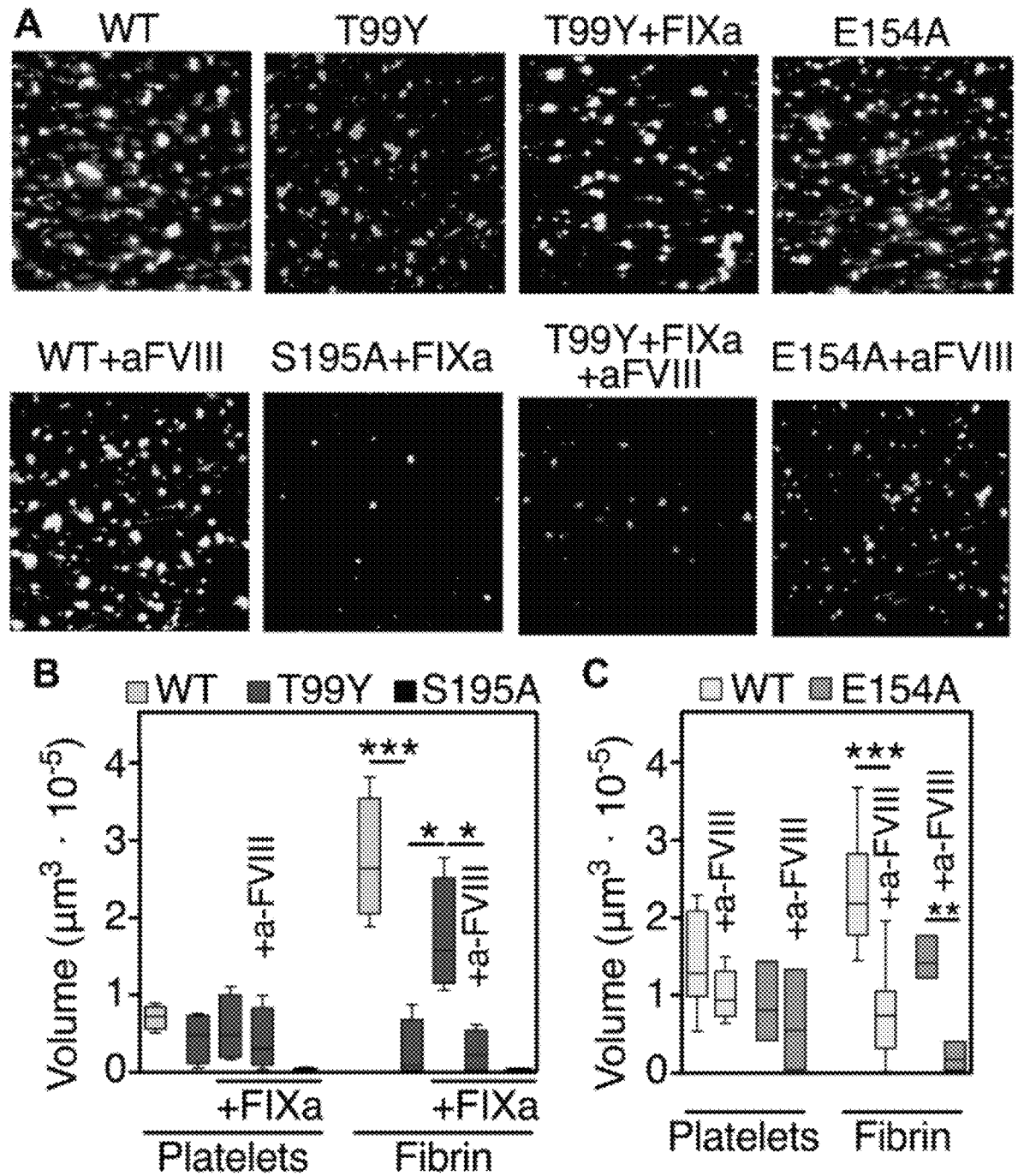
FIG. 16 illustrates, in accordance with embodiments herein, FVIIIa-dependent thrombus formation induced by the TF-FVIIa initiation complex in flowing blood. (A) Blood reconstituted with washed type 0 blood cells added to the original count into FVII-deficient citrated PPP with 200 pM WT or mutant FVIIa and without/with the inhibitory anti-FVIII MoAb C5 (25 µg/ml) was recalcified to 1.29 mM $Ca^{2+}$ and perfused for 3.5 min at 300 $s^{-1}$ wall shear rate. Where indicated, FIXa (20 pM) was added to blood. Representative confocal images are shown with superimposed green (platelet aggregates and leukocytes) and red (fibrin) fluorescence channels. Image side=312 µm. (B) Quantification of the volume of platelet aggregates and deposited fibrin after adding FVIIa WT, T99Y or S195A without/with anti-FVIII MoAb (n=4-6 for the different conditions). (C). As in B, but after adding FVIIa WT or E154A (n=3-8 for the different conditions). Results in (B) and (C)—shown as 25th-75th percentile bars, min-to-max whiskers, line at the median; or min-to-max floating bars, line at the mean when n≤3—were evaluated by the ANOVA/Tukey tests; *P<0.05, P<0.01, *P<0.001.

Intrinsic pathway activation by TF leads to fibrin formation in flowing blood. To evaluate whether TF-FVIIa can initiate thrombus formation in flowing blood ex vivo when direct initial thrombin generation is limited, TF was surface-immobilized at a low concentration sufficient for FVIII-dependent fibrin formation at a wall shear rate of 300 s$^{-1}$. Under these conditions established with WT FVIIa, FVIIa T99Y had impaired thrombogenic activity despite supporting more platelet adhesion than inactive FVIIa S195A (FIG. 16A, B). Addition of 10 pM FIXa to blood containing FVIIa T99Y, but not to blood containing inactive FVIIa S195A, restored FVIII-dependent fibrin formation (FIG. 16A, B). In contrast, mutant FVIIa E154A, which is as defective as T99Y in direct TG (see FIG. 14E), supported FVIIIa-dependent thrombus formation similar to FVIIa WT when added without FIXa to FVII-deficient reconstituted blood (FIG. 16A, C). This confirmed that the nascent FXa product of TF-FVIIa can directly generate FVIIIa functioning in the intrinsic tenase complex with the potential to enhance hemostasis in low TF environments with limited direct TF-dependent thrombin generation activating feedback loops.

Example 35

Discussion

The findings presented here delineate a novel function of the extrinsic TF-FVIIa complex, namely providing selective feed-forward activation of the FVIII anti-hemophilic cofactor independently of thrombin feedback loops (FIG. 1B). This specific reaction of nascent FXa escapes control by physiologic coagulation inhibitors in PRP or TFPIα in purified systems. Together with the previously recognized capacity of TF-FVIIa to generate the FIXa anti-hemophilic protease, direct FVIII activation completes a pathway to FVIIIa-FIXa intrinsic tenase activity fully integrated within TF/FVIIa-initiated coagulation and preceding the canonical direct activation of the common coagulation pathway.

Nascent TF-FVIIa-FXa generates FVIIIa facilitating the formation of intrinsic tenase but without providing FVa for prothrombinase activity. Generating the latter requires FXa undocking from TF-FVIIa, thus exposing free FXa to inhibitory control. Therefore, the newly identified TF-FVIIa-FXa function allows for accumulation of active pro-hemostatic anti-hemophilic FVIIIa cofactor without increasing pro-thrombotic FVa. This may be of relevance for targeted FXa anti-coagulants that, with comparable anti-thrombotic potency, have a lesser impact on hemostasis than vitamin K antagonists. Of note, such a mechanism is independent of thrombin feedback reactions and FXI activity and may thus support hemostasis during treatment with thrombin inhibitors or recently validated strategies targeting FXI.

Selectivity for cofactor activation indicates distinct functional properties of FXa in complex with or released from TF-FVIIa. While coagulation cofactor-enzyme complexes are typically geared towards efficient substrate turnover for rapid thrombin generation, throughout evolution the TF initiation complex appears to have preserved mechanisms favoring its stability. FX interacts with TF-FVIIa through an extended interface that is minimally affected by zymogen to enzyme transition. In this interface, FVIIa residue E154, conserved across species, transmits conformational changes from the substrate-occupied active site of the protease and may thereby regulate subsequent product release. Elimination of this conformational switch was sufficient to segregate macromolecular substrate FX activation and product FXa turnover by TF-FVIIa. Thus, mutant FVIIa E154A helped inform on direct FVIII activation by nascent FXa associated with TF-FVIIa as well as the contribution of this novel pathway to thrombin generation and thrombogenesis in platelet-rich plasma and whole blood under flow.

Stability of the TF coagulation initiation complex likely represents the evolutionary advantage of preserving key signaling roles of TF-FVIIa-FXa that link coagulation activation and innate immunity. In line with efficient FVIII activation, FVIIa T99Y is fully functional in mediating TF-FVIIa-FXa activation of protease activated receptor (PAR) 2. Moreover, as seen for FVIIIa generation, resistance to functional inhibition by TFPIα is also an important feature of PAR signaling induced by TF-FVIIa-FXa in endothelial cells. This signaling complex is additionally stabilized by recruitment of the FXa binding partner, endothelial protein C receptor (EPCR), in mouse and man. A key innate immune signaling role for the TF-FVIIa-EPCR complex recently emerged in dendritic cells, where it is essential for toll like receptor 4 induction of interferon-regulated genes. Negative regulation of this pathway by the alternative EPCR ligand, activated protein C, utilizes the canonical anticoagulant cofactor functions of FV and protein S. Thus, these and other non-traditional functions of the coagulation system likely utilize the same mechanistic features that simultaneously serve diverse roles in immunity, hemostasis and injury repair.

The disclosure herein provides the biochemical bases for defining distinct roles of TF in supporting hemostasis or contributing to thrombosis. One can envision application of mutants of FVIIa or the described antibody reagents to define the partial functions of TF in triggering thrombogenesis directly or provide activation of the intrinsic pathway of relevance for hemostasis. Ultimately, this should lead to the possibility of selectively assessing the effects of recent and future new anticoagulants on the dual roles of TF in hemostasis and thrombosis. The novel concepts on coagulation presented here may also have implications for the development and evaluation of hemostatic agents, providing protection from severe bleeding complications while avoiding adverse thrombotic complications in patients with underlying vascular pathologies.

Example 36

Clotting Activity

Materials. Innovin rTF (Siemens Healthcare Diagnostics) was calibrated against a reference lot (#53691; 13.9 nM rTF) using a FXa generation assay including varying rTF concentration, 100 pM FVIIa and 135 nM FX. The reference lot contained 101.4 μM procoagulant phospholipids as measured by prothrombinase activity calibrated with 80% phosphatidylcholine (PC)/20% phosphatidylserine (PS) mol/mol phospholipid vesicles (Avanti Polar Lipids, Alabaster, AL), sonicated in 10 mM 4-(2-hydroxyethyl) piperazine-1-ethanesulfonic acid (HEPES), 0.15 M NaCl, pH 7.4. Thrombin-generated FVIIIa was prepared incubating 190 nM FVIII, 19 nM FIIa and 5 mM $CaCl_2$ for 30 s at 37° C., followed by 36 nM lepirudin (recombinant [Leu1-Thr2]-63-desulfohirudin; Refludan, Bayer Corp, Pittsburgh, PA) to neutralize thrombin. Normal PPP was prepared locally by centrifugation of venous blood containing 10.9 mM trisodium citrate at 1,500 g for 10 minutes at 25° C. PPP from patients with severe congenital deficiency (<1%) of FVII, FVIII or FIX was from George King Bio-Medical (Overland Park, KS); FIX-deficient PPP pre-pared by immunoaffinity depletion of normal plasma was from Haematologic Technologies.

Blood perfusion experiments. Glass coverslips treated with 0.2 mg/ml poly-L-lysine for 6 h at 37° C. were coated with rTF for 18-20 hours at 37° C., rinsed with buffered-saline and assembled in a rectangular flow chamber with a 125 μm-high silicon gasket. Venous blood was collected into final 10.9 mM trisodium citrate using a plastic syringe. $CaCl_2$ was added to obtain 1.29 mM $Ca^{2+}$ before perfusion at a wall shear rate of 300 s−1 maintained with a syringe pump (Harvard Apparatus, Holliston, MA). For experiments with WT and mutant FVIIa, cells in citrated group 0 blood, supplemented with 50 μg/ml CTI and apyrase (10 U/ml ADPase activity), were washed free of plasma by sequential cycles of centrifugation at 1500 g for 7 min followed by resuspension. In the first cycle, plasma was replaced with an equal volume of calcium-free Tyrode buffer, pH 6.5, containing 5 U/ml apyrase; then, with buffer and 1.25 U/ml apyrase; and, finally, with human FVII deficient plasma up to the original blood volume. Hematocrit and platelet counts of reconstituted and native blood were within ±10%. Platelets/leukocytes were visualized by incorporation of quinacrine hydrochloride (mepacrine; Sigma) added at a concentration of 10 μg/ml and incubated for 15 min at room temperature before perfusion. Fibrin was visualized by binding of mouse monoclonal IgG (HB-8545; American Type Culture Collection, Manassas, VA) labeled with Alexa Fluor 546 (Invitrogen) and used at 50 µg/ml concentration in blood; the anti-body interacts with the human/mouse fibrin β but not fibrinogen BP chain.

TG analysis in human native or reconstituted PRP. PRP was prepared from blood containing 10.9 mM trisodium citrate centrifuged at 250 g for 10 min at 25° C. Platelets were adjusted to $180 \cdot 10^3/\mu l$ by dilution with homologous PPP obtained from PRP centrifuged at 1,500 g for 10 min at 25° C. Reconstituted PRP was prepared with washed platelets isolated from normal PRP mixed with ⅕th volume of acid-citrate-dextrose (71 mM citric acid, 85 mM trisodium citrate, and 111 mM dextrose, pH 4.5) and 5 U/ml apyrase. After centrifugation at 1,500 g for 10 min, the platelet pellet was resuspended into PPP either normal or lacking a specific coagulation fac-tor and in which 30-50 µg/ml CTI had been added in advance; the final platelet count was $180 \cdot 10^3/\mu l$. Fluorescence intensity in reactions generated by thrombin cleavage of the substrate Gly-Gly-Arg-AMC was measured continuously at 37° C. for up to 40 min in a spectrofluorometer. The thrombin burst slope (nM/min) was calculated by dividing the peak height of thrombin concentration by the time from induction to its occurrence minus the lag time, defined as the time from induction to 3 nM thrombin generated. The endogenous thrombin potential (ETP, i.e., total generated thrombin activity) was determined from the area under the TG curve. The discontinuous 2-stage TG assay was initiated by adding 0.15 pM rTF and 18 mM $CaCl_2$ into FVII-deficient PRP with 30 µg/ml CTI and 400 pM WT FVIIa or iFVIIa without/with 20 pM FIXa. In other experiments, TG was induced by TF-iFVIIa-FXa-TFPI or TF-iFVIIa-FXa-NAPc2. Stable complexes were pre-formed by incubating 5 nM FXa, 10 nM TF, 10 nM iFVIIa and 40 nM TFPI or NAPc2 in the presence of 2.5 mM $CaCl_2$ for 120 s at 37° C. Complexes were added into FVII-deficient PRP, followed by incubation for 8 min at 37° C.

Coagulation activation in reactions with purified components. FVIII activation by stable FXa complexes with TF-FVIIa was tested in reactions containing FVIII, FV and lepirudin with or without TFPIα, with incubation for 30-120 s at 37° C. Stable complexes with FXa as the only active protease were prepared in reactions incubated for 120 s at 37° C. including: 1) 200 pM FXa, 400 pM rTF, 500 pM iFVIIa, 40 nM NAPc2 and 2.5 mM $CaCl_2$; 2) 100 pM FXa, 50 pM rTF, 100 pM iFVIIa, 5 nM NAPc2 and 2.5 mM $CaCl_2$. The effect of added FVa on FVIIIa generation by free FXa was tested in reactions with 10 pM FXa incubated with 50 pM rTF and substrates for 180 s at 37° C. The inhibitory effect of hirugen on FVIIIa generation by FIIa was tested in reactions with 0.5 nM FIIa incubated with 50 pM rTF and FVIII for 180 s at 37° C.

Substrate turnover by TF-FVIIa was evaluated from FXa generation in reactions without phospholipids containing 10 nM FVIIa, 1 µM FX and 2 µM soluble rTF1-218. FVa was titrated in a prothrombin activation assay in which 10 pM FXa was incubated with 1 µM prothrombin 50 pM rTF and 700 pM FVIII for 180 s.

Activation of FIX by TF-FVIIa was tested in reactions containing 150 nM FIX with 50 pM rTF, 200 pM FVIIa and 2.5 mM $CaCl_2$ incubated for 30 min at 37° C. After terminating reactions with 10 mM EDTA, FIXa activity was determined in the presence of ethylene glycol (37%, volume/volume) by kinetically measuring amidolytic activity with the chromogenic substrate CH3SO2-(D)-CHG-Gly-Arg-para-nitroanilide•AcOH (Pefachrome FIXa, Pentapharm, Basel, Switzerland; 1 mM). The calibration curve of FIXa was constructed with known concentrations of FIXa.

Measurement of FVIIIa clotting activity. Aliquots of reactions in which FVIIIa was generated were added into FVIII-deficient plasma (George King Bio-Medical) and then mixed with 10 nM FIXa, 20 µM PL and 8 mM $CaCl_2$. FVIIIa clotting activity was quantified using calibration curve constructed with known concentrations of thrombin-activated FVIIIa.

Ferric chloride-induced thrombosis in mice. Time to first occlusion after injury is that required for a decrease of blood flow to <10% of that measured in the uninjured artery. Flow index is the ratio between blood volume flowing through the injured artery in 30 min (integration of flow measured in ml/min and sampled every second) and that expected in the uninjured artery (calculated from the flow measured in 1 min before injury multiplied by 30).

Example 37

Highly Sensitive and Rapid Thrombin Generation Assay

Disclosed herein are compositions and methods of highly sensitive and rapid thrombin generation assay for selectively determining the initial small amounts of thrombin produced in plasma by anti-hemophilic intrinsic pathway, enabling more precise assessment of congenital and acquired bleeding disorders and thrombotic complications Blood coagulation enzyme thrombin (FIIa) is responsible for preventing hemorrhage and stopping spontaneous bleeding (i.e., "hemostasis") by forming a stable fibrin clot, while hyper-generation of FIIa may cause lethal vascular disease "thrombosis" including heart attack and stroke. In the current scheme on FIIa generation (TG), the extrinsic pathway complex of tissue factor (TF) with active factor (F) VIIa initiates a cascade of proteolytic reactions yielding FXa in a primary phase that forms prothrombinase complex with active cofactor FVa, generating initial small amounts of FIIa. The initially produced FIIa amplifies FIIa generation (TG) by enhancing the prothrombinase complex activity, leading to a burst of generated FIIa in a secondary phase. The inventors have discovered that the molecular mechanisms, by which the initial FIIa enhances the activity of prothrombinase complex, is as follows: 1) the initial FIIa triggers platelet activation providing active phospholipid surface essential for prothrombinase activity; 2) FIIa increases prothrombinase complex formation by directly activating FV to FVa; 3) FIIa promotes the generation of FXa by activation of the intrinsic FVIIIa-FIXa pathway. FIIa directly activates essential cofactor FVIII to active FVIIIa for protease FIXa. In addition, FIIa indirectly activates FIX to FIXa mediated by activation of zymogen FXI to enzyme FXIa that in turn activates FIX to FIXa. Finally, large amounts of generated FIIa convert fibrinogen to fibrin that is essential for hemostasis and thrombosis. Thus, initially generated FIIa functions as a determinant of the extent of blood coagulation, suggesting that to determine initial TG may provide a diagnostic approach for more precise assessment of bleeding disorders and thrombotic complications.

The presently disclosed TF-dependent FVIII activation pathway, wherein FVIII activation mechanism is mediated by nascent FXa in TF-FVIIa-FXa initiation complex prior to feedback activation of FVIII, has a key role in the initial TG in plasma. Based on novel mechanistic concept, the inventors have disclosed the novel compositions and methods for determination of the FVIIIa-dependent initial TG in plasma. In the assays, TG is initiated by the combined addition of extremely low concentrations (e.g., 150 fM) of re-lipidated recombinant TF (rTF) and FIXa (e.g., 200 pM), followed by continuously monitoring the generated FIIa using a FIIa substrate for 40 min at 37° C. (so-called "continuous TG assay"). In the continuous TG assay, FVIIIa is produced by TF-FVIIa-FXa initiation complex and generated FVIIIa promotes TG by increasing FIXagenerated FXa. Thus, this TG assay provided a useful approach for defining a relationship of functional FVIIIa levels with bleeding episodes in hemophilia A patients with congenital/acquired FVIIIa-defects and subjects treated with ant-thrombotic therapies.

Moreover, the inventors have disclosed another assay that provides for rapid determination of the amount of TG. In one embodiment, this new assay may provide a standardized and automated method for determining TG in a patient. The inventors have disclosed novel components and methods of rapid and highly sensitive TG assay for selectively determining the initial small amounts of FIIa produced by the anti-hemophilic intrinsic pathway. This novel assay allows more precise and automated assessment of congenital and acquired bleeding disorders. The assay may be utilized as clinical diagnostic laboratory tests replacing conventional clotting assays.

Figure 17:
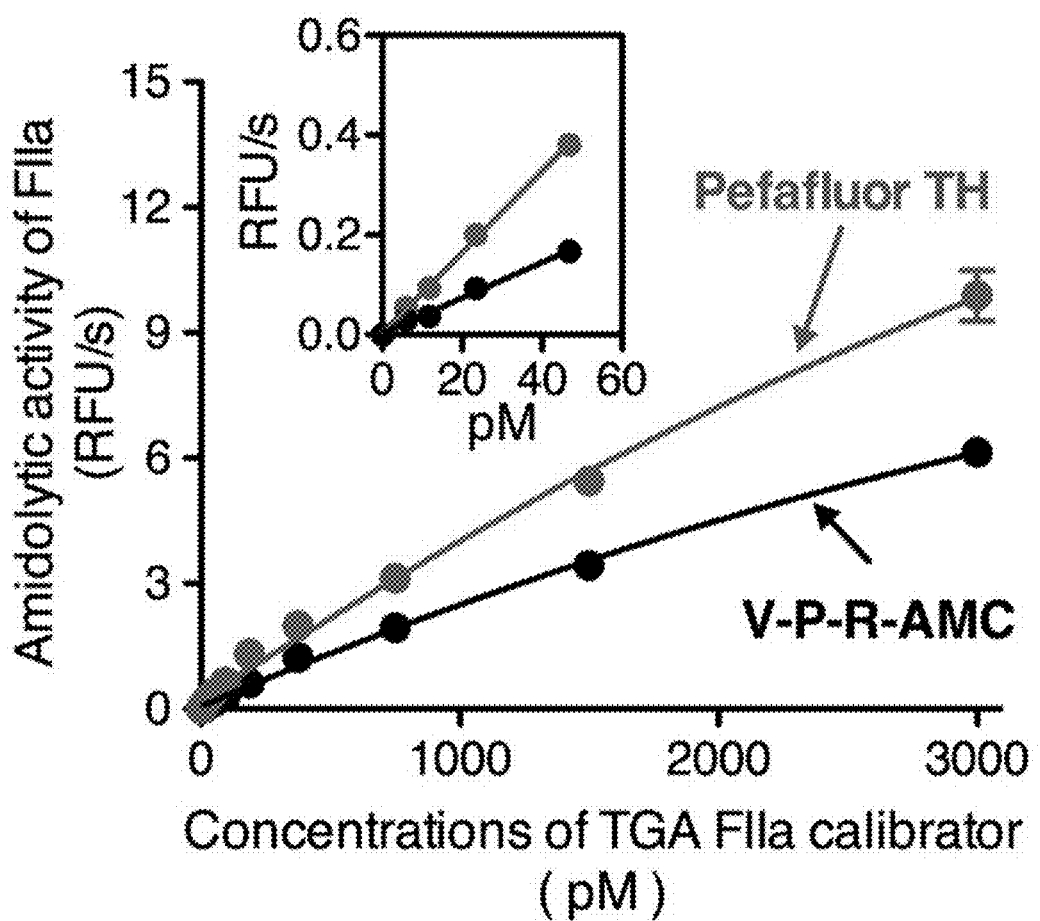
FIG. 17 illustrates, in accordance with embodiments herein, calibration curves constructed with a FIIa calibrator using FIIa substrates (50 µM).
Figure 18:
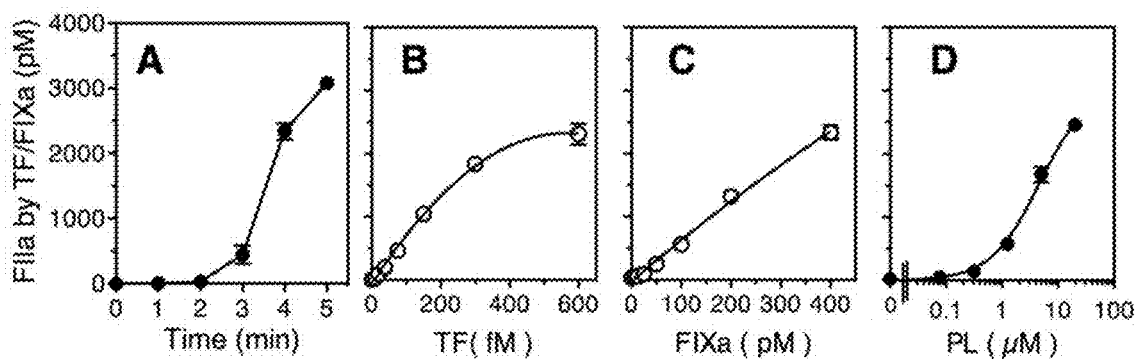
FIG. 18 illustrates, in accordance with embodiments herein, discontinuous 2-stage assay of initial TG. Initial TG was induced in normal platelet-poor plasma by combined addition of rTF and FIXa, followed by incubation for up to 5 min (except for 3 min in panels B-D) at 37° C. (A) TG by 150 fM rTF, 200 pM FIXa and 1.3 µM PL. (B) Titration of added rTF in TG by 200 pM FIXa with 1.3 µM PL. (C) Titration of added FIXa in TG by 150 fM rTF with 1.3 µM PL. (D) Enhancing effect of added PL on TG by 150 fM rTF and 200 pM FIXa. Each data denotes mean±SEM of 3 experiments.
Figure 19:
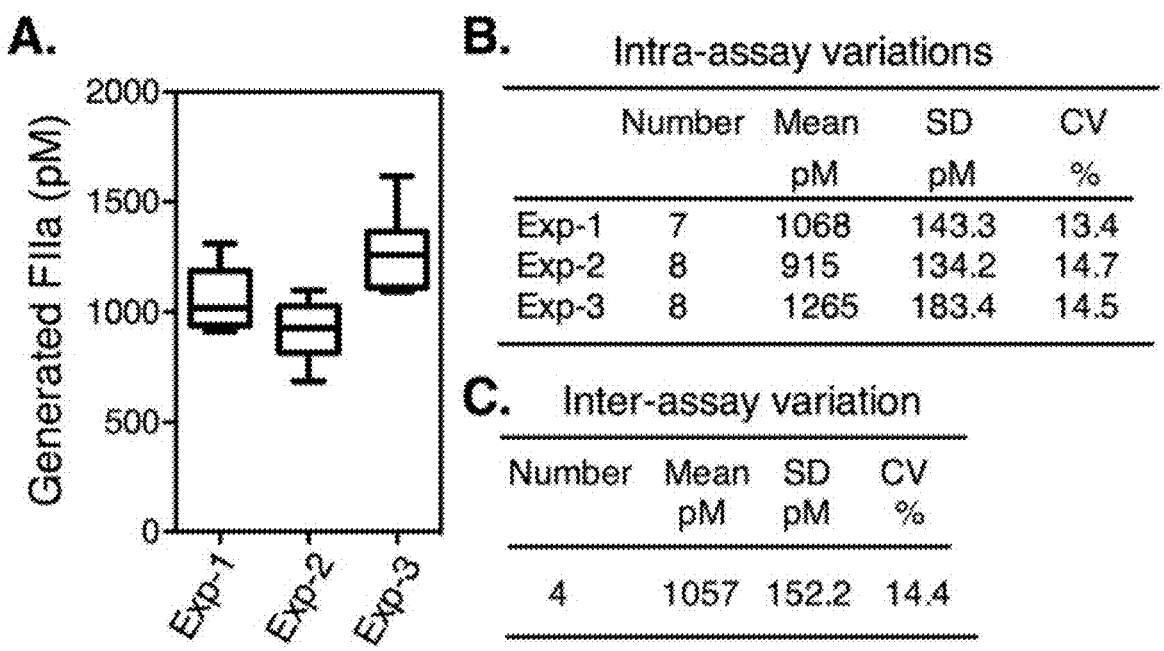
FIG. 19 illustrates, in accordance with embodiments herein, assay validation by testing reproducibility of the TG assay. TG was induced in pooled normal plasma by 150 fM rTF, 200 pM FIXa and 1.3 µM PL for 3 min at 37° C. (A and B) Determination of intra-assay variations. Results (n=7-8) in panel A are shown as 25th-75th percentile bars with min/max whiskers and line at the median of three independent experiments. The Table in panel B indicates that intra-assay precision is high due to low coefficient of variations (CV) with <15%. (C) Determination of inter-assay variation (n=4). Inter-assay CV value was also observed to be <15%.

To establish highly sensitive TG assay method, the inventors made a screening of FIIa substrates with high affinity and turnover rate by determining kinetic parameters and then constructed a calibration curve with known concentrations of a FIIa calibrator. In the studies, they found two fluorogenic substrates H-D-cyclohexyl-alanyl-alanyl-argininyl-amidomethylcoumarin (AMC) (Pefafluor TH) and butyloxycarbonyl-valyl-prolinyl-argininyl-AMC (V-P-R-AMC) were suitable for quantifying much low concentrations of FIIa activity with a detection limit of ~5 pM (FIG. 17). Initial TG was measured with "discontinuous 2-stage assay" using the high sensitive substrate. Briefly, TG was initiated by combined addition of rTF and FIXa with 18 mM $CaCl_2$) into plasma, followed by incubation for up to 5 min at 37° C. After incubation, reactions were terminated with 20 mM EDTA and generated FIIa was measured using the highly sensitive FIIa substrate Pefafluor TH or V-P-R-AMC. In the assays, combined addition of 150 fM rTF and 200 pM FIXa time-dependently produced FIIa in normal platelet-poor plasma (PPP) prepared from healthy donors (FIG. 18A). Titration experiments with rTF (9.4-600 fM) and FIXa (6.3-400 pM) showed a dose-dependency of two initiators in initial TG (FIGS. 18B,C). Further experiments indicated that an addition of phospholipid (PL) vesicles (0.08-20 μM) consisting of 80% phosphatidylcholine/20% phosphatidylserine (mol/mol) dramatically enhanced initial TG in PPP (FIG. 18D). To further validate the assay method, reproducibility of the TG assay method was examined by determination of intra-assay and inter-assay coefficient of variations (CV) using manual assay protocol. Both intra-assay and inter-assay CV values were calculated to be <15% (FIG. 19), indicating that this is a reliable TG assay method.

Figure 20:
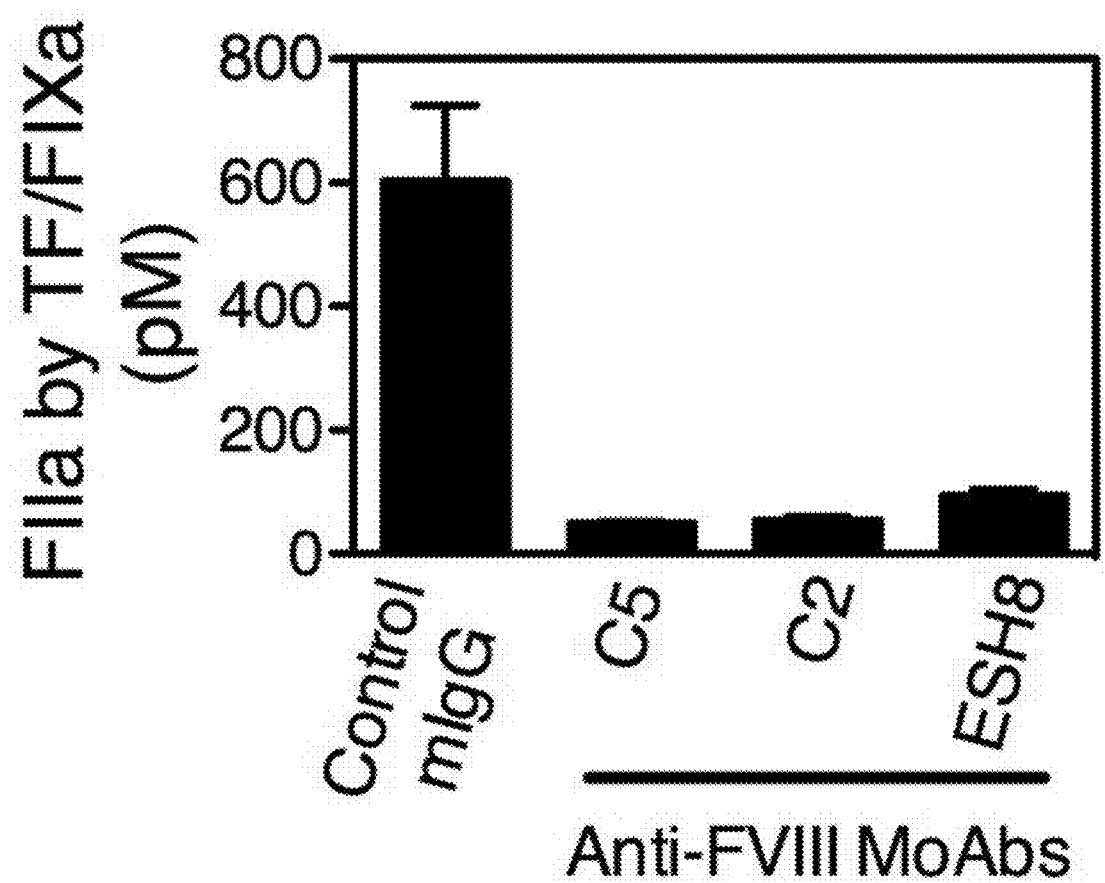
FIG. 20 illustrates, in accordance with embodiments herein, effect of anti-FVIII monoclonal antibodies (MoAbs) on initial TG in normal PPP by 150 fM rTF/200 pM FIXa and 1.3 µM PL. MoAbs were added at 125 nM. Each column indicates mean±SEM (n=3) of generated FIIa after 3 min of incubation.
Figure 21:
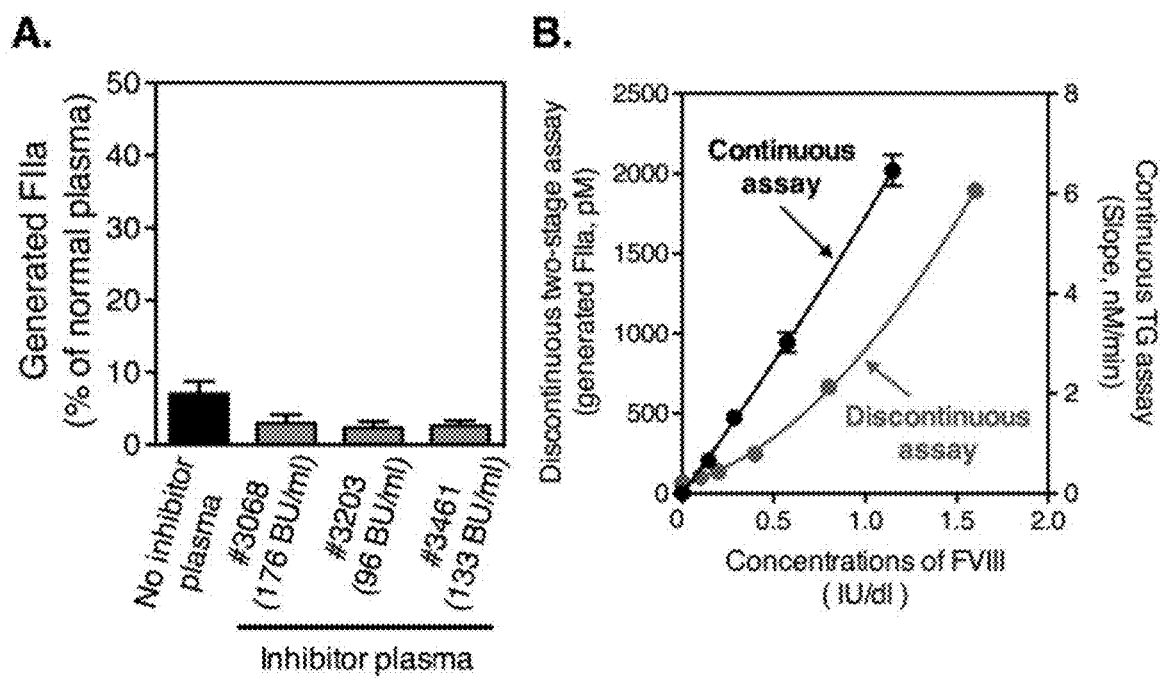
FIG. 21 illustrates, in accordance with embodiments herein, TG assays in FVIII-deficient PPP without or with anti-FVIII inhibitors. (A) Initial TG in discontinuous 2-stage assay was induced by adding 150 fM rTF/200 pM FIXa and 5 µM PL, followed by incubation for 5 min at 37° C. Each column indicates mean+SEM (n=3) of generated FIIa. (B) Comparison of dose-response curve of added FVIII in TG in FVIII-deficient plasma by discontinuous 2-stage assay with that by continuous assay. Continuous TG was also induced by adding 150 fM rTF/200 pM FIXa and 5 µM PL, followed by incubation for 40 min at 37° C.

The FVIIIa-dependent TG was verified by testing the effect of added anti-FVIII inhibitory monoclonal antibodies (MoAbs) on initial TG in normal PPP induced by 150 fM rTF/200 pM FIXa with PL (FIG. 20). Initial TG was examined in FVIII-deficient PPP prepared from hemophilia A patients. Compared to initial TG in normal PPP induced by adding TF/FIXa and PL, much less TG was observed in PPP from patients without and with anti-FVIII inhibitor antibodies (96, 133, and 176 Bethesda Unit/ml) (FIG. 21A). One Bethesda Unit is defined as the amount of an inhibitor that neutralizes 50% of 1 unit of FVIII activity in normal plasma. More importantly, when FVIII-deficient PPP without inhibitor was supplemented with plasma derived FVIII (0.1-1.6 IU/dl), initial TG was enhanced in a dose-dependent fashion (FIG. 5B). The results clearly indicate that the discontinuous 2-stage assay of initial TG specifically determines the FVIIIa-dependent TG and that it has the similar sensitivity in detection of FVIIIa activity in plasma as the previously disclosed continuous TG assay (FIG. 5B). Thus, this assay can be used to more accurately and rapidly predict bleeding risk in severe hemophilia A patients, thus improving replacement therapy with FVIII products.

Figure 22:
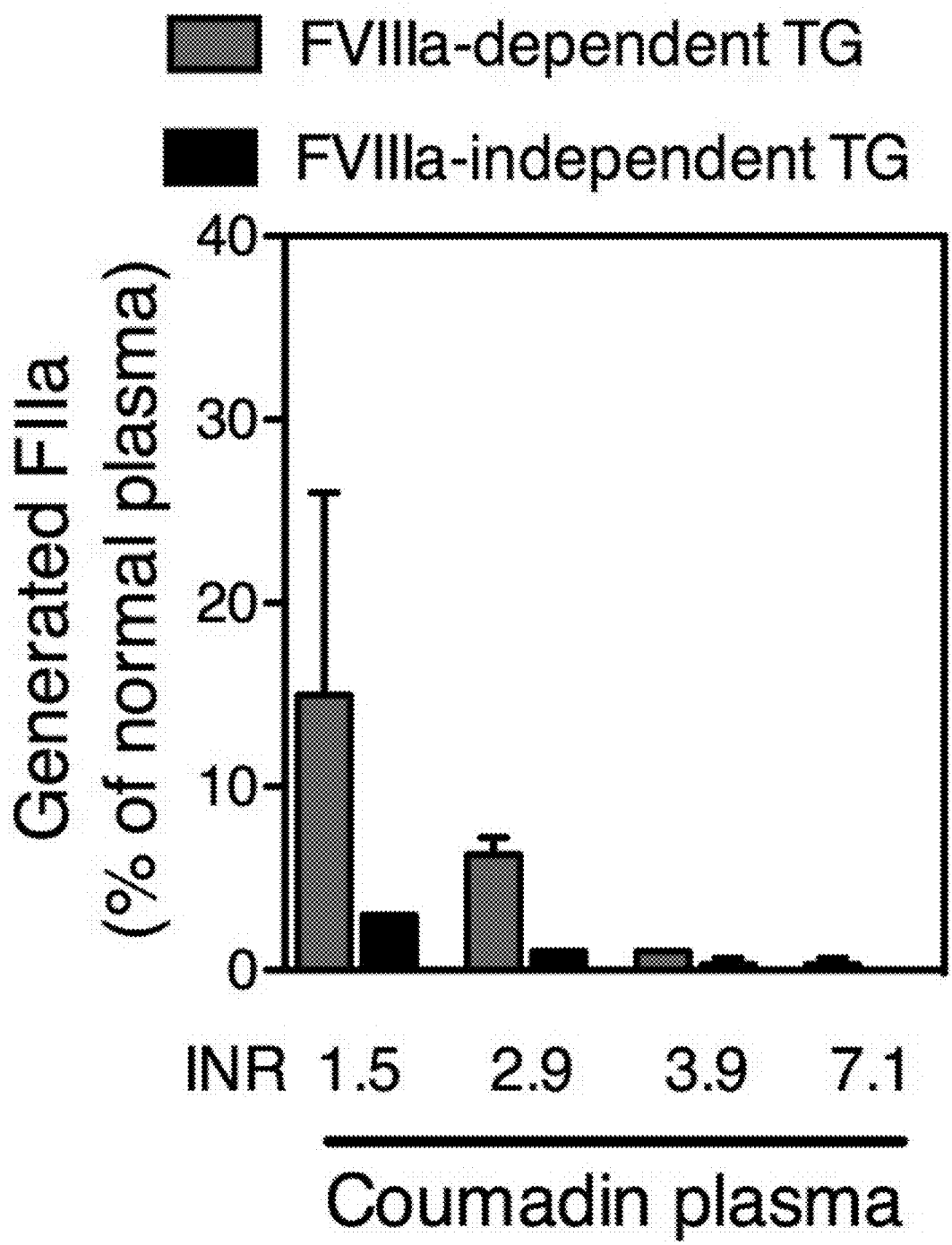
FIG. 22 illustrates, in accordance with embodiments herein, FVIIIa-dependent and -independent TG in plasma from Coumadin-treated patients. FVIIIa-dependent TG was induced by adding 150 fM rTF/200 pM FIXa with 1.3 µM PL, while FVIIIa-independent TG was by 1.2 pM rTF with 1.3 µM PL. Each column indicates mean+SEM (n=3) of generated FIIa after 3 min of incubation.

Coumadin (warfarin), vitamin K antagonist is widely used to prevent thrombotic diseases. Because Coumadin treatment may cause serious and fatal hemorrhage, patients are regularly monitored by International Normalized Ratio (INR) test. The INR values are determined by a conventional clotting assay (so-called prothrombin time assay) using rTF. To clarify whether the INR values correlate with initial FVIIIa-dependent TG, initial TG in PPP was tested with different INR values from Coumadin-treated patients by adding rTF and FIXa. Initial FVIIIa-dependent TG was reduced to ~15% and ~5% of normal plasma in patient plasma with 1.5 and 2.9 of INR respectively; although TG was completely abolished in plasma with much higher INR values (FIG. 22). In contrast, FVIIIa-independent TG, which was determined by adding 1.2 pM rTF alone without FIXa into plasma, was abolished even at lower INR. The results suggest that in contrast to FVIIIa-independent TG directly by the TF pathway, FVIIIa-dependent TG by the anti-hemophilic intrinsic pathway may be sustained in Coumadin-treated patients, presumably contributing to hemostasis. Thus, the assay method invented here may help a personalized prediction of bleeding risk in patients. Combined assays of FVIIIa-independent and dependent TG may also provide a more refined determination of drug dosage for inhibiting thrombosis by determining FVIIIa-independent TG while preserving sufficient hemostatic function by determining FVIIIa-dependent TG. In summary, the instant disclosure offers the diagnostic testing kit and methods of highly sensitive assays for determining initial small amounts of FIIa produced in plasma and blood specifically by the anti-hemophilic intrinsic pathway via the FVIIIa-FIXa complex. The kit is composed of coagulation factors such as rTF, FIXa and PL and high sensitive FIIa substrate. The novel assay would allow a more accurate characterization of bleeding phenotypes and prediction of bleeding risk in congenital and acquired hemophilia A patients and individuals with anti-thrombotic treatment.

Conventional clotting assays such as the prothrombin time (PT) and the activated partial thromboplastin time (aPTT) are widely used as automated laboratory tests, but they have critical disadvantage of less sensitivity in characterizing minor changes of coagulation reactions and in predicting the risk of hemorrhage and thrombogenesis in patients. On the other hand, continuous FIIa generation (TG) test originally developed by Hemker's laboratory is sensitive enough in such patients, helping the diagnosis of hypercoagulable states and hemorrhagic diathesis. However, differing from clotting assays, the assay has no strong benefit of being automation friendly and well standardized since the assay method is much time consuming (e.g., 40-60 min) and it has high intra- and inter-assay variations. The assay also requires a large quantity of FIIa substrate due to low affinity causing greater cost of producing the diagnostic kits and higher price of selling products. Thus, the application of continuous TG assays to clinical decisionmaking is still hampered by the issues.

The novel "discontinuous 2-stage TG assay method" disclosed herein overcomes the issues and it offers rapid (within 10 min) and easier TG assays with high sensitivity in verification of the altered coagulation factors and reactions associated with bleeding by selectively determining the initial small amounts of FIIa produced by the anti-hemophilic intrinsic pathway. For instance, the assays and methods disclosed herein can be used to determine the levels of FVIII in severe hemophilia A patients (see FIG. 21B) and it may be useful for monitoring treatment with FVIII concentrates and for assessment of concentrate potency. The assay can also be utilized to identify FVIII variants with improved functionality and/or increased stability and for screening novel hemostatic agents with improved efficacy and safety for hemophilia A treatment. In addition, the discontinuous TG assay disclosed herein may allow accurately prediction of thrombotic disorders by detecting higher initial TG in patients. Altogether, the inventive TG assays should be utilized as clinical diagnostic laboratory tests capable of replacing conventional clotting assays.

The instantly disclosed assay is based on the discovery of TF initiation complex-driven FVIII activation pathway in plasma, which supports the amplification of FIIa generation in an initial and primary phase of coagulation reactions essential for hemostasis. In contrast to classic and conventional FVIII activity assays, therefore, the present assay has the additional advantage of assessing a previously unrecognized pathway of the physiological FVIII activation process. The highly sensitive methods may thus be useful for identifying factors and substances inhibiting or promoting FVIII activation and for a more accurate classification of severe hemophilia A patients, establishing a more direct correlation between FVIII activity and the frequency and severity of bleeding episodes, leading to a more accurate prediction of bleeding risk.

Laboratory screening tests require the automated and standardized methods. In contrast to previous continuous TG assays, the novel TG assay disclosed herein can be well automated and more easily standardized by measuring the generated FIIa at certain time point (e.g., 3 min), offering rapid and simple laboratory tests of hyo- and hyper-coagulation states in patients. In addition, it can provide the diagnostic kit with much lower cost since the kit includes very small amounts of components rTF, FIXa, PL, and high sensitive FIIa substrate. This indicates that the kit has big benefits in commercialization The goal of the inventors was to establish the novel laboratory tests replacing the conventional clotting assays. For the goal, they have developed a novel TG assay methods with some modifications of classic methods. Application of the instant method and assay to the diagnostic laboratory test of FVIII activity has been validated by analytical determination of sensitivity, specificity and reproducibility, and by performing recovery tests with FVIII-spiked plasma from patients with severe FVIII deficiency. Further studies with Coumadin-plasma also support that the assay may be very useful for a personalized prediction of thrombotic and bleeding risk for patients. Based on the results from the assay validation studies, the inventors have determined that the prototype kits consist of coagulation factors rTF, FIXa and PL and high sensitive FIIa substrate.

In one embodiment, the inventors disclose lyophilized prototype diagnostic kits including rTF, FIXa, PL and FIIa substrate and then validate the novel assays by using clinical plasma samples obtained in collaboration with international medical institutions. The goal of these studies will be to prove that the novel assay enables a more detailed classification of hemophilia patients and prediction of thrombotic and bleeding risk for patients with anti-thrombotic treatment. In another embodiment, the assay and kit disclosed herein is further developed to create automatic devices and reagent kits.

Example 38

The Novel Coagulation Mechanism Supports Personalized Evaluation of Bleeding/Thrombosis Risk and Antithrombotic Therapy Safe and Effective antithrombotic therapy requires a better understanding of mechanisms that can be targeted to interrupt thrombosis while minimally impairing normal hemostasis. The present disclosure provides a previously unrecognized function of the extrinsic tissue factor (TF) coagulation initiation complex resistant to physiologic factor (F) Xa inhibitors. Endogenous TF pathway inhibitor (TFPI) controls activation of the prothrombinase cofactor, FV, and direct TF-induced thrombogenesis; but not selective activation of the anti-hemophilic cofactor, FVIII, by nascent FXa associated with TF-FVIIa. Direct activation of the intrinsic FVIIIa-FIXa complex by the TF pathway not only escapes control by endogenous inhibitors, but also by therapeutic doses of FXa-directed oral anticoagulants. Although these FXa inhibitors limit direct coagulation activation by TF, they preserve feed-forward FVIII and FIX activation by the TF initiation complex and, therefore, interfere less with hemostasis during antithrombotic treatment. These findings support the use of novel assay formats for predicting individual bleeding risk versus anti-thrombotic efficacy associated with widely prescribed vitamin K antagonists, specific FXa and thrombin (FIIa) inhibitors as well as strategies targeting FXI presently under development.

The currently known coagulation paradigm (FIG. 1A) cannot readily explain well-documented observations that drugs targeting the key proteases of the common coagulation pathway, FXa and thrombin, reduce the risk of severe and intracranial bleeding when dosed for antithrombotic efficacy comparable to that of vitamin K antagonists (VKA) affecting multiple coagulation factors. Reported exceptions to this conclusion, such as gastrointestinal bleeding, may result from organ-specific concentrations of the active oral drugs exceeding therapeutic plasma levels rather than systemic inhibition of hemostasis. A novel function of the extrinsic TF-FVIIa complex is presently disclosed, namely providing selective feed-forward activation of the FVIII anti-hemophilic cofactor independently of thrombin feedback loops. This specific reaction of nascent FXa escapes control by physiologic coagulation inhibitors, including TFPIα. Together with the previously recognized capacity of TF-FVIIa to generate the FIXa anti-hemophilic protease, direct FVIII activation completes a pathway to FVIIIa-FIXa intrinsic tenase activity fully integrated within TF/FVIIa-initiated coagulation and preceding the canonical direct activation of the com-mon coagulation pathway (FIG. 1B).

In one embodiment, the inventors have shown that activation of FIXa, the intrinsic tenase protease, follows distinct individual patterns when coagulation is initiated in blood flowing over a surface coated with a limiting concentration of relipidated recombinant tissue factor (rTF). Moreover, FVIII activation by nascent FXa in complex with TF-FVIIa resists pharmacologic as much as endogenous FXa inhibitors, which can explain the preservation of hemostasis during target-selective anticoagulant therapy. Unexpectedly, though, the effect of oral anticoagulants targeting FXa and thrombin is individually variable when tested under conditions that selectively evaluate the contribution of distinct coagulation pathways to thrombin generation. This provides new perspectives for the assessment of bleeding and thrombotic risk based on laboratory assays formatted to evaluate the relative function of different coagulation initiation and propagation pathways. Importantly, the new assay formats reveal that, contrary to current thinking, targeted oral anticoagulants may not be equally effective at constant dosage in all individuals.

Figure 23:
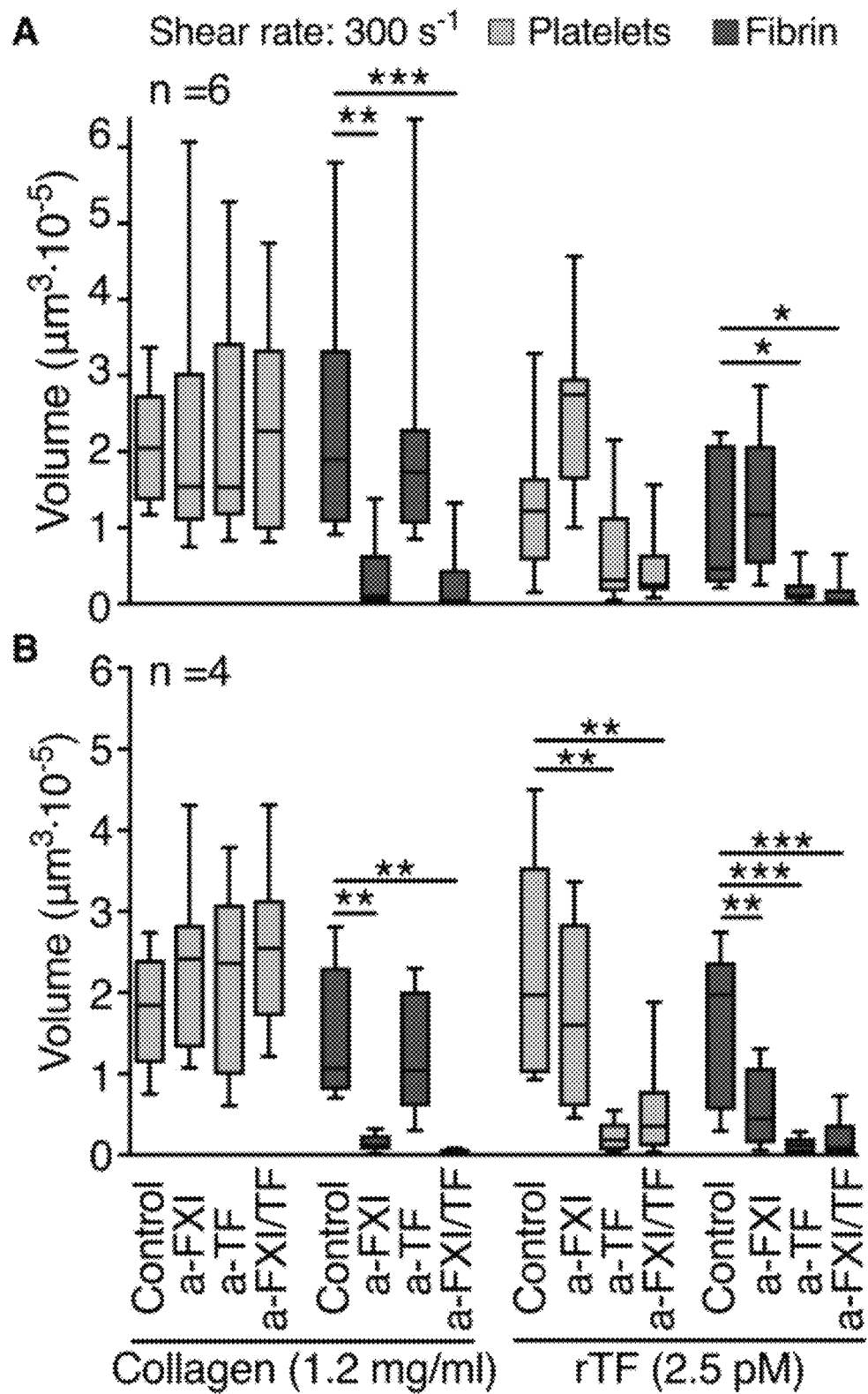
FIG. 23 illustrates, in accordance with embodiments herein, effect of blocking FXIa or TF function on platelet aggregation and fibrin deposition on surfaces coated with fibrillar collagen type I or rTF. Recalcified citrated whole blood was perfused at the wall shear rate of 300 $s^{-1}$ for 5 minutes. The volume of platelet aggregates visualized by mepacrine up-take and of fibrin visualized by a fluorescent antibody was measured by confocal microscopy.

The inventors have disclosed herein a flow-based assay with recalcified citrated whole blood to compare the relative role of the thrombin feedback loop generating FXIa and TF-FVIIa in the activation of FIX to FIXa. To this end, blood was perfused from 10 normal individuals over a surface coated with a limiting concentration of rTF previously shown to support coagulation activation and fibrin deposition dependent on FVIIIa and FIXa activity (see FIG. 16); the wall shear rate during perfusion was maintained at 300 $s^{-1}$. As a control, the same blood samples were perfused over a fibrillar collagen type I surface supporting platelet adhesion and aggregation independently of thrombin generation. FXIa and TF activity were blocked with specific monoclonal antibodies (MoAb) to inhibit FIXa generation selectively through the FXIa-by-thrombin feedback loop or TF-FVIIa, respectively. As expected, on the collagen surface the volume of platelet aggregates was not influenced by inhibiting coagulation pathways, while fibrin deposition was markedly reduced by the anti-FXIa MoAb and essentially unaffected by the anti-TF MoAb (FIG. 23A-B). These results are in agreement with the notion that coagulation activation on a collagen surface is initiated by FXIa generation through the FXIIa-dependent contact pathway.

On the rTF surface, surprisingly, the results obtained delineated two distinct patterns of coagulation initiation. In 6 out of the 10 normal individuals tested, fibrin formation was insensitive to inhibition of FXIa activity (FIG. 23A), but in the remaining 4 the anti-FXIa MoAb significantly reduced TF-initiated coagulation and fibrin formation (FIG. 23B). In all samples, the anti-TF MoAb essentially abolished fibrin deposition (FIG. 23A-B), in agreement with the recently demonstrated key role of TF-FVIIa-nascent FXa in the activation of FVIIIa required for thrombin generation under the chosen experimental conditions. Unlike fibrin volume, in no sample was the volume of platelet aggregates decreased significantly on the TF surface by inhibiting FXIa activity, while it was variably decreased by blocking TF activity but significantly so only in the 4 samples in which FXIa activity contributed to thrombin generation and fibrin formation (FIG. 23A-B).

Since FVIIIa-dependent coagulation is limited by FIXa availability, these findings indicate that, in ~60% of normal individuals, thrombin feedback activation of FXI is not limiting for intrinsic tenase-dependent coagulation, which derives FIXa for FVIIIa-FIXa complex formation from TF-FVIIa. In ~40% of normal individuals, instead, FIXa generation by FXIa is required for fibrin formation, thus FIXa generation by TF-FVIIa cannot contribute to normal coagulation. It was earlier suggested that FIXa produced by the extrinsic pathway, and its ability to function within the intrinsic Xase complex to activate X may play a significant role in producing Xa necessary for both the initiation and sustained phases of the procoagulant response following vascular damage. The inventors now find, using newly developed coagulation assay formats under flow, that the mechanisms leading to FIXa generation is an individual variable that may have implications on the effect of target specific anticoagulant drugs. The most obvious example is the new category of compounds that decrease the plasma concentration of FXI, developed on the current assumption that FIXa from the FXIa-thrombin feedback loop is key to coagulation amplification. This data suggest that their effect should be variable in patients with possibly as many as 60% showing limited effect of FIXa derived from TF-FVIIa.

Figure 24:
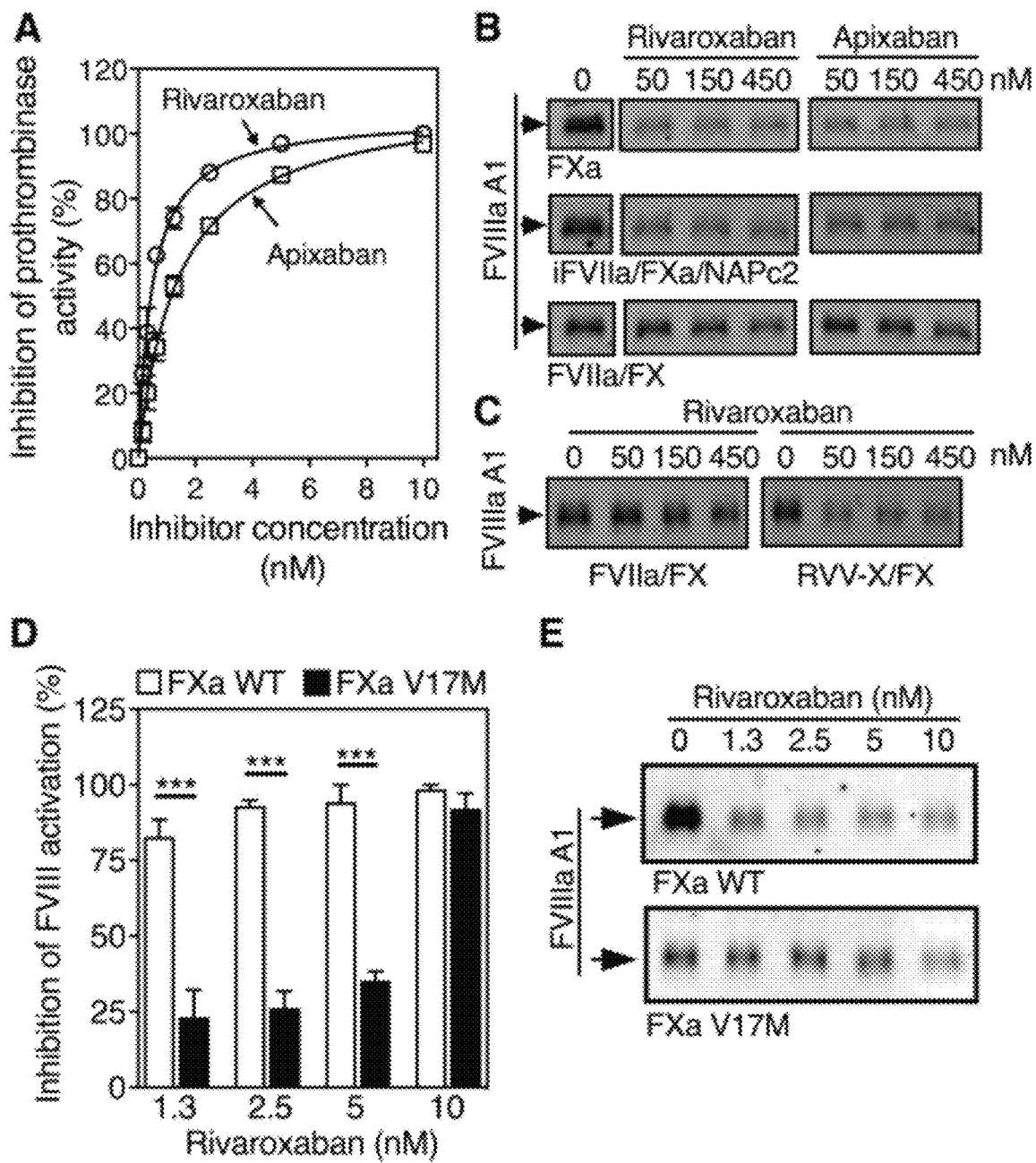
FIG. 24 illustrates, in accordance with embodiments herein, TF initiation of intrinsic coagulation escapes pharmacologic FXa inhibitors. (A) Rivaroxaban or apixaban effect on FXa (50 pM) prothrombinase activity in reactions with 50 pMrTFas phospholipid surface, 3 nM FVa and 1 µM prothrombin incubated 4 min, 37° C. (n=3). (B) Representative WB showing dose-dependent inhibition by rivaroxaban (n=5) or apixaban (n=3) of FVIIIa generation in reactions initiated by 100 pM FXa with 50 pM rTF (top); or 50 pMrTF, 100 pM iFVIIa, 100 pM FXa, 5 nM NAPc2 complex (middle); or 50 pM rTF, 200 pM FVIIa, 135 nM FX (bottom) in reactions with 700 pM FVIII, 3 nM FV, 200 nM lepirudin, 10 nM TFPIα (except with FXa, top) and 2.5 mM $CaCl_2$) incubated 120 s, 37° C. (C) Representative WB showing dose-dependent inhibition by rivaroxaban (n=2) of FVIIIa generation in reactions with 135 nM FX initiated by TF-FVIIa or Russel's viper venom (RVV) FX activator (13.5 pM) generating 1.25 and 1.23 nM FXa, respectively, in 120 s. (D) Quantitative WB evaluation of dose-dependent FVIIIa generation inhibition by rivaroxaban (n=3-4) in reactions containing FXa WT (25 pM) or V17M mutant (500 pM) with 1 nM rTF, 1 nM iFVIIa, 5 nM NAPc2, 200 nM lepirudin and 2.5 mM $CaCl_2$ incubated 120 s, 37° C. (E) Representative WB (n=3) of inhibition by rivaroxaban of FVIIIa generation by FXa WT or V17M mutant in reactions as in (D).

The efficacy of rivaroxaban and apixaban, FXa-targeting anticoagulants, was evaluated in different treated individuals. Rivaroxaban and apixaban comparably inhibit FXa pro-thrombinase activity with IC50 of 0.43±0.06 and 1.08±0.11 nM, respectively (FIG. 24A). At therapeutic concentrations of 50-450 nM, both inhibited by ~90% FVIIIa generation in reactions with purified components containing pre-activated FXa either free or in a complex with TF and active-site mutated FVIIa (iFVIIa) stabilized by the nematode anticoagulant protein (NAP) c2; in contrast, FVIIIa generation by nascent TF-FVIIa-FXa in reactions initially containing FX was only marginally affected (FIG. 24B). Resistance to the two FXa inhibitors was a specific property of FXa newly generated by TF-FVIIa since rivaroxaban inhibited FVIII activation by equivalent concentrations of FXa produced in situ by Russel's viper venom (RVV) FX activator (FIG. 24C). To evaluate whether the observed lack of inhibition reflected a kinetic disadvantage for inhibitors interacting with FXa in conformational transition from zymogen to protease, the inventors tested FXa with the substitution V17M restricting the ability to adopt active protease conformation. In a stable complex with TF-iFVIIa-NAPc2, FXa V17M could generate FVIIIa, albeit less efficiently than FXa WT. This activity, however, was insensitive to up to 5 nM rivaroxaban, whereas 1 nM almost completely inhibited FVIII activation by FXa WT (FIG. 24D-E). Thus, the dynamics of zymogen to protease transition contribute to the limited interference of direct FXa inhibitors with the function of nascent TF-FVIIa-FXa.

Figure 25:
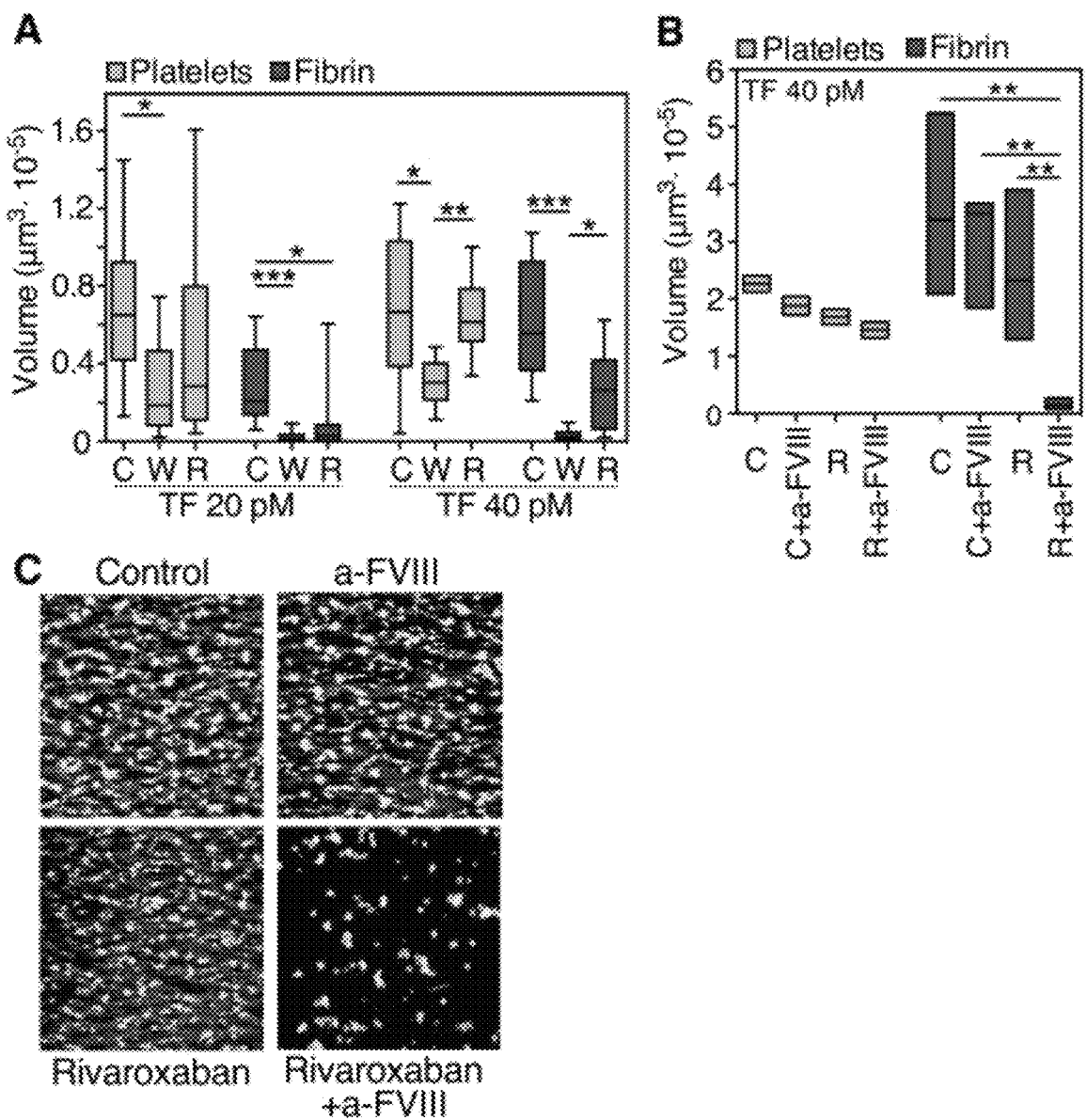
FIG. 25 illustrates, in accordance with embodiments herein, platelet and fibrin deposition experiments. (A) Platelet and fibrin deposition in experiments as in FIG. 23 but with rTF immobilized at the indicated coating concentrations. C (n=9), controls; W (n=12), warfarin treatment (average INR 2.6); R (n=10), rivaroxaban treatment (average plasma concentration 312 nM 2 hours post-intake). (B) Perfusion as in (A) but for 2 min using blood without—C— or with rivaroxaban—R— and/or anti-FVIII MoAb (n=3). Results—quantified on areas 4.65 times larger than in (A)—are shown as 25th-75th percentile bars with min/max whiskers (A) or min/max bars (B) and line at the median. *$P<0.05$, $P<0.01$, *$P<0.001$ evaluated by one-way ANOVA and Tukey post-test. (C) Representative confocal images (side=312 µm) of analyzed surfaces showing platelets/leukocytes (green), fibrin (red) and co-localization (yellow).

The results suggested that the antithrombotic effect of FXa-selective rivaroxaban and VKA warfarin—the latter affecting FVIIa and FIXa function in addition to FXa and FIIa—could vary on an in individual basis in treated patients. To test this hypothesis, the inventors measured platelet aggregation and fibrin deposition onto immobilized rTF exposed to flowing blood from patients receiving the two anticoagulant drugs compared to untreated controls (FIG. 25). Assay conditions were as used for the experiments shown in FIG. 2, but the sur-face TF concentration was increased such that coagulation initiation was no longer limited completely by FVIIIa activity in blood from untreated controls. The TF molar concentration for surface coating was adjusted considering the different specific procoagulant activity of individual rTF lots, measured as direct FXa generation by TF-FVIIa. Testing two different TF concentrations it was found that, with lower TF, the volume of deposited fibrin was markedly smaller in patients treated with either warfarin or rivaroxaban than controls, but with higher TF it was significantly greater in rivaroxaban than warfarin treated patients (FIG. 25A). Moreover, on the higher TF surface, rivaroxaban added to normal blood at the peak concentration range measured in treated patient plasma reduced fibrin volume partially, but nearly completely in the presence of an anti-FVIII MoAb that by itself produced modest inhibition (FIG. 25B-C). These findings demonstrate that, even at peak concentrations, selective FXa targeting inhibitors can distinctly preserve the newly unveiled TF-initiated pathway that directly enables intrinsic coagulation in flowing blood under control of physiologic inhibitors.

Figure 26:
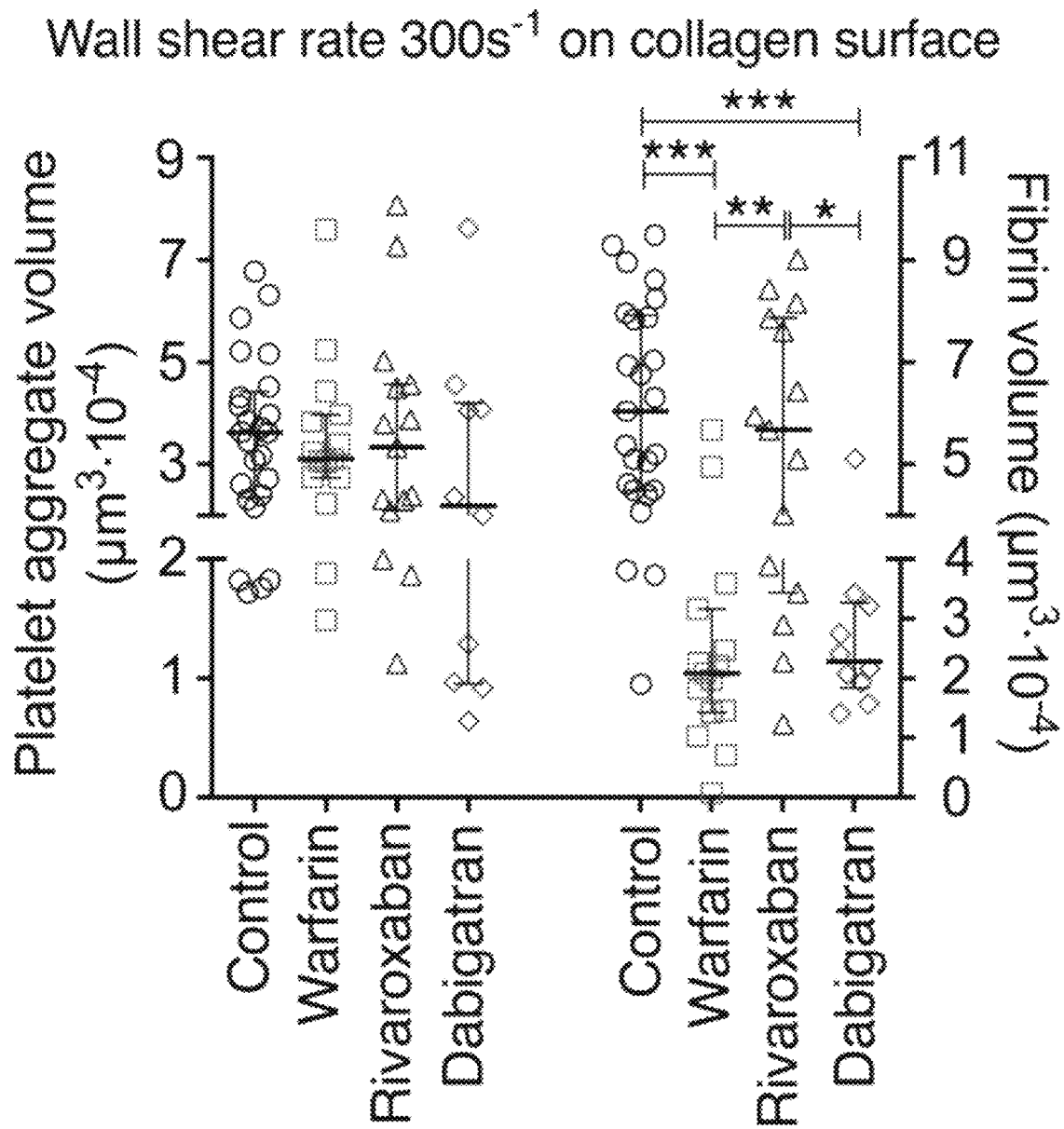
FIG. 26 illustrates, in accordance with embodiments herein, perfusion of recalcified citrated blood-blood from normal controls (n=25) and patients treated with warfarin (n=15), rivaroxaban (n=15) or dabigatran (n=10) over fibrillar collagen type I for 5 minutes at the wall shear rate of 300 $s^{-1}$. The volume of platelet aggregates and deposited fibrin was measured by confocal microscopy. Statistical analysis by one-way ANOVA and Tukey post-test. *$P<0.05$; $P<0.01$; *$P<0.001$.

These studies were extended by measuring platelet aggregation and fibrin deposition in blood from a larger cohort of patients treated with warfarin, rivaroxaban or the direct thrombin inhibitor, dabigatran. All anticoagulant regimens were long term and patients were receiving dosage according to currently accepted protocols. Warfarin treated patients were periodically monitored by measuring the INR coagulation index; patients treated with rivaroxaban or dabigatran received a fixed dose of the drug as currently prescribed, without measuring changes in coagulation. All studies were approved and monitored by Institutional Review Boards and performed according to standard protocols on experimentation in human subjects. The same experimental approach was used for the studies shown in FIG. 2, perfusing recalcified citrated whole blood over surfaces coated with fibrillar collagen type 1 or different rTF concentrations at a wall shear rate of 300 s$^{-1}$ for 5 minutes. On the collagen surface, the mean volume of platelet aggregates formed in control untreated samples or samples from patients treated with any of the three anticoagulant regimens was not significantly different, although in some patients it was below the lowest value measured in the control group, particularly in patients treated with the thrombin inhibitor, dabigatran (FIG. 26). This result is in agreement with the notion that platelet adhere to collagen and are activated to form aggregates independently of the generation of and stimulation by thrombin, which however can reinforce platelet activation and aggregation. In contrast, the volume of deposited fibrin was markedly reduced in patients receiving warfarin and dabigatran—indicating reduced thrombin generation and inhibition of thrombin activity, respectively—but not in those receiving rivaroxaban; indeed, in the latter, the mean volume of deposited fibrin was not significantly different from normal and significantly more than in the warfarin and dabigatran groups (FIG. 26).

Figure 27:
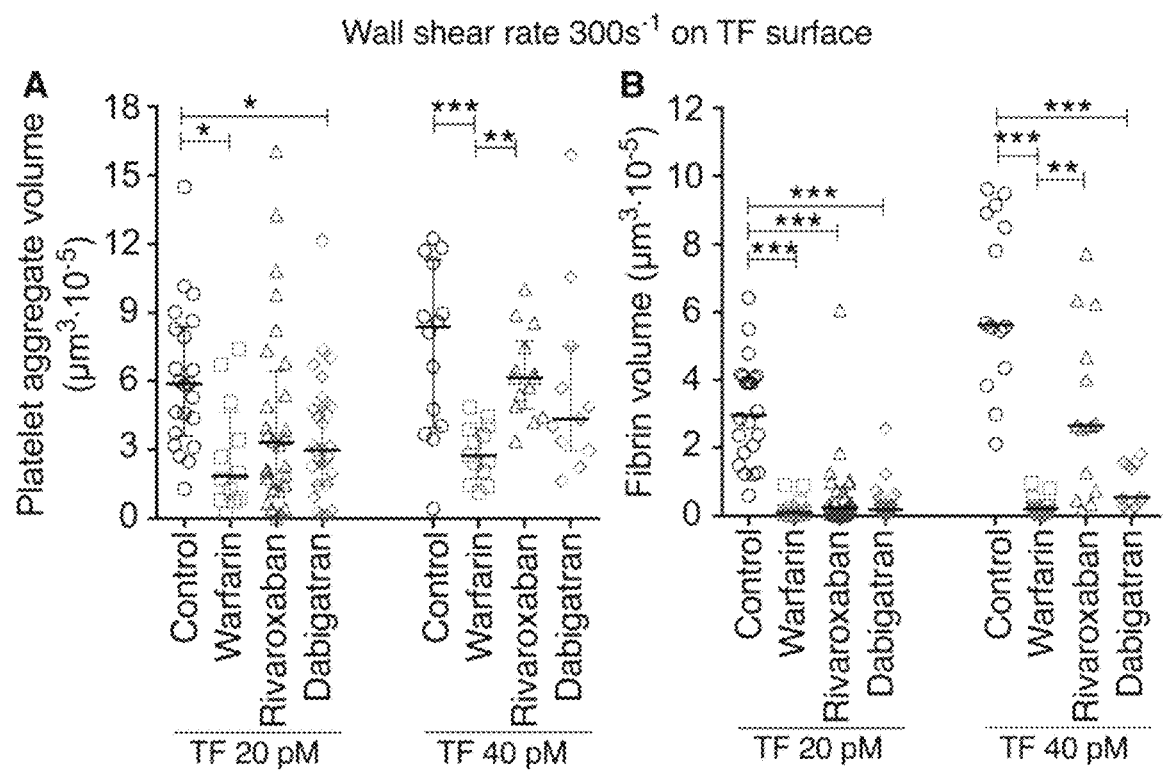
FIG. 27 illustrates, in accordance with embodiments herein, perfusion of recalcified citrated blood on rTF-coated surfaces, as indicated. (A) Volume of platelet aggregates. (B) Volume of deposited fibrin. For assays on 20 or 40 pM rTF coated surfaces the number of samples tested was, respectively: normal controls 22, 14; warfarin 12, 13; rivaroxaban 28, 14; dabigatran 27, 11.

On the rTF surface, results were interestingly different. Two coating concentrations (20 and 40 pM) were tested, as for the experiments shown in FIG. 25, and measured the volumes of platelet aggregates and deposited fibrin as for the experiments on collagen shown in FIG. 26. On either rTF surface, the volume of platelet aggregates was non significantly different from controls in patients receiving rivaroxaban; in those receiving warfarin, instead, it was significantly reduced on both rTF surfaces, and in those receiving dabigatran only on the surface with the lower rTF concentration (FIG. 27A). These results are in agreement with the concept that platelet adhesion and aggregation on immobilized TF requires activation provided by thrombin generated as a result of TF-induced coagulation. The results also show that the volume of platelet aggregates is a result of the level of thrombin generated and thrombin activity, which is lower in patients receiving warfarin and dabigatran than rivaroxaban at the dosage used. With respect to fibrin, all anticoagulant-treated patients, irrespective of the drug and dosage used, had markedly and significantly reduced deposition as compared to untreated controls when blood was perfused on the surface with lower rTF density (FIG. 27B). However, when surface TF was at a higher concentration, only blood from patients receiving warfarin and dabigatran still showed markedly reduced fibrin formation, while many rivaroxaban-treated samples exhibited fibrin formation in the normal range (FIG. 27B). The latter results is in agreement with the FXa inhibitor, rivaroxaban, not blocking FVIII activation by nascent TF-FVIIa-FXa and preserving function of the FVIIIa-FIXa intrinsic tenase complex bypassing also physiologic inhibitors of the TF pathway.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of assessing therapeutic efficacy of an anticoagulant, comprising:
   a. providing a blood sample that was contacted with the anticoagulant;
   b. perfusing the blood sample over a surface coated with collagen or immobilized rTF;
   c. inhibiting FXIa and TF activity with monoclonal antibodies (MoAb) O1A6 and 5G9 to inhibit FIXa generation selectively through the FXIa-by-thrombin feedback loop or TF-FVIIa;
   d. measuring platelet aggregation and fibrin deposition on the surface coated with collagen or immobilized rTF; and
   e. assessing therapeutic efficacy of the anticoagulant based on the volume of platelet aggregates and/or deposited fibrin.

2. The method of claim 1, wherein the anticoagulant is an FXa targeting coagulant.

3. The method of claim 1, wherein the anticoagulant is heparin, warfarin, dabigatran, rivaroxaban and/or apixaban.

4. The method of claim 1, wherein the perfusion is at a wall shear rate of 300 $s^{-1}$.

5. The method of claim 1, wherein the blood sample is a recalcified citrated whole blood sample.

6. The method of claim 1, wherein the collagen is fibrillar collagen type I.

7. The method of claim 1, wherein the FXIa and TF activity are further inhibited with MoAb 14E11 and/or 21E10.

* * * * *